(12) United States Patent
Bieniarz et al.

(10) Patent No.: US 11,808,770 B2
(45) Date of Patent: Nov. 7, 2023

(54) PROXIMITY ASSAYS USING CHEMICAL LIGATION AND HAPTEN TRANSFER

(71) Applicant: Ventana Medical Systems, Inc., Tucson, AZ (US)

(72) Inventors: Christopher Bieniarz, Tucson, AZ (US); Rui Hong, Oro Valley, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 548 days.

(21) Appl. No.: 16/809,290

(22) Filed: Mar. 4, 2020

(65) Prior Publication Data

US 2020/0271662 A1 Aug. 27, 2020

Related U.S. Application Data

(60) Division of application No. 15/603,079, filed on May 23, 2017, now Pat. No. 10,620,217, which is a
(Continued)

(51) Int. Cl.
*G01N 33/68* (2006.01)
*G01N 33/542* (2006.01)
*G01N 33/543* (2006.01)

(52) U.S. Cl.
CPC ....... *G01N 33/6845* (2013.01); *G01N 33/542* (2013.01); *G01N 33/54353* (2013.01); *G01N 2440/00* (2013.01)

(58) Field of Classification Search
CPC ............. G01N 33/542; G01N 33/6845; G01N 33/54353; G01N 2440/00
See application file for complete search history.

(56) References Cited

U.S. PATENT DOCUMENTS

| 4,711,955 A | 12/1987 | Ward et al. |
| 5,306,518 A | 4/1994 | Chablaix et al. |

(Continued)

FOREIGN PATENT DOCUMENTS

| CN | 101620233 | 1/2010 |
| CN | 102187225 | 9/2011 |

(Continued)

OTHER PUBLICATIONS

Conrad et al, 1996, "[20] In Vitro Selection of Nucleic Acid Apatamers That Bind Proteins", Methods in Enzymology, 267:336-367.
(Continued)

*Primary Examiner* — Shafiqul Haq
(74) *Attorney, Agent, or Firm* — CHARNEY IP LAW LLC; Thomas M. Finetti

(57) ABSTRACT

Methods for in situ detecting proximity of two targets of interest featuring an antibody conjugated with a cleavable bridge component having a detectable moiety and an antibody conjugated with a non-cleavable bridge component. The bridge components each have a chemical ligation group adapted to form a covalent bond under particular conditions and when the targets are in close proximity. Following covalent bond formation, the cleavable bridge component can be cleaved from the antibody, effectively transferring the detectable moiety to the non-cleavable bridge component. Detection of the detectable moiety is indicative of the targets being in close proximity. The methods are compatible with both chromogenic and fluorogenic detection systems. The methods may be used to perform assays wherein one or more than one proximity event is detected on the same slide.

6 Claims, 28 Drawing Sheets
(27 of 28 Drawing Sheet(s) Filed in Color)

Related U.S. Application Data continuation of application No. PCT/EP2015/077484, filed on Nov. 24, 2015.

(60) Provisional application No. 62/116,962, filed on Feb. 17, 2015, provisional application No. 62/084,452, filed on Nov. 25, 2014.

(56) References Cited

U.S. PATENT DOCUMENTS

| | | |
|---|---|---|
| 5,661,028 A | 8/1997 | Foote |
| 5,707,804 A | 1/1998 | Mathies et al. |
| 5,734,018 A | 3/1998 | Rutter et al. |
| 5,741,713 A | 4/1998 | Brown et al. |
| 6,444,421 B1 | 9/2002 | Chung |
| 7,695,929 B2 | 4/2010 | Kosmeder et al. |
| 8,658,389 B2 | 2/2014 | Bieniarz et al. |
| 8,686,122 B2 | 4/2014 | Bieniarz et al. |
| 2005/0131006 A1 | 6/2005 | Mukherjee et al. |
| 2006/0246524 A1 | 11/2006 | Bauer et al. |
| 2012/0129248 A1 | 5/2012 | Chee et al. |
| 2013/0260379 A1 | 10/2013 | Alexander et al. |

FOREIGN PATENT DOCUMENTS

| | | |
|---|---|---|
| CN | 102695803 | 9/2012 |
| CN | 103245789 B | 10/2014 |
| JP | 2013500725 | 1/2013 |
| JP | 2014074724 | 4/2014 |
| WO | 2008098100 A2 | 8/2008 |
| WO | 2009032716 A1 | 3/2009 |
| WO | 2010083463 A1 | 7/2010 |
| WO | 2011014879 A2 | 2/2011 |
| WO | 2011051709 A1 | 5/2011 |
| WO | 2014139980 A1 | 9/2014 |

OTHER PUBLICATIONS

Dan-Ying, L. et al., Proximity Ligation Assay: A New and Highly Sensitive Protein Detection Method, Chinese Journal of Biochemistry and Molecular Biology, (2008), pp. 383-389, vol. 24, No. 4.

Defazio-Eli, L., et al., Quantitative assays for the measurement of HER1-HER2 heterodimerization and phosphorylation in cell lines and breast tumors: applications for diagnostics and targeted drug mechanism of action, Breast Cancer Research, (2011), pp. R44, vol. 13.

Grossman et al, 2008, "Target-Catalyzed Transfer Reactions for the Amplified Detection of RNA", Angewandte Chemie International Edition, 47:7119-7122.

Gullberg, M. et al., Cytokine detection by antibody-basded proximity ligation, PNAS, (2004), pp. 8420-8424, vol. 101, No. 22.

International Search Report and Written Opinion dated Feb. 1, 2016 from corresponding PCT Application No. PCT/EP2015/077484 filed Nov. 24, 2015.

Mukherjee, A., et al., Profiling the HER3/PI3K Pathway in Breast Tumors Using Proximity-Directed Assays dentifies Correlations between Protein Complexes and Phosphoproteins, PLOS one, (2011), pp. e16443.1-e16443.11, vol. 6.

Tang, N. et al., Proximity Ligation Assay and Its Application in Pathogen Detection, Progress in Veterinary Medicine, (2011), pp. 77-79, vol. 32, No. 7.

Van Dieck et al, 2014, "Development of Bispecific Molecules for the In Situ Detection of Protein-Protein nteractions and Protein Phosphorylation", Chemistry & Biology, 21:357-368.

Weerapana, E., et al., Tandem orthogonal proteolysis-activity-based protein profiling (TOP-ABPP)—a general method for mapping sites of probe modification in proteomes, Nature Protocols, (2007), pp. 1414-1425, vol. 2.

Zheng, L. et al., Biological detection based on proximity ligation assay, Journal of Molecular Diagnosis and Therapy, (2012), pp. 217-221, vol. 4, No. 4.

FIG. 14A
FIG. 14B
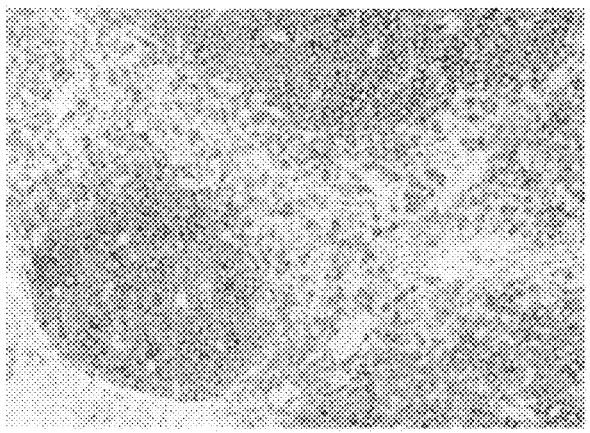
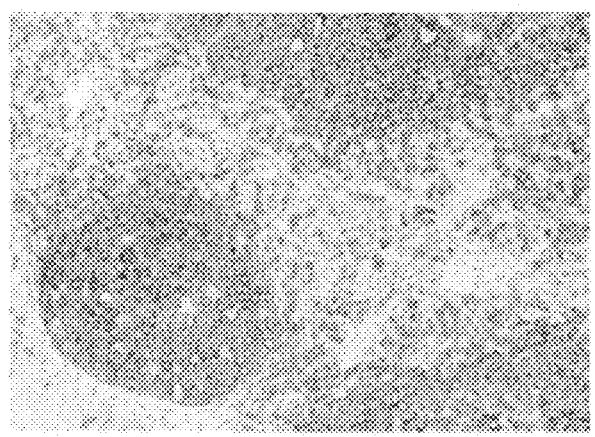
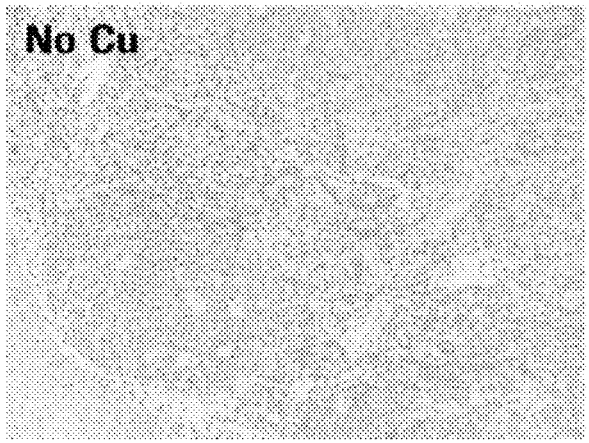
FIG. 14C

FIG. 18A
FIG. 18B
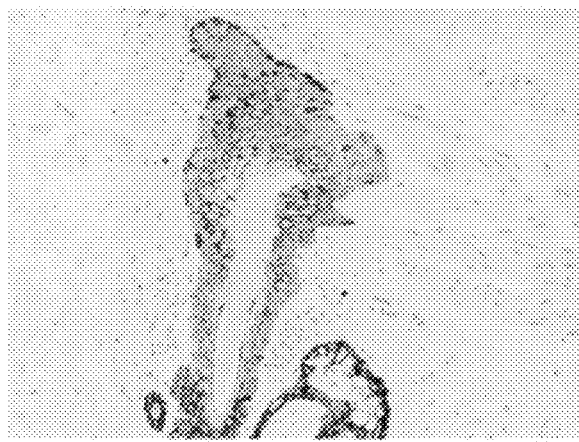
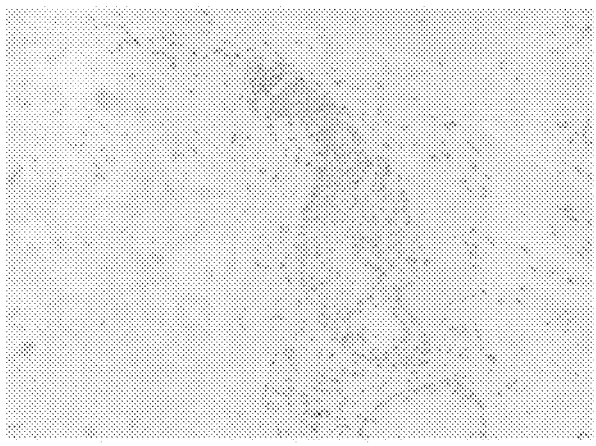
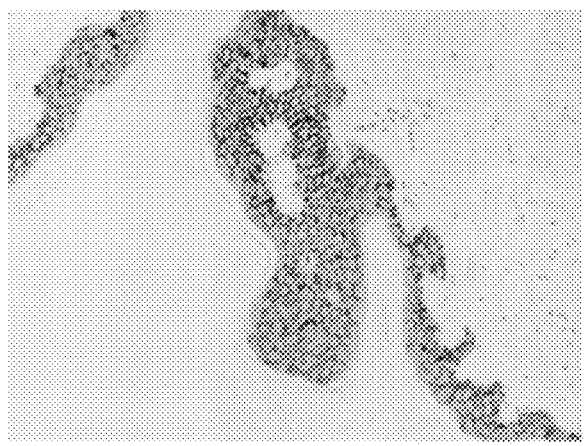
FIG. 18C
FIG. 18D

FIG. 19A
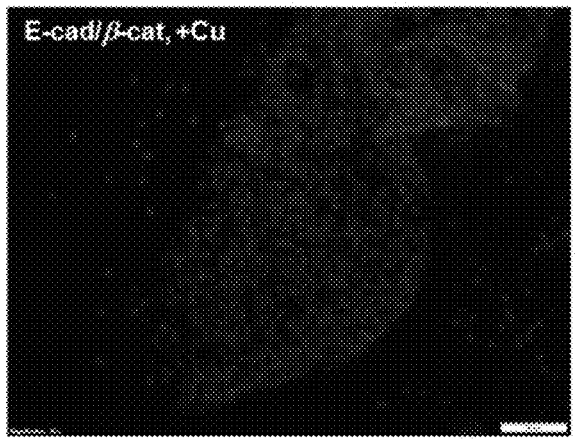
FIG. 19B
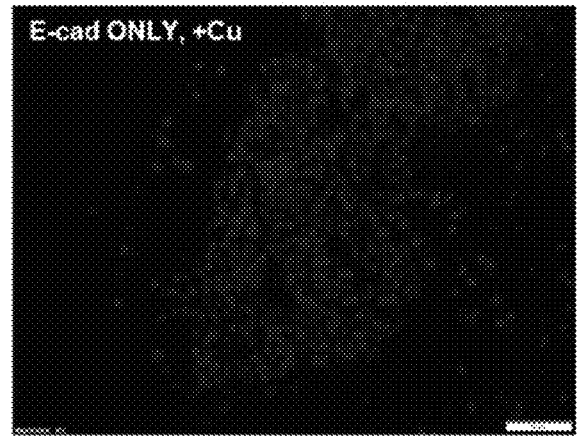
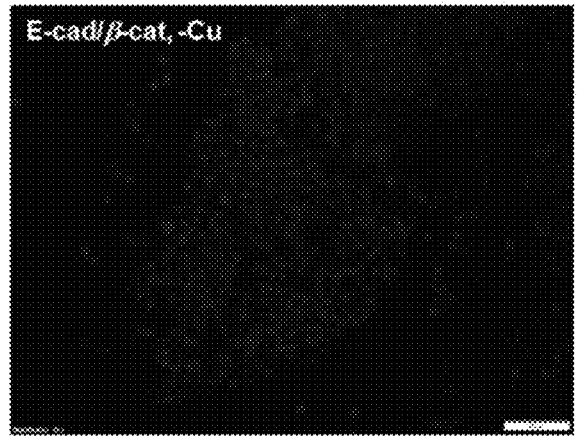
FIG. 19C

FIG. 20A    FIG. 20B
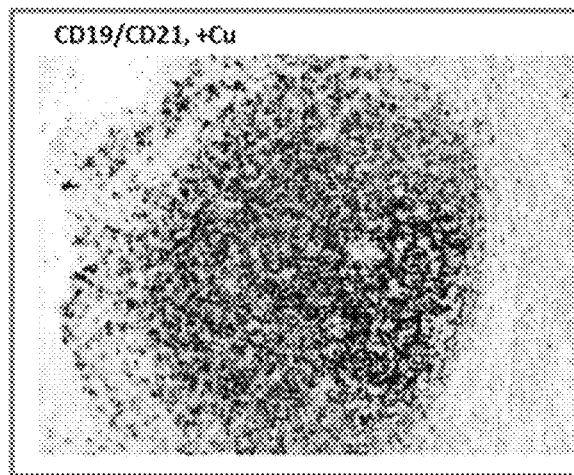 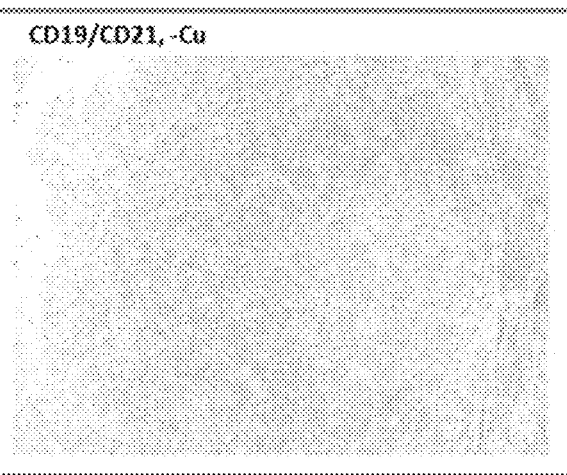
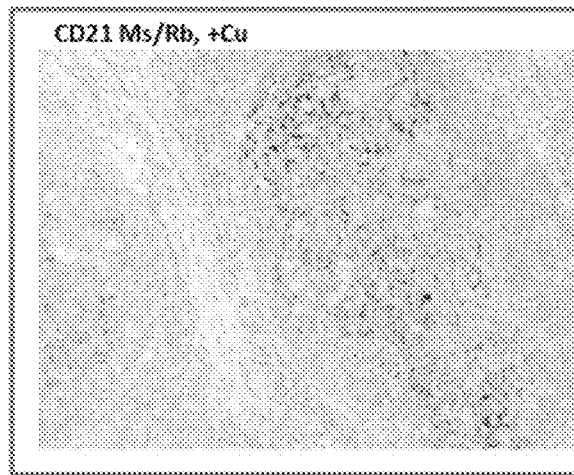 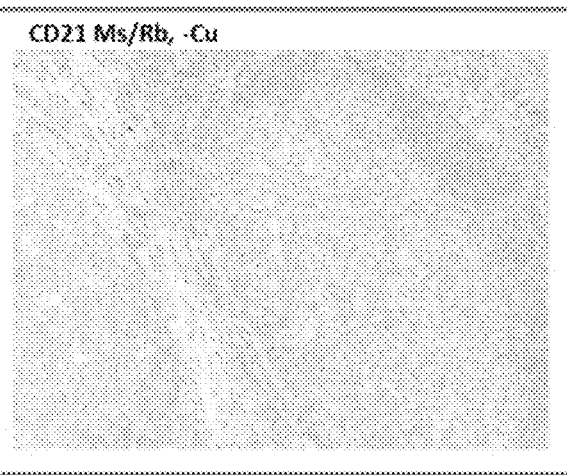
FIG. 20C    FIG. 20D

PROXIMITY ASSAYS USING CHEMICAL LIGATION AND HAPTEN TRANSFER

CROSS-REFERENCE TO RELATED APPLICATIONS

This patent application is a divisional of U.S. patent application Ser. No. 15/603,079 filed on May 23, 2017, which is a continuation of International Patent Application No. PCT/EP2015/077484 filed Nov. 24, 2015, which claims priority to and the benefit of U.S. Provisional Application No. 62/084,452, filed Nov. 25, 2014 and also to U.S. Provisional Application No. 62/116,962, filed Feb. 17, 2015. Each of the above patent applications is incorporated herein by reference as if set forth in its entirety.

FIELD OF THE INVENTION

The present invention relates to in situ proximity assays, in particular, proximity assays using proximity-induced chemical ligation reactions to form covalent bonds and subsequent transfer of detectable hapten. The present invention also features detection of protein-protein interactions, fusion proteins, and protein post-translational modification.

BACKGROUND OF THE INVENTION

Proximity assays are used to assess whether two particular proteins or portions thereof are in close proximity, e.g., proteins that are bound to each other, fusion proteins, and/or proteins that are positioned in close proximity. One such assay, known as proximity ligation assay (PLA), features two antibodies (raised in different species) bound to the targets of interest (see *Nature Methods* 3, 995-1000 (2006)). PLA probes, which are species-specific secondary antibodies with a unique oligonucleotide strand attached, are then bound to the appropriate primary antibodies. In the case of the targets being in close proximity, the oligonucleotide strands of the PLA probes can interact with additional ssDNA and DNA ligase such they can be circulated and amplified via rolling circle amplification (RCA). When highly processive DNA polymerases such as Phi29 DNA polymerase is used, the circular DNA template can be replicated hundreds to thousands of times longer and as a result producing ssDNA molecules from hundreds of nanometers to microns in length (see *Angewandte Chemie International Edition*, 2008, 47, 6330-6337). After the amplification, the replicated DNA can be detected via detection systems. Thus, a visible signal is indicative that the targets of interest are in close proximity. These assays feature the use of several DNA-antibody conjugates as well as enzymes such as DNA ligase and DNA polymerase. These conjugates and enzymes can be expensive, and they also require stringent assay conditions in order for proper function and stability. Furthermore, the approach generates an amplified DNA sequence, while easy to detect, may not remain co-localized with the proximity event detected.

Another assay for investigating protein-protein interactions includes a dual binders (DB) assay, which utilizes a bi-specific detection agent consisting of two Fab fragments with fast off-rate kinetics joined by a flexible linker (Development of Bispecific Molecules for the In Situ Detection of Protein-Protein Interactions and Protein Phosphorylation, *Chemistry & Biology* 21, 1-12, Mar. 20, 2014). In principle, because the dual binders comprise Fab fragments with fast off-rate kinetics, the dual binders are washed off if only one of the Fab fragments is bound to its epitope (simultaneous cooperative binding of both Fab fragments of the dual binder prevents dissociation of the dual binder and leads to positive staining/visibility). These approaches require the specific development of fab fragments with specific binding kinetics, which makes their implementation to the breadth of targets of interest unreasonable.

In another approach, Grossman et al. describe an assay for the detection of proximal target nucleic acids by the transfer of a reporter group from a donating probe to a nearby accepting probe. The probes are designed to anneal adjacently to complementary segments of the target nucleic acid. The annealing of the probe pair (in close proximity) allows for reactions (e.g., a thio-exchange reaction, etc.) to occur, which facilitates the transfer of the reporter group (e.g., fluorescence quencher) (see Grossman et al., *Angew. Chem. Int. Ed.* 2008, 47, 7119-7122).

According to another approach, PCT Published Application WO2014/139980, which is incorporated by reference in its entirety for disclosure related to proximity assays and tools for enabling the same, describes the use of a biotin ligase substrate and an enzyme to perform a proximity assay. The method provides detection of target molecules and proximity while maintaining the cellular context of the sample. The use of biotin ligase such as an enzyme from *Escherichia coli* and peptide substrate such as amino-acid substrate for that enzyme provides for a sensitive and specific detection of protein-protein interactions in FFPE samples. Because biotin ligase can efficiently biotinylate appropriate peptide substrate in the presence of biotin and the reaction can only occur when the enzyme makes physical contact with the peptide substrate, biotin ligase and the substrate can be separately conjugated to two antibodies that recognize targets of interest respectively.

SUMMARY OF THE INVENTION

The present invention features methods for detecting target proximity. The invention features, as described more inclusively herein, methods for detecting target proximity wherein (i) a chemical reaction step forms a covalent bond between a pair of modified specific binding molecules (e.g., two antibodies each conjugated with a bridge component adapted to form a covalent bond (chemical ligation) when in close proximity and upon external stimulation, one of the bridge components also comprises a cleavable bond and a detectable moiety) and (ii) a subsequent/separate cleavage step cleaves the bridge component originally associated with the detectable moiety so that the detectable moiety is ultimately transferred to the opposing specific binding molecule. Detection of the detectable moiety indicates target proximity as the detectable moiety that is not engaged in chemical bond formation due to insufficient proximity would be removed from the sample by washing.

The methods of the present invention are compatible with both chromogenic and fluorogenic detection systems and the methods may be performed either manually or in an automated system. Because the methods of the present invention do not feature the use of enzymes such as DNA ligase or DNA polymerase, the methods use less sensitive and costly reagents for detecting target proximity and one that may have more flexibility and tolerance with respect to assay conditions.

Importantly, the specific binding molecules of the present invention (e.g., antibodies) may be conjugated with one or multiple (e.g., two, three, four, five, 6, 7, 8, 9, 10, or more) bridge components. This may be advantageous as multiple bridge components can both provide an enhanced (e.g., darker) signal as well as a greater likelihood of achieving a signal.

The diversity of uses for the present invention is surprising. For example, the included examples demonstrate that the invention may be used to detect protein-protein interactions and post-translational modification (PTM) states. As such, provided are approaches for detecting various proximal biologically significant targets such as protein dimerization, protein fusions, associations, and PTM including phosphorylation, glycosylation, ubiquitination, SUMOylation, nitrosylation, methylation, acetylation, lipidation, and/or the like.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

For example, in some embodiments, methods of the present invention comprise binding a first modified binding molecule to the first target to form a first complex, and binding a second modified binding molecule to the second target to form a second complex.

The first modified binding molecule may comprise a cleavable bridge component (or more than one cleavable bridge component), wherein the cleavable bridge component comprises a cleavage site (e.g., a disulfide bond, a vicinal diol, a vicinal hydroxylamine, a nitrophenyl derivative, etc.), a detectable moiety (e.g., one, at least one, at least two, at least 3, at least 4, at least 5, at least 6, at least 7, at least 8, at least 9, at least 10, etc.), and a first chemical ligation group (e.g., an azide, a thioester, a tetrazole ring, etc.). The cleavage site is more proximal to the first modified binding molecule than is the detectable moiety and the first chemical ligation group. The first chemical ligation group is located at a terminus of the cleavable bridge component. The first chemical ligation group is stable under physiological conditions.

The second modified binding molecule may comprise a non-cleavable bridge component (or more than one non-cleavable bridge component) wherein the non-cleavable bridge component comprises a second chemical ligation group (e.g., an alkyne group, a halogen group (—Cl, —Br, —I, etc.), an alkene group, etc.). The second chemical ligation group is located at a terminus of the non-cleavable bridge component. The second chemical ligation group is stable under physiological conditions. The chemical ligation group is interchangeable between the first and the second modified binding molecule.

In some embodiments, the first modified binding molecule comprises a first antibody, and the second modified binding molecule comprises a second antibody. In some embodiments, the first modified binding molecule comprises a first primary antibody and a first secondary antibody, and the second modified binding molecule comprises a second primary antibody and a second secondary antibody; the first secondary antibody is specific for the first primary antibody and not the second primary antibody, and the second secondary antibody is specific for the second primary antibody and not the first primary antibody; and the cleavable bridge component is bound to the first secondary antibody and the non-cleavable bridge component is bound to the second secondary antibody.

The method may further comprise covalently linking the first chemical ligation group to the second chemical ligation group to form a covalently bonded unit, cleaving the cleavage site of the cleavable bridge component such that the covalently bonded unit is bound to the second modified binding molecule and not the first modified binding molecule, removing cleavable bridge components that are not part of a covalently bonded unit (e.g., washing), and making the detectable moiety visible (e.g., via a chromogenic system, a fluorescence system, etc.).

The methods of the present invention may comprise binding a first primary antibody to the first target and binding a second primary antibody to the second target; then binding a first secondary antibody to the first primary antibody and binding a second secondary antibody to the second primary antibody, wherein the first secondary antibody is specific for the first primary antibody and not the second primary antibody, and the second secondary antibody is specific for the second primary antibody and not the first primary antibody. The first secondary antibody may be the first modified binding molecule as described above, e.g., comprising a cleavable bridge component as previously described. The second secondary antibody may be the second modified binding molecule as described above, e.g., comprising a non-cleavable bridge component as described above. The methods may further comprise covalently linking the first chemical ligation group to the matching second chemical ligation group to form a covalently bonded unit; cleaving the cleavage site of the cleavable bridge component such that the covalently bonded unit is bound to the second secondary antibody and not the first secondary antibody; removing cleavable bridge components that are not part of a covalently bonded unit; and making the detectable moiety visible.

In some embodiments, visibility of the detectable moiety indicates that the first target and the second target are no more than 60 nm apart, no more than 50 nm apart, no more than 40 nm apart, no more than 30 nm apart, no more than 25 nm apart, no more than 15 nm apart, no more than 10 nm apart, no more than 5 nm apart, etc.

Methods of the present invention may be performed manually or using an automated staining machine. One aspect of the present is that the reagents, and kits for performing the assay, are sufficiently stable so that they can be used on an automated staining instrument. For example, the reagents are configurable to have a shelf-life of greater than 1 month at room temperature.

In some embodiments, the detectable moiety comprises a non-endogenous compound, a peptide tag, (e.g., HA-tag derived from hemagglutinin, FLAG tag, Myc Tag, V5 Tag, E-Tag, VSV Tag, etc.) or an oligonucleotide. In some embodiments, the cleavable bridge component comprises x polyethylene glycol groups ($PEG_x$), wherein $x \geq 1$. In some embodiments, the non-cleavable bridge component comprises x polyethylene glycol groups ($PEG_x$), wherein $x \geq 1$.

In some embodiments, the step of covalently linking the first chemical ligation group to the second chemical ligation group comprises contacting the sample with a catalyst (e.g., copper (I) for initiating a Huisgen 1,3-dipolar cycloaddition reaction), ultraviolet light, or a deprotection condition (e.g., hydrazine ($N_2H_4$)). In some embodiments, the chemical ligation groups are adapted to form the covalently bonded unit in less than two hours.

In some embodiments, the step of cleaving the cleavage site of the cleavable bridge component comprises contacting the sample with a reducing agent (e.g., dithiothreitol (DTT), beta-mercaptoethanol (BME), or tris(2-carboxyethyl)phosphine (TCEP)), sodium periodate (NaIO$_4$), or ultraviolet light. In some embodiments, the cleavage site comprises a disulfide bond, a vicinal diol, a vicinal hydroxylamine, or a nitrophenyl derivative.

One aspect of the present invention is that the assay can be done in a time that is both commercially reasonable and chemically robust (e.g. the times are sufficiently low such that the adverse impact of hydrolysis and thermal degradation are not impactful on the assay performance—the main reason for shorter time is more for increased test efficiency). In some embodiments, the chemical ligation groups are adapted to form the covalently bonded unit in less than four hours, three hours, two hours, or one hour.

The present invention also features compositions for detecting target proximity, e.g., compositions used in methods described herein. For example, the present invention features a composition comprising a cleavable bridge component, as described herein. The composition may further comprise an antibody conjugated to the cleavable bridge component. In some embodiments, the antibody is conjugated with at least one cleavable bridge component. In some embodiments, the antibody is conjugated with at least two cleavable bridge components, at least five cleavable bridge components, at least ten cleavable bridge components, or at least fifteen cleavable bridge components. The present invention also features a composition comprising a non-cleavable bridge component, as described herein. The composition may further comprise an antibody conjugated to the non-cleavable bridge component. In some embodiments, the antibody is conjugated with at least one non-cleavable bridge component. In some embodiments, the antibody is conjugated with at least two non-cleavable bridge components, at least five non-cleavable bridge components, at least ten non-cleavable bridge components, or at least fifteen cleavable bridge components.

Kits for practicing the disclosed embodiments are also disclosed. For example, the present invention features a kit comprising a first modified binding molecule and/or a second modified binding molecule as described herein. The kit may further comprise a catalyst effective for covalently linking the first chemical ligation group to the second chemical ligation group to form a covalently bonded unit. In some embodiments, the chemical ligation groups are adapted to form the covalently bonded unit in less than four hours, three hours, two hours, or one hour. In some embodiments, the kit further comprises a reagent for cleaving the cleavage site of the cleavable bridge component. In some embodiments, the kit further comprises a system for making the detectable moiety visible.

In some embodiments, the first target comprises a target protein and the second target comprises a post-translational modification (e.g., phosphorylation, ubiquitination, glycosylation, ubiquitination. etc.). Thus, the assays of the present invention may be used for in situ detection of a target protein having post-translational modifications (e.g., phosphorylation, ubiquitination, glycosylation, ubiquitination. etc.).

SEQUENCE LISTING INCORPORATION BY REFERENCE

This application hereby incorporates-by-reference a sequence listing submitted herewith in a computer-readable format, having a file name of 32348_Project_ST25, created on May 11, 2017, which is 1,330 bytes in size.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 14A is a photomicrograph showing detection of CD20 in tonsil sections showing the effect of Cu(I)/L ratio and the attendant staining with a Cu(I)/L ratio of 1:5. A reactive acetylene group in the conjugate of GAM-PEG$_4$-CCH was used (see Example 3). Specific detection of CD20 was achieved when Cu(I) was added. No staining was observable when Cu was omitted. This indicates the presence of reactive acetylene functionality in GAM conjugate.

FIG. 14B is a photomicrograph showing detection of CD20 in tonsil sections showing the effect of Cu(I)/L ratio and the attendant staining with a Cu(I)/L ratio of 1:3. A reactive acetylene group in the conjugate of GAM-PEG$_4$-CCH was used (see Example 3). Specific detection of CD20 was achieved when Cu(I) was added. This indicates the presence of reactive acetylene functionality in GAM conjugate.

FIG. 14C is a photomicrograph showing detection of CD20 in tonsil sections showing the effect of Cu(I)/L ratio and the attendant staining with a no Cu(I) added. A reactive acetylene group in the conjugate of GAM-PEG$_4$-CCH was used (see Example 3). No staining was observable when Cu was omitted. This indicates the presence of reactive acetylene functionality in GAM conjugate.

FIG. 18A is a photomicrograph showing detection of E-cadherin(E-cad)/β-catenin(β-cat) in normal skin tissue sections stained with VENTANA OPTIVIEW DAB with amplification in a proximity assay between E-cad and β-cat.

FIG. 18B is a photomicrograph showing detection of E-cadherin(E-cad)/β-catenin(β-cat) in normal skin tissue sections stained with VENTANA OPTIVIEW DAB with amplification in a proximity assay between E-cad and β-cat.

FIG. 18C is a photomicrograph showing detection of E-cadherin(E-cad)/β-catenin(β-cat) in different normal skin tissue sections stained with VENTANA OPTIVIEW DAB with amplification in a proximity assay between E-cad and β-cat.

FIG. 18D is a photomicrograph showing detection of E-cadherin(E-cad)/β-catenin(β-cat) in normal skin tissue sections stained with VENTANA OPTIVIEW DAB with amplification showing the corresponding negative control in which the Cu(I) catalyst was excluded.

FIG. 19A is a photomicrograph showing fluorophore-tyramide based detection of Ecad/β-cat in normal tonsil sections using Cy5-Tyr (Blue=DAPI, Red=Cy5 for Ecad/β-cat).

FIG. 19B is an additional photomicrograph showing fluorophore-tyramide based detection of Ecad/β-cat in normal tonsil sections using Cy5-Tyr (Blue=DAPI, Red=Cy5 for Ecad/β-cat).

FIG. 19C is an additional photomicrograph showing fluorophore-tyramide based detection of Ecad/β-cat in normal tonsil sections using Cy5-Tyr (Blue=DAPI, Red=Cy5 for Ecad/β-cat).

FIG. 20A is a photomicrograph showing the proximity assay of CD19/CD21 in normal tonsil tissue sections stained with VENTANA OPTIVIEW DAB with amplification.

FIG. 20B is a photomicrograph showing control of the assay illustrated in FIG. 20A in which the Cu(I) was excluded.

FIG. 20C photomicrograph showing detection of CD21 by using mouse-anti-CD21 and rabbit-anti-CD21 primary antibodies in normal tonsil tissue.

FIG. 20D is photomicrograph showing the control of the assay illustrated in FIG. 20C in which the Cu(I) was excluded.

DESCRIPTION OF PREFERRED EMBODIMENTS

I. Terms

Figure 1A:
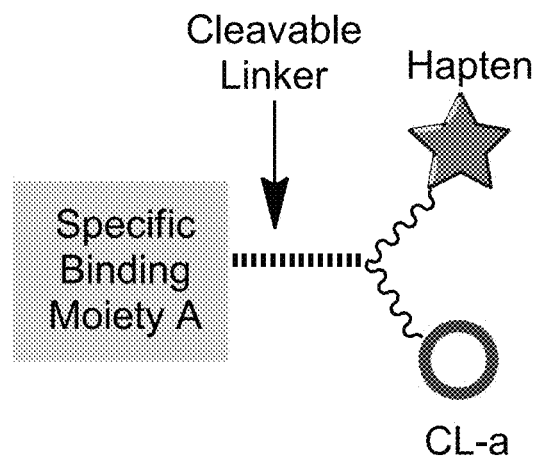
FIG. 1A is a schematic depiction of a modified specific binding moiety and a cleavable bridge component. The cleavable bridge components comprise a cleavage site (cleavable linker), a detectable moiety (hapten), and a chemical ligation group (CL). The hapten (detectable moiety) and the chemical ligation group can be in a linear or branched arrangement. Linkers can be used among all three functionalities. The cleavable linker is more proximal to the specific binding moiety than the other two groups.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes."

All publications, patent applications, patents, and other references mentioned herein are incorporated by reference in their entirety or for that portion relevant within the context of their reference. All GenBank Accession numbers are herein incorporated by reference as they appeared in the database on Jun. 8, 2011. In case of conflict, the present specification, including explanations of terms, will control. In addition, the materials, methods, and examples are illustrative and not intended to be limiting.

In order to facilitate review of the various embodiments of this disclosure, the following explanations of specific terms are provided:

Administration: To provide or give a subject an agent, for example, a composition, by any effective route. Exemplary routes of administration include, but are not limited to, oral, injection (such as subcutaneous, intramuscular, intradermal, intraperitoneal, and intravenous), sublingual, rectal, transdermal (e.g., topical), intranasal, vaginal and inhalation routes.

Agent: Any substance or any combination of substances that is useful for achieving an end or result; for example, a substance or combination of substances useful for decreasing or decreasing a protein-protein interaction. In some embodiments, the agent is a therapeutic agent, such as a therapeutic agent for the treatment of cancer.

Antibody: A polypeptide ligand including at least a light chain or heavy chain immunoglobulin variable region which specifically binds an epitope of an antigen or a fragment thereof. Antibodies include intact immunoglobulins and the variants of them well known in the art, such as Fab', F(ab)'2 fragments, single chain Fv proteins (scFv), and disulfide stabilized Fv proteins (dsFv). A scFv protein is a fusion protein in which a light chain variable region of an antibody and a heavy chain variable region of an antibody are bound by a linker, while in dsFvs, the chains have been mutated to introduce a disulfide bond to stabilize the association of the chains. The term also includes genetically engineered forms such as chimeric antibodies (for example, humanized murine antibodies) and heteroconjugate antibodies (such as, bispecific antibodies). See also, *Pierce Catalog and Handbook*, 1994-1995 (Pierce Chemical Co., Rockford, Ill.); Kuby, J., *Immunology*, 3rd Ed., W.H. Freeman & Co., New York, 1997.

The antibodies disclosed herein specifically bind a defined target (or multiple targets, in the case of a bispecific antibody). Thus, an antibody that specifically binds to a target is an antibody that binds substantially to the target, for example cells or tissue expressing the target. It is, of course, recognized that a certain degree of non-specific interaction may occur between an antibody and a non-target.

Typically, specific binding results in a much stronger association between the antibody and protein or cells bearing the antigen than between the antibody and protein or cells lacking the antigen. Specific binding typically results in greater than a 2-fold increase, such as greater than 5-fold, greater than 10-fold, or greater than 100-fold increase, in amount of bound antibody (per unit time) to a protein including the epitope or cell or tissue expressing the target epitope as compared to a protein or cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Biological sample: A biological specimen containing biological molecules, including genomic DNA, RNA (including mRNA and microRNA), nucleic acids, proteins, peptides, and/or combinations thereof. In some examples, the biological sample is obtained from a subject. In other examples, the biological sample is a cell culture, including a cell culture grown from a biological sample obtained from a subject. Biological samples include all clinical samples useful for detecting disease (e.g., cancer) in subjects, including, but not limited to, cells, tissues, and bodily fluids, such as blood, derivatives and fractions of blood (such as serum); as well as biopsied or surgically removed tissue, for example tissues that are unfixed, frozen, or fixed in formalin or paraffin. In a particular example, a biological sample is obtained from a subject having or suspected of having a tumor; for example, a subject having or suspected of having breast cancer, ovarian cancer, stomach cancer or uterine cancer. In some embodiments, the subject has or is suspected of having a carcinoma.

Buffers: Buffer solutions are commonly used to maintain correct pH levels for biological and chemical systems. Many of the exemplary embodiments disclosed herein include using a buffer solution. Representative buffering agents or salts that may be present in the buffer include, but are not limited to, Tris, Tricine, HEPES, MOPS, TAPS, Bicine, TAPSO, TES, PIPES, Cacodylate, SSC, MES, KCl, NaCl, potassium acetate, NH4-acetate, potassium glutamate, NH4Cl, ammonium sulphate, MgCl2, magnesium acetate and the like. One buffer solution is phosphate buffered saline (PBS). Another buffer solution is biotin ligase reaction buffer (0.1 M KCl, 5.5 mM MgCl2, 50 mM Tris-HCl (pH=8.0), 0.05% Brij-35, 0.1 mM dithiothreitol (DTT), 3 mM ATP, and 60 µM biotin). The amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to about 9.5, more typically a pH range of from about 6.5 to about 7.4 at room temperature. Other agents that may be present in the buffer medium include chelating agents, such as EDTA, EGTA and the like.

Chromogenic Staining: Chromogenic substrates have been used widely for immunohistochemistry for many years and for in situ hybridization more recently. Chromogenic detection offers a simple and cost-effective detection method. Chromogenic substrates have traditionally functioned by precipitating when acted on by the appropriate enzyme. That is, the traditional chromogenic substance is converted from a soluble reagent into an insoluble, colored precipitate upon contacting the enzyme. The resulting colored precipitate requires no special equipment for processing or visualizing. There are several qualities that successful IHC or ISH chromogenic substrates share. First, the substance should precipitate to a colored substance, preferably with a very high molar absorptivity. The enzyme substrate should have high solubility and reagent stability, but the precipitated chromogen products should be very insoluble, preferably in both aqueous and alcohol solutions. Enzyme turnover rates should be very high so as to highly amplify the signal from a single enzyme in a short amount of time. Until now, a relatively small number of chromogenic substances have been identified that legitimately possess all of these qualities. Reference is made to U.S. Published Application No. 2013/0260379 and 61/943,940, entitled QUINONE METHIDE PRECURSORS AND USES THEREFORE, filed on Feb. 24, 2014, which are hereby incorporated herein by reference in their entirety for disclosure related to chromogenic staining. Several commercially available chromogenic detection kits are available from Ventana Medical Systems, Inc. and referenced herein (AEC Detection Kit 760-020; Enhanced Alkaline Phosphatase Red Detection Kit 760-031; OPTIVIEW DAB IHC Detection Kit 760-700; iVIEW DAB Detection Kit 760-091; ULTRAVIEW Universal Alkaline Phosphatase Red Detection Kit 760-501; and ULTRAVIEW Universal DAB Detection Kit 760-500).

Conjugate: Two or more molecules coupled together, for example, by a covalent bond or non-covalent interaction.

Conjugate(ing), join(ing), bond(ing) or link(ing): Coupling a first molecule to a second molecule. This includes, but is not limited to, covalently bonding one molecule to another molecule, non-covalently bonding one molecule to another (e.g., electrostatically bonding) (see, for example, U.S. Pat. No. 6,921,496), hydrogen bonding, van der Waals forces, and any and all combinations of such couplings.

Contacting: Placement in direct association, for example solid, liquid or gaseous forms.

Control: A sample or standard used for comparison with a test sample, such as a biological sample, e.g., a biological sample obtained from a patient (or plurality of patients) or a cell culture. In some embodiments, a cell culture that is not incubated with a test agent serves as a control for a cell culture that is incubated with a test agent. In some embodiments, the control is a sample obtained from a healthy patient (or plurality of patients) (also referred to herein as a "normal" control), such as a normal breast sample. In some embodiments, the control is a historical control or standard value (i.e. a previously tested control sample or group of samples that represent baseline or normal values). In some embodiments the control is a standard value representing the average value (or average range of values) obtained from a plurality of patient samples.

Coupled: Two or more molecules joined together, either directly or indirectly. A first atom or molecule can be directly coupled or indirectly coupled to a second atom or molecule. A secondary antibody is indirectly coupled to an antigen when it is bound to a primary antibody that is bound to the antigen.

Detecting: To identify the existence, occurrence, presence, or fact of something. General methods of detecting are known to a person of ordinary skill in the art and may be supplemented with the protocols and reagents disclosed herein. For example, included herein are methods of detecting a first target proximal to a second target in a biological sample.

FFPE: Formalin fixed paraffin embedded sample.

Hapten: A hapten is a molecule, typically a small molecule that can combine specifically with an antibody, but typically is substantially incapable of being immunogenic except in combination with a carrier molecule. Many haptens are known and frequently used for analytical procedures, such as di-nitrophenyl, biotin, digoxigenin, fluorescein, rhodamine, or combinations thereof. Other haptens have been specifically developed by Ventana Medical Systems, Inc., assignee of the present application, including haptens selected from oxazoles, pyrazoles, thiazoles, nitroaryls, benzofurans, triterpenes, ureas, thioureas, rotenoids, coumarins, cyclolignans, and combinations thereof, with particular hapten examples of haptens including benzofurazan, nitrophenyl, 4-(2-hydroxyphenyl)-1H-benzo[b][1,4]diazepine-2(3H)-one, and 3-hydroxy-2-quinoxalinecarbamide. Plural different haptens may be coupled to a polymeric carrier. Moreover, compounds, such as haptens, can be coupled to another molecule using a linker, such as an NHS-PEG linker.

Immune complex: The binding of antibody to a soluble antigen forms an immune complex. The formation of an immune complex can be detected through conventional methods known to the person of ordinary skill in the art, for instance immunohistochemistry, immunoprecipitation, flow cytometry, immunofluorescence microscopy, ELISA, immunoblotting (i.e., Western blot), magnetic resonance imaging, CT scans, X-ray and affinity chromatography. Immunological binding properties of selected antibodies may be quantified using methods well known in the art.

Linker: Two components may be jointed together either directly through a bond or indirectly through a linker. Linkers may be bifunctional, i.e., the linker includes a functional group at each end, wherein the functional groups are used to couple the linker to the two components, either covalently or non-covalently. The two functional groups may be the same, i.e., a homobifunctional linker, or different, i.e., a heterobifunctional linker, but more typically are heterobifunctional. Where linkers are employed, suitable functional groups are selected to allow attachment of the two components, while not impairing the functionality of the components. Linkers of interest may vary widely depending on the components in the conjugate. In many embodiments the linker, when present, is biologically inert.

A linker may be used to link the detectable moiety and/or the chemical ligation group and/or the cleavage site of the cleavable bridge component to the specific binding molecule (or to link the chemical ligation group of the non-cleavable bridge component to the specific binding moiety). Linkers of different lengths can be selected. Where linkers are employed, such groups may be chosen to allow for attachment of the two components of the conjugate, while not impairing their functionality. Such terminal functional groups, include by way of example and without limitation, amines, alcohols, thiols, hydrazides, carbonyl-reactive group (such as aldehydes, acids and esters), vinyl ketones, epoxides, isocyanates, maleimides), functional groups capable of cycloaddition reactions, forming disulfide bonds, binding to metals or photo-reactive groups. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. These groups facilitate coupling to the specific binding moieties and other desired compounds. In some embodiments, the linker is at least about 25 daltons, at least about 50 daltons, at least about 100 daltons, or at least about 500 daltons (or larger). A first class of linkers may be the aliphatic compounds, such as aliphatic hydrocarbon chains having one or more sites of unsaturation, or alkyl chains. The length of the chain can vary, but typically has an upper practical limit of about 30 atoms. Chain lengths greater than about 30 carbon atoms have proved to be less effective than compounds having smaller chain lengths. Thus, aliphatic chain linkers typically have a chain length of from about 1 carbon atom to about 30 carbon atoms. However, a person of ordinary skill in the art will appreciate that, if a particular linker has greater than 30 atoms, and the conjugate still functions as desired, then such chain lengths are still within the scope of the present invention.

In some embodiments, the linker is a straight chain or branched alkyl chain functionalized with reactive groups, such as an amino- or mercapto-hydrocarbon, with more than two carbon atoms in the unbranched chain. Examples include aminoalkyl, aminoalkenyl and aminoalkynyl groups. Alternatively, the linker is an alkyl chain of 10-20 carbons in length, and may be attached through a Si—C direct bond or through an ester, Si—O—C, linkage (see U.S. Pat. No. 5,661,028 to Foote, incorporated herein by reference). Other linkers are available and known to a person of ordinary skill in the art (see, e.g., U.S. Pat. Nos. 5,306,518, 4,711,955 and 5,707,804; each of which is incorporated herein by reference).

A second class of linkers includes the alkylene oxides. The alkylene oxides are represented herein by reference to glycols, such as ethylene glycols. A person of ordinary skill in the art will appreciate that, as the number of oxygen atoms increases, the hydrophilicity of the compound also may increase. Thus, linkers of the present invention typically have a formula of $(-OCH_2CH_2-)_n$ where n is from about 2 to about 20, but more particularly n is from about 2 to about 10, and even more typically from about 4 to about 8, which can be represented as $PEG_4$ to $PEG_8$.

Linkers, such as heterobifunctional polyalkyleneglycol linkers, useful for practicing certain disclosed embodiments of the present invention are described in assignee's co-pending applications, including "Nanoparticle Conjugates," U.S. patent application Ser. No. 11/413,778, filed Apr. 28, 2006; "Antibody Conjugates," U.S. application Ser. No. 12/381,638, filed Mar. 13, 2009; and "Molecular Conjugate," U.S. patent application Ser. No. 12/687,564, filed Jan. 14, 2010, and U.S. Pat. No. 7,695,929; each of which is incorporated herein by reference. The linkers disclosed in these applications can be used to link specific binding moieties, biotin ligases, biotin ligase substrates, signal generating moieties and haptens in any and all desired combinations to form conjugates for use with disclosed embodiments of the present invention.

Other examples of linkers include, but are not limited to, peptides, including natural and non-natural polypeptides, carbohydrates, cyclic or acyclic systems that may possibly contain heteroatoms. Linker groups also may comprise ligands that bind to metals such that the presence of a metal ion coordinates two or more ligands to form a complex. In another embodiment, the linker is a pair of molecules, having high affinity for one another. Such high-affinity molecules include, for example, streptavidin and biotin, histidine and nickel (Ni), and GST and glutathione.

Specific exemplary linkers include: ethylene glycol, polyalkylene glycols such as $PEG_2$, $PEG_3$, $PEG_4$, $PEG_5$, $PEG_6$, $PEG_7$, $PEG_8$, $PEG_9$, $PEG_{10}$, $PEG_{11}$, $PEG_{12}$, $PEG_{13}$, $PEG_{14}$, $PEG_{15}$, $PEG_{16}$, $PEG_{17}$, $PEG_{18}$, $PEG_{19}$, $PEG_{20}$, 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine, succinimidyl-6-hydrazinonicotinamide(S-HyNic, HyNic-NHS), N-succinimidyl-4-formylbenzoate (S-4FB, 4-FB-NHS), maleimide HyNic (MHPH), maleimide 4FB (MTFB), succinimidyl-[(N-maleimidopropionamido)-octaethyleneglycol] ester (Mal-$PEG_8$-NHS), succinimidyl-[(N-maleimidopropionamido)-tetraethyleneglycol] ester (Mal-$PEG_4$-NHS), 4-FB-$PEG_4$-PFP, azidobenzoyl hydrazide, N-[4-(p-azidosalicylamino)butyl]-3'-[2'-pyridyldithio]propionamid), bis-sulfosuccinimidyl suberate, dimethyladipimidate, disuccinimidyltartrate, N-maleimidobutyryloxysuccinimide ester, N-hydroxy sulfosuccinimidyl-4-azidobenzoate, N-succinimidyl[4-azidophenyl]-1,3'-dithiopropionate, N-succinimidyl[4-iodoacetyl] aminobenzoate, glutaraldehyde, and succinimidyl-4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like.

Instead of chemical linkers, fusion proteins may be constructed (e.g., a peptide can be coupled to a specific binding molecule at the gene level).

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-o-methyl ribonucleotides, peptide-nucleic acids (PNAs), and the like. Such polynucleotides can be synthesized, for example, using an automated DNA synthesizer. It will be understood that when a nucleotide sequence is represented by a DNA sequence (i.e., A, T, G, C), this also includes an RNA sequence (i.e., A, U, G, C) in which "U" replaces "T."

Nucleotide: Term includes, but is not limited to, a base linked to a sugar, such as a pyrimidine, purine or synthetic analogs thereof, or a base linked to an amino acid, as in a peptide nucleic acid (PNA). A nucleotide is one unit in a polynucleotide. A nucleotide sequence refers to the sequence of bases in a polynucleotide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

Oligonucleotide: A linear polynucleotide sequence of between 5 and 100 nucleotide bases in length.

Proximal: Refers to the qualitative or quantitative distance between two molecules/targets/epitopes; for example, the distance between two proteins in a tissue sample. In some embodiments, molecules that are proximal to each other are within about 100 nm, about 75 nm, about 50 nm, about 35 nm, about 30 nm, about 25 nm, about 20 nm, about 15 nm, about 10 nm, about 5 nm or less distance of each other. Proximal may also provide a functional relationship. For examples, two targets (e.g., two proteins) may be considered proximal if the first target is within sufficient distance of the second target for a component associated with the first target to be bonded to a component associated with a second target. Another functional definition of proximal is the dimerization of two proteins. Another functional definition of proximal is associated to a genetic translocation. Two portions of the genome may be considered proximal when they are adjacent to each other or within 500,000 bp, within 100,000 bp, within 50,000 bp within 25,000 bp, within 10,000 bp, or within 1,000 bp of each other. This contrast to two portions which are not proximal due to a translocation (either a move to another chromosome or an inversion). The term proximal also includes a functional meaning as being the distance between molecules which enables a biologically significant interaction. For example, the distance between two proteins in a protein dimer, which has biological significance, can be said to be proximal.

Sample: Certain disclosed embodiments utilize biological samples. A biological sample is typically obtained from a mammalian subject of interest, such as a human. The sample can be any sample, including, but not limited to, tissue from biopsies, autopsies and pathology specimens. Biological samples also include sections of tissues, for example, frozen sections taken for histological purposes. Biological samples also include cell cultures or portions of cell cultures, for example, a cell culture grown from a biological sample taken from a subject.

Biological samples can be obtained from a subject using any method known in the art. For example, tissue samples can be obtained from breast cancer patients who have undergone tumor resection as a form of treatment. From these patients, both tumor tissue and surrounding non-cancerous tissue can be obtained. In some embodiments, the non-cancerous tissue sample used as a control is obtained from a cadaver. In some embodiments, biological samples are obtained by biopsy. Biopsy samples can be fresh, frozen or fixed, such as formalin-fixed and paraffin embedded. Samples can be removed from a patient surgically, by extraction (for example by hypodermic or other types of needles), by micro-dissection, by laser capture, or by any other means known in the art.

Specific binding moiety(ies): A member of a specific-binding pair. Specific binding pairs are pairs of molecules that are characterized in that they bind each other to the substantial exclusion of binding to other molecules (for example, specific binding pairs can have a binding constant that is at least $10^3$ greater, $10^4$ greater or $10^5$ greater than a binding constant for either of the two members of the binding pair with other molecules in a biological sample). The specific binding moiety used to make the exemplary conjugates disclosed herein may be any of a variety of different types of molecules, so long as it exhibits the requisite binding affinity for the target.

The specific binding moiety may comprise a small molecule or large molecule. A small molecule will range in size from about 50 to about 10,000 daltons, more typically from about 50 to about 5,000 daltons, and even more typically from about 100 to about 1000 daltons. A large molecule is one whose molecular weight is typically greater than about 10,000 daltons. The small molecule may be any molecule, typically an organic molecule that is capable of binding with the requisite affinity to the target. The small molecule typically includes one or more functional groups allowing it to interact with the target, for example by hydrophobic, hydrophilic, electrostatic or covalent interactions. Where the target is a protein, lipid or nucleic acid, the small molecule typically will include functional groups allowing for structural interactions such as hydrogen bonding, hydrophobic-hydrophobic interactions, electrostatic interactions, etc. The small molecule ligand often includes an amine, amide, sulfhydryl, carbonyl, hydroxyl or carboxyl group, and preferably at least two of these functional groups.

The small molecules often comprise cyclic and/or heterocyclic non-aromatic structures, and/or aromatic or polyaromatic structures substituted with one or more of the above functional groups. Also useful small molecules include structures found among biomolecules, including peptides, saccharides, fatty acids, steroids, purines, pyrimidines, derivatives, structural analogs or combinations thereof.

The small molecule may be derived from a naturally occurring or synthetic compound that may be obtained from a wide variety of sources, including libraries of synthetic or natural compounds. For example, numerous methods are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known small molecules may be subjected to directed or random chemical modifications, such as acylation, alkylation, esterification, amidification, etc., to produce structural analogs.

As such, the small molecule may be obtained from a library of naturally occurring or synthetic molecules, including a library of compounds produced through combinatorial means, i.e. a compound diversity combinatorial library. When obtained from such libraries, the small molecule employed will have demonstrated some desirable affinity for a target in a convenient binding affinity assay. Combinatorial libraries, as well as methods for their production and screening, are known in the art and are described in U.S. Pat. Nos. 5,741,713 and 5,734,018, the disclosures of which are incorporated herein by reference. Additional information concerning specific binding moieties is provided by assignee's U.S. Pat. No. 7,695,929, which also is incorporated herein by reference. The specific binding moiety may comprise a large molecule. Of particular interest as large molecule specific binding moieties are antibodies, as well as binding fragments and derivatives or mimetics thereof. As such, the specific binding moiety may be either a monoclonal or polyclonal antibody. Also of interest are antibody fragments or derivatives produced either recombinantly or synthetically, such as single chain antibodies or scFvs, or other antibody derivatives such as chimeric antibodies or CDR-grafted antibodies, where such recombinantly or synthetically produced antibody fragments retain the binding characteristics of the above antibodies. Such antibody fragments, derivatives or mimetics of the subject invention may be readily prepared using any convenient methodology, such as the methodology disclosed in U.S. Pat. Nos. 5,851,829 and 5,965,371, the disclosures of which are incorporated herein by reference.

Also suitable for use as large molecule specific binding moieties are polynucleic acid aptamers. Polynucleic acid aptamers may be RNA oligonucleotides that selectively bind proteins, much in the same manner as a receptor or antibody (Conrad et al., *Methods Enzymol.* (1996), 267(Combinatorial Chemistry), 336-367), or DNA oligomers that complement specific DNA target sequences.

In addition to antibody-based peptide/polypeptide or protein-based binding domains, the specific binding moiety may also be a lectin, a soluble cell-surface receptor or derivative thereof, an affibody or any combinatorially derived protein or peptide from phage display or ribosome display or any type of combinatorial peptide or protein library. Combinations of any specific binding moiety may be used.

Importantly, the specific binding moiety will be one that allows for coupling to the second component of the conjugate, or to a linker, without substantially affecting the binding affinity of the specific binding moiety to its target.

Particular examples of specific binding moieties include specific binding proteins (for example, antibodies, lectins, avidins such as streptavidins, and protein A). Specific binding moiety(ies) also includes the molecules (or portions thereof) that are specifically bound by such specific binding proteins.

Target: Any molecule for which the presence, location and/or concentration is or can be determined. Examples of target molecules include proteins and haptens, such as haptens covalently bonded to proteins. Target molecules are typically detected using one or more conjugates of a specific binding molecule and a detectable label. Examples of specific targets include proteins, carbohydrates, or nucleic acid molecules. Target nucleic acid molecules include those molecules whose proximity, rearrangement, amplification, deletion, detection, quantitation, qualitative detection, or a combination thereof, is sought. For example, the target can be a defined region or particular portion of a nucleic acid molecule, for example a portion of a genome (such as a gene or a region of DNA or RNA containing a gene (or portion thereof) of interest). The nucleic acid molecule need not be in a purified form. Various other nucleic acid molecules can also be present with the target nucleic acid molecule. For example, the target nucleic acid molecule can be a specific nucleic acid molecule (which can include RNA or DNA), the amplification of at least a portion thereof (such as a portion of a genomic sequence or cDNA sequence) is intended. In some examples, a target nucleic acid includes a viral nucleic acid molecule, or a bacterial nucleic acid molecule, such as a nucleic acid molecule from *Escherichia coli* or *Vibrio cholera*. Purification or isolation of the target nucleic acid molecule, if needed, can be conducted by methods known to those in the art, such as by using a commercially available purification kit or the like.

Tyramide Signal Amplification: An enzyme-mediated detection method that utilizes the catalytic activity of a peroxidase (such as horseradish peroxidase) to generate high-density labeling of a target molecule (such as a protein or nucleic acid sequence) in situ. TSA typically involves three basic steps: (1) binding of a specific binding member (e.g., an antibody) to the target followed by secondary detection of the specific binding member with a second peroxidase-labeled specific binding member; (2) activation of multiple copies of a labeled tyramide derivative (e.g., a hapten-labeled tyramide) by the peroxidase; and (3) covalent coupling of the resulting highly reactive tyramide radicals to residues (e.g., the phenol moiety of protein tyrosine residues) proximal to the peroxidase-target interaction site, resulting in deposition of haptens proximally (diffusion and reactivity mediated) to the target. In some examples of TSA, more or fewer steps are involved; for example, the TSA method can be repeated sequentially to increase signal. Methods of performing TSA and commercial kits and reagents for performing TSA are available (see, e.g., VENTANA Amplification Kit, Cat. No. 760-080, AmpMap Detection Kit with TSA™, Cat. No. 760-121, Ventana Medical Systems, Tucson, Ariz.; Invitrogen; kit No. T-20911, Invitrogen Corp, Carlsbad, Calif.). In some embodiments, TSA is a component of the provided PTDM. Other enzyme-catalyzed, hapten or signaling linked reactive species can be alternatively used as they may become available. Suitable conditions for TSA as well as reagents and kits for use for tyramide signal amplification are known to a person of ordinary skill in the art (see, e.g., Bobrow et al., *J. Immuno. Meth.*, 125:279-285, 1989).

Under conditions sufficient for: A phrase that is used to describe any environment that permits a desired activity.

II. Description of Embodiments

Referring now to FIG. 1-28, the present invention features proximity assay methods for detecting (in situ) whether two targets of interest are in close proximity. The methods of the present invention feature covalent bond formation. The methods of the present invention are compatible with both chromogenic and fluorogenic detection systems. The methods of the present invention may be performed manually, or the methods may be automated, (e.g., using an automated staining instrument such as a BENCHMARK XT, Ventana Medical Systems, Inc., Tucson, Ariz.), or a combination thereof. For example, the assay could be automated but include one or more manual steps in which a user adds reagents. Without wishing to limit the present invention to any theory or mechanism, it is believed that all or most of the components involved in the methods of the present invention are common chemical reagents that are readily available and inexpensive. Further, the synthesis of conjugates used in the assay may also be simple and/or high-yielding (similar to hapten labeling of antibodies).

The methods of the present invention may also be used to perform multiplex assays wherein more than one proximity event (e.g., two, three, four, etc.) is detected on the same slide. In yet other embodiments, one or more proximity assays may be multiplexed with a single assay (e.g., a proximity assay for HER2-HER3 dimers multiplexed with ER, PR, Ki-67 proteins or HER2 DISH gene assay).

Figure 3:
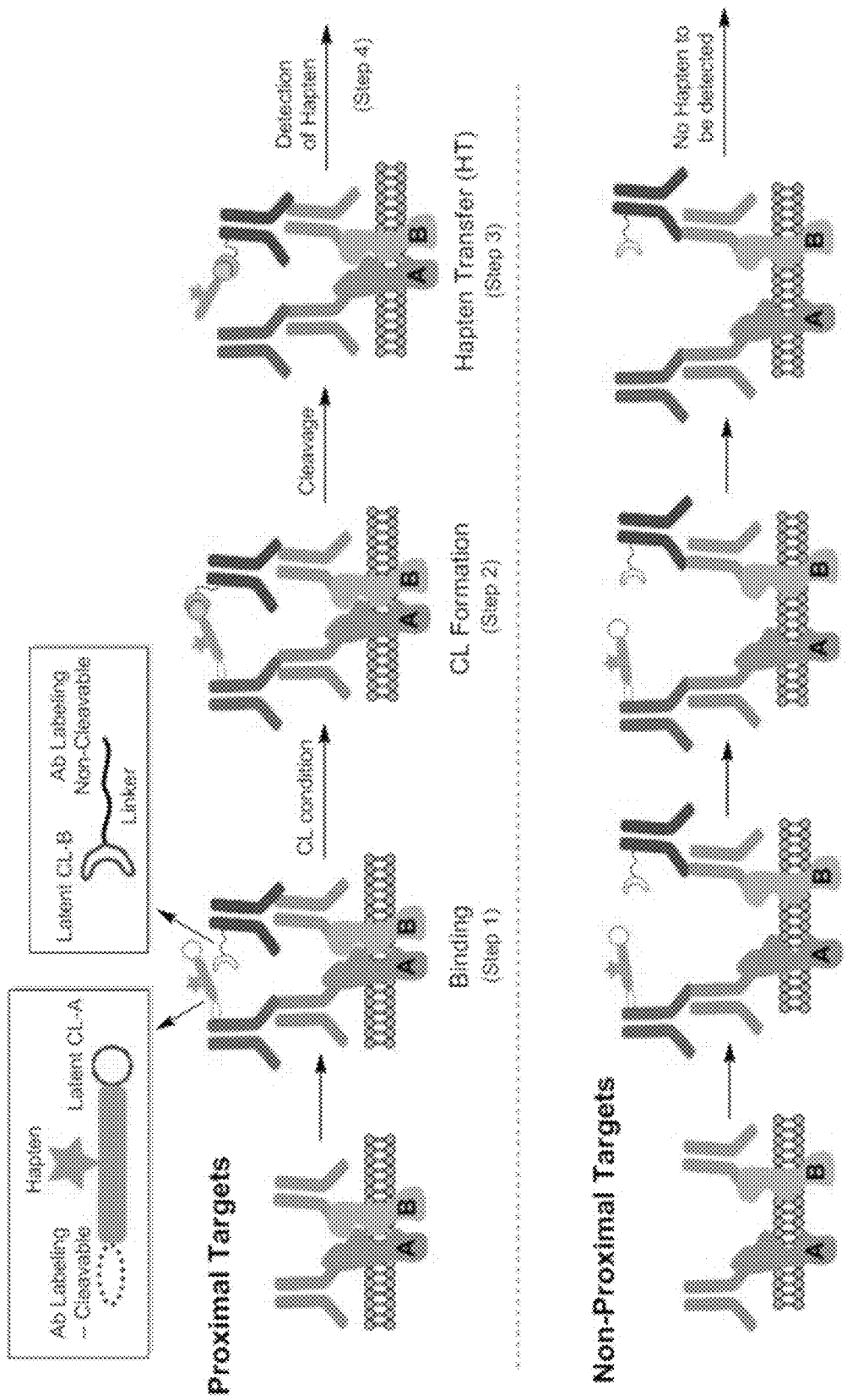
FIG. 3 is a schematic illustration showing the concept and major steps involved in a proximity assay according to the present disclosure. The top portion shows the proximity assay in a system wherein the two targets of interest are in close proximity. The bottom portion shows the proximity assay in a system wherein the two targets of interest are not in close proximity. The present invention is not limited to the components and steps described in FIG. 3.

The methods of the present invention feature the use of specific binding moieties (e.g., antibodies), conjugated with a cleavable bridge component (Conjugate A) as well as other specific binding moieties (e.g., antibodies) conjugated with a non-cleavable bridge component (Conjugate B). The cleavable bridge component comprises a detectable moiety (e.g., hapten), as well as a cleavage site and a chemical ligation group at or near its terminus. The non-cleavable bridge component comprises a chemical ligation group at or near its terminus. FIG. 3 shows exemplary conjugates (Conjugate A, Conjugate B) which specifically recognize and are bound to primary antibodies that are bound to the targets of interest. Alternatively, the conjugates could be bound directly to the targets of interest. For example, the conjugates could be made using primary antibodies. Similarly, the conjugate could be included in a tertiary or quarternary detection stack. Exemplary conjugates could include an anti-species antibody or an anti-hapten antibody. The conjugates are subjected to external stimulation (e.g., a catalyst or other mechanism such as UV light, a deprotection condition, etc.) wherein if the two conjugates (Conjugate A, Conjugate B) are in close proximity, a covalent bond is formed between the two antibody-conjugated bridge components via the chemical ligation groups. Subsequently, the cleavable bridge component is cleaved via the cleavage site, rendering the bonded bridge components attached to only the antibody with the non-cleavable bridge component. Following a washing step, the detectable moiety can be detected via a detection system such as an immunohistochemistry system or fluorescence system (or other appropriate detection system). If the conjugates (Conjugate A, Conjugate B) are not in close proximity, the covalent bond is not formed between the two bridge components; when the cleavage reaction occurs, the cleavable bridge component (with the detectable moiety) is cleaved from the binding moiety and, following the washing step, is not able to be detected via the detection system. Thus, detection of the detectable moiety is indicative of proximity of the two targets of interest.

In some embodiments, detection of the detectable moiety indicates the targets are no more than 40 nm apart. In some embodiments, detection of the detectable moiety indicates the targets are no more than 35 nm apart. In some embodiments, detection of the detectable moiety indicates the targets are no more than 30 nm apart. In some embodiments, detection of the detectable moiety indicates the targets are no more than 25 nm apart. In some embodiments, detection of the detectable moiety indicates the targets are no more than 15 nm apart. In some embodiments, detection of the detectable moiety indicates the targets are no more than 10 nm apart. In some embodiments, detection of the detectable moiety indicates the targets are no more than 5 nm apart. In some embodiments, detection of the detectable moiety indicates the targets are no more than 2 nm apart. One aspect of the present invention is that the distance detectable using the proximity assay can be tailored for a particular set of targets. For example, by varying linker or bridge lengths, by varying the detection stack approach (e.g. conjugate being primary, secondary, tertiary, or a quaternary detection molecule), or by using a hapten-tyramide amplification step within the detection stack, the distance detectable using the methods and reagents herein can be varied as needed for a particular application.

The chemistries used in the present invention (e.g., for covalent bond formation between the two bridge components) are bioorthogonal (e.g., non-perturbing nor perturbed by biological systems). That is, the conditions under which the covalent bonds between the conjugates form are not natural and thus do not occur spontaneously or non-specifically. The present invention is not limited to the chemistries described herein (see other examples of bioorthogonal reactions in Patterson et al., ACS Chemical Biology 2014, 9, 592-605, see also Xiang et al., *Angew. Chem. Int. Ed.* 2014, 53, 2190-2193).

In an illustrative embodiment, a method of detecting a first target located proximally to a second target in a sample includes labelling the first target with a first conjugate comprising a cleavable bridge component, the cleavable bridge component comprises a cleavage site, a detectable moiety, and a first chemical ligation group labelling the second target with a second conjugate comprising a non-cleavable bridge component, the non-cleavable bridge component comprises a second chemical ligation group, activating the first chemical ligation group or the second chemical ligation group so a covalent bond can form where the first target and the second target are proximal; cleaving the detectable moiety from the first target site; washing the sample to remove unbound detectable moiety; and detecting the detectable moiety visible.

Conjugate a and the Cleavable Bridge Component

Figure 1B:
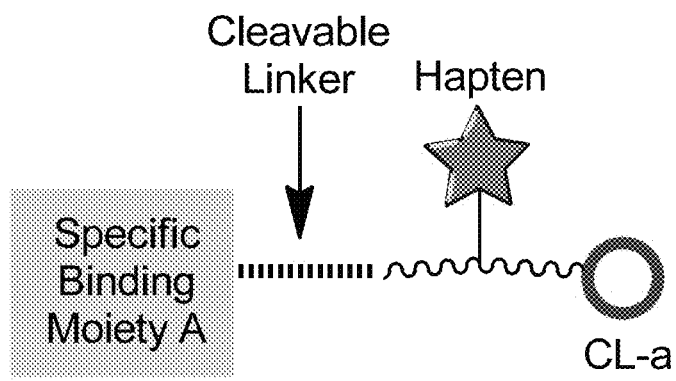
FIG. 1B is an additional depiction of a schematic depiction of a modified specific binding moiety and a cleavable bridge component. The cleavable bridge components comprise a cleavage site (cleavable linker), a detectable moiety (hapten), and a chemical ligation group (CL). The hapten (detectable moiety) and the chemical ligation group can be in a linear or branched arrangement. Linkers can be used among all three functionalities. The cleavable linker is more proximal to the specific binding moiety than the other two groups.

Molecules such as antibodies are modified with at least one cleavable bridge component. FIG. 1A and FIG. 1B show a schematic structure of a cleavable bridge component. The cleavable bridge component comprises a cleavage site, a detectable moiety/hapten, and a chemical ligation group (CL). The cleavage site is positioned to be more proximal to the antibody than is the detectable moiety/hapten or the chemical ligation group. The chemical ligation group is positioned at or near the terminus of the cleavable bridge component.

In some embodiments, the antibody is modified with at least two cleavable bridge components. In some embodiments, the antibody is modified with at least three cleavable bridge components. In some embodiments, the antibody is modified with at least four cleavable bridge components. In some embodiments, the antibody is modified with at least five cleavable bridge components. In some embodiments, the antibody is modified with at least ten (or more) cleavable bridge components.

The chemical ligation group of the cleavable bridge component (as well as the chemical ligation group of the non-cleavable bridge component) is bioorthogonal, e.g., inert, and stable under physiological conditions. However, under appropriate conditions (external stimulation), the chemical ligation groups of the two components readily form a covalent bond.

Typically, upon external stimulation, the chemical ligation group of the cleavable bridge component and the chemical ligation group of the non-cleavable bridge component can form a covalent bond in less than three hours. In some embodiments, upon external stimulation, the chemical ligation groups can form a covalent bond in less than two hours. In some embodiments, upon external stimulation, the chemical ligation groups can form a covalent bond in less than one hour. In some embodiments, upon external stimulation, the chemical ligation groups can form a covalent bond in less than 30 minutes.

Figure 2:
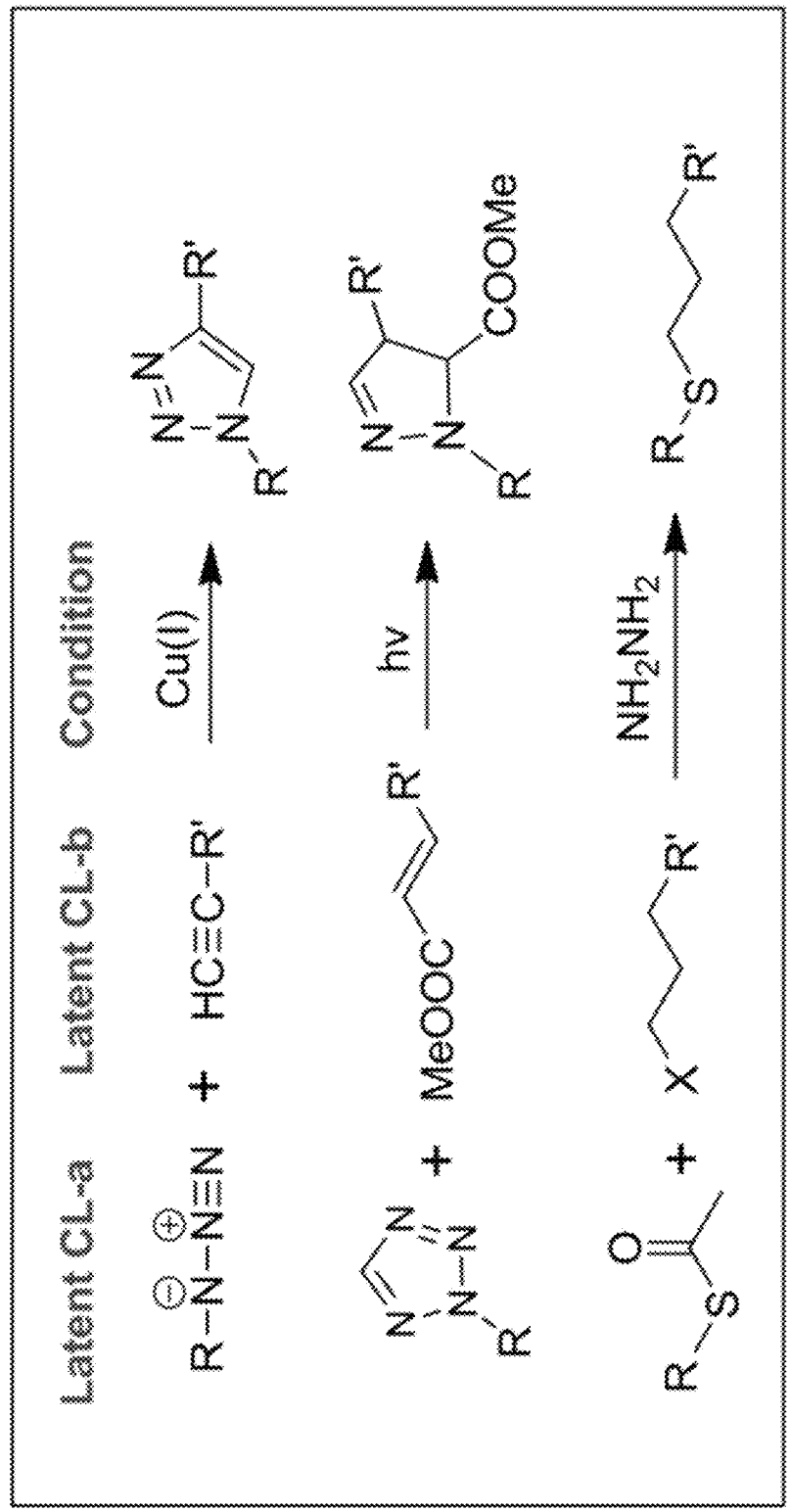
FIG. 2 shows non-limiting exemplary structures of the chemical ligation reactive groups (CL-a and CL-b) and the respective condition for the formation of covalent bond.

Non-limiting examples of chemical ligation groups (CL) are shown in FIG. 2. For example, the chemical ligation group may comprise azide

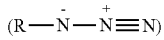

a thioester (see, Formula (I)), a nitrogen-containing (e.g., tetrazole) ring (see, Formula (II)), an alkyne group (RC≡CH), an alkene group (RC=CH$_2$), a halogen group (e.g., —Cl, —Br, —I), or any other appropriate chemical ligation group. FIG. 2 also shows conditions (e.g., Cu(I), light, hydrazine) that may initiate the formation of the covalent bond (shown on the right side of the illustration) between the two latent chemical ligation groups.

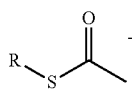
Formula (I)

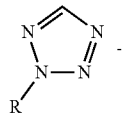
Formula (II)

In other embodiments, the chemical ligation can be enzymatically initiated. For example, a tyramine or quinone methide precursor can be used as the chemical ligation group which interacts with a proximal enzyme to form a reactive species. The reactive species forms a bond with an available reactive moiety (e.g., an amine or thiol group) to form a covalent bond between the tyramine and available reactive groups.

The cleavage site of the cleavable bridge component may comprise any appropriate cleavage site. Commonly known cleavage sites include but are not limited to disulfide bonds, diols, nitrophenyl derivatives, or the like. A disulfide bond cleavage site (S—S) is shown in the schematic drawing of FIG. 4 (top illustration). A disulfide bond cleavage site may be cleaved, for example, by dithiothreitol (DTT), beta-mercaptoethanol (BME), tris(2-carboxyethyl)phosphine (TCEP), the like, or a combination thereof. A diol, specifically a vicinal diol, cleavage site may be cleaved, for example, by (by NaIO$_4$). Similarly, a vicinal hydroxylamine may be similarly cleaved. A nitrophenyl-derivative cleavage site may be cleaved, for example, by ultraviolet irradiation. The present invention is not limited to the aforementioned cleavage sites and cleavage inducers/catalysts.

The detectable moiety (e.g., hapten) may be any appropriate small molecular non-endogenous compound, peptide tag, oligonucleotide, or the like. The molecule shown in FIG. 4 features a detectable moiety comprising a human influenza hemagglutinin (HA-tag) peptide (YPYDVPDYA, SEQ ID NO: 1). Here, the HA peptide also serves as a scaffold to connect the cleavage site (disulfide bond) and the chemical ligation group (azide (N$_3$)), CL-a. The partner antibody is modified with a terminal alkyne group as non-cleavable CL-b to provide Conjugate B.

Other molecules may be used as the detectable moiety. For example, commonly used peptide haptens include FLAG Tag (DYKDDDDK, SEQ ID NO: 2), Myc Tag (EQKLISEEDL, SEQ ID NO: 3), V5 Tag (GKPIPNPLLGLDST, SEQ ID NO: 4), E-Tag (GAPVPYPDPLEPR, SEQ ID NO: 5), and VSV Tag (YTDIEMNRLGK, SEQ ID NO: 6).

Figure 5:
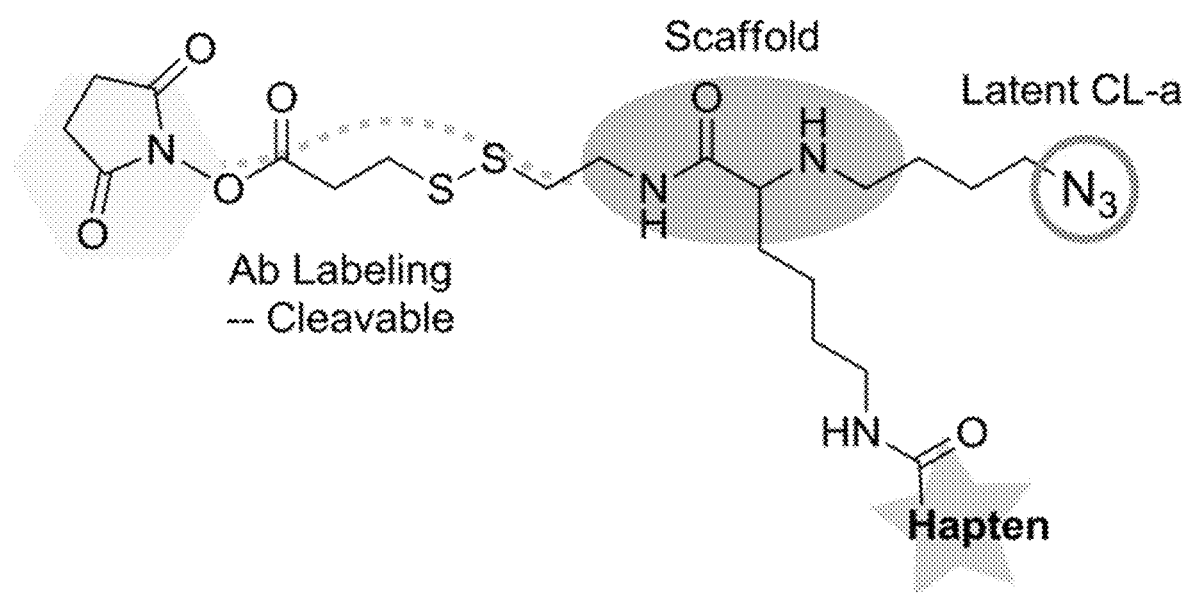
FIG. 5 shows an alternative cleavable bridge component (tri-functional molecule) wherein the cleavable bridge component comprises a scaffold, and the detectable moiety/hapten is bound to the scaffold.
Figure 6:
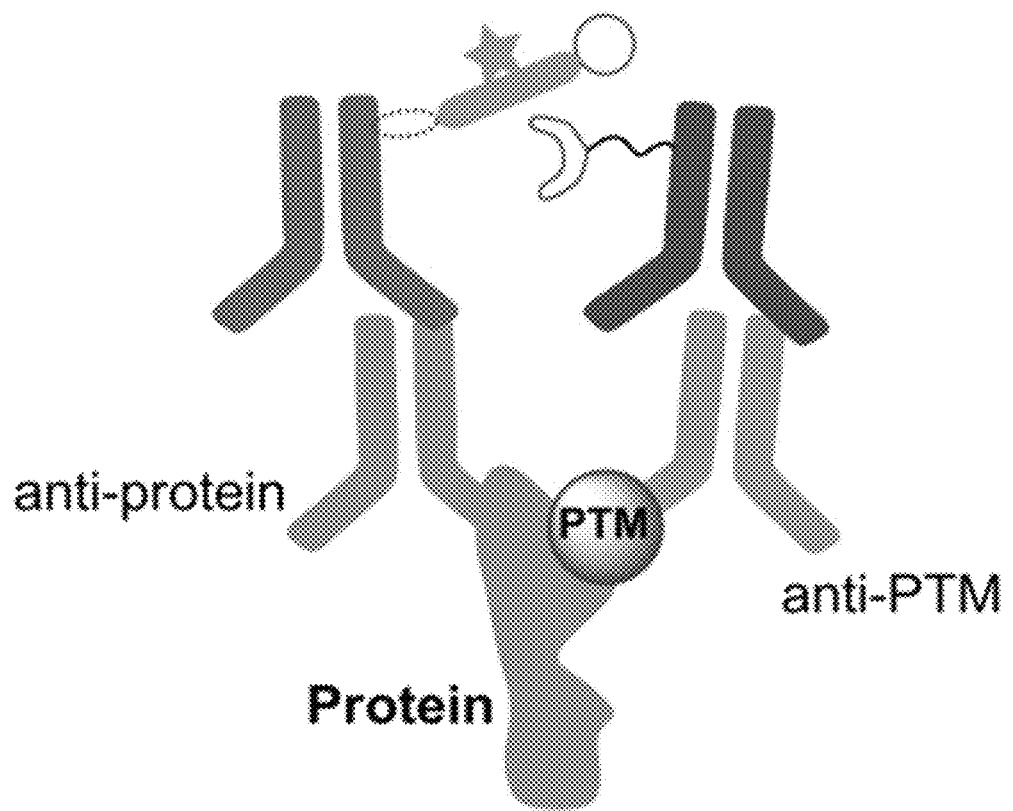
FIG. 6 is a schematic illustration showing the detection of protein post-translational modification (PTM), such as a phosphorylation or ubiquitination using an assay of the present invention.

Without wishing to limit the present invention to any theory or mechanism, peptides may be used as detectable moieties/haptens because they are commercially available and may also serve as a scaffold in the tri-functional molecule. FIG. 5 shows another example of the cleavable bridge component (tri-functional molecule) with lysine as the scaffold.

Figure 7:
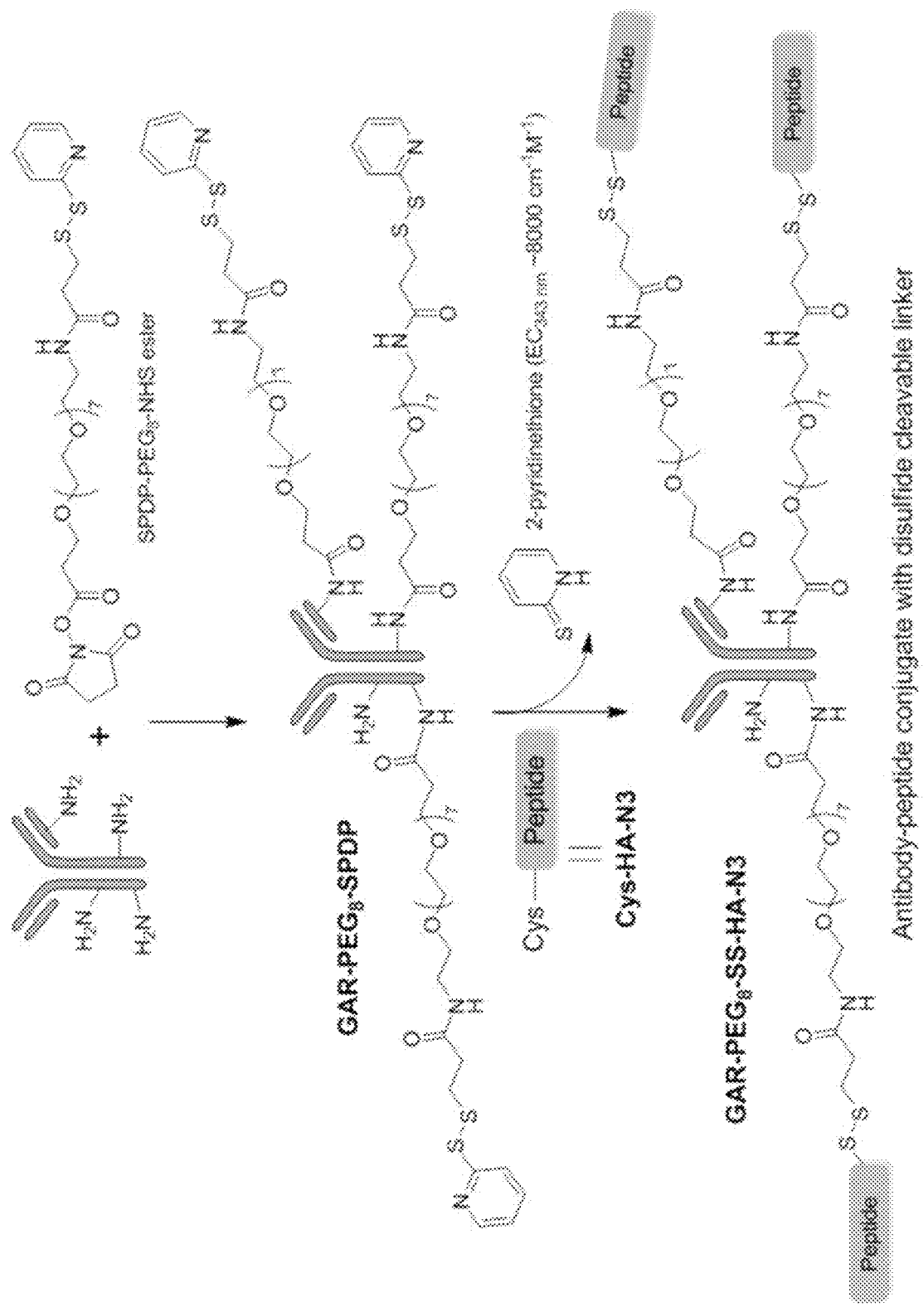
FIG. 7 is a schematic illustration showing the synthesis of Conjugate A of goat anti-rabbit (GAR) with cleavable bridge component comprising a PEG$_8$ linker, a disulfide bond, a hemagglutinin tag (HA-tag) as hapten, and an azide group (N$_3$).

FIG. 7 shows the synthesis of a conjugate (Conjugate A) comprising an antibody and a cleavable bridge component. SPDP-dPEG$_8$-NHS ester (Quanta BioDesign, Ltd., Plain City, Ohio) (see, Formula (III)) was conjugated to a goat-anti-rabbit antibody.

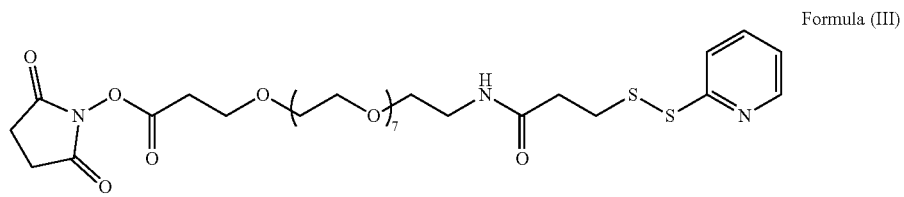
Formula (III)

For example, 20-30 equivalence of SPDP-PEG$_8$-NHS ester was used and the reaction was kept at room temperature for at least 2 hours, and the modified antibody was purified using a ZEBA spin column (Thermo Fisher Scientific Inc., Rockford, Ill.) and eluted with PBS (pH=7.2). The modified antibody was then treated with ~10 equivalence of peptide Cys-HA-N$_3$ (Bio-Synthesis Inc, Lewisville, Tex.) (see, Formula (IV)), which comprises a hemagglutinin (HA) detectable moiety and an azide chemical ligation group, and incubated at room temperature overnight.

Formula (IV)

H-Gly-Tyr-Pro-Tyr-Asp-Val-Pro-Asp-Tyr-Ala-Ser-Gly-Cys-OH

Figure 8:
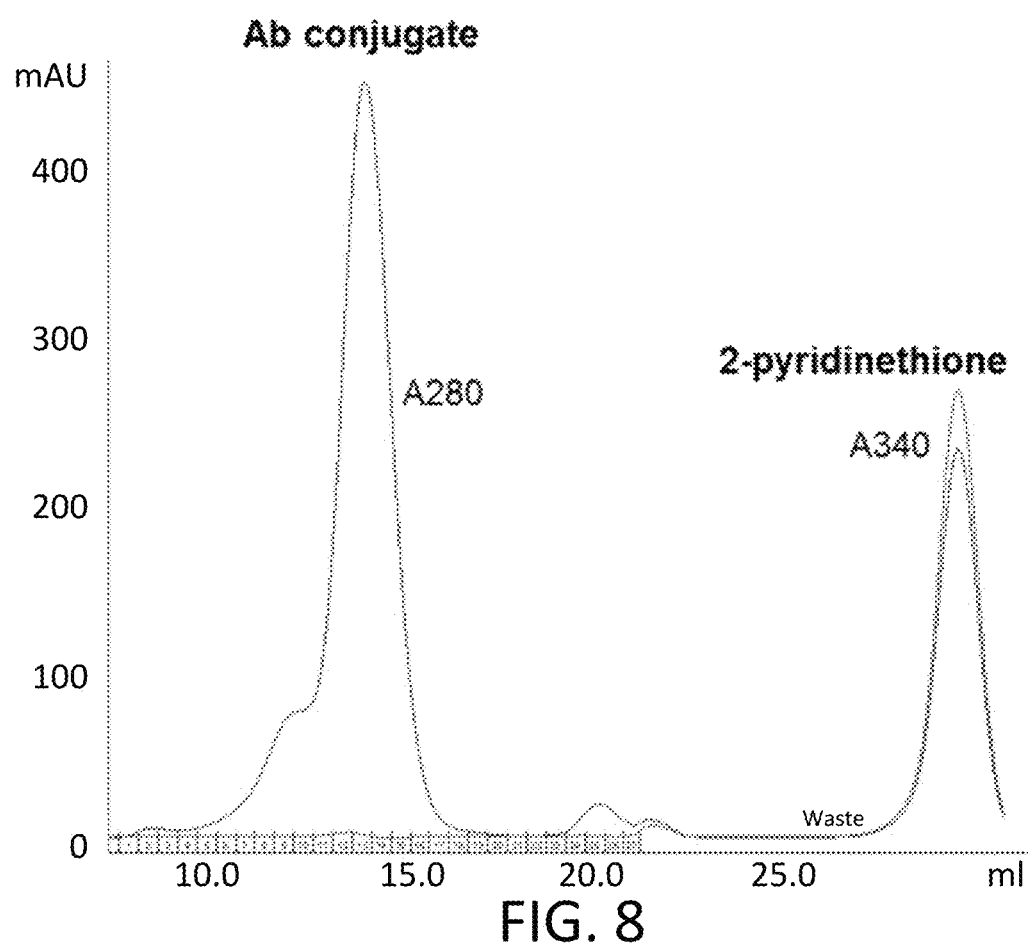
FIG. 8 is a representative SEC chromatogram showing the purification of the GAR-HA peptide conjugate of FIG. 7.
Figure 9:
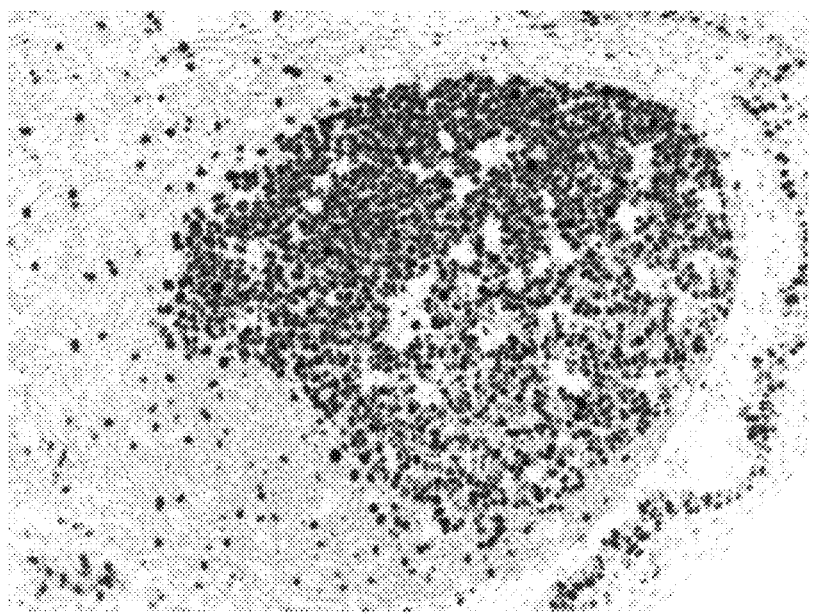
FIG. 9 is a photomicrograph showing detection of the detectable moiety/hapten HA-tag using IHC methods using a commercially available DAB chromogenic detection system.

The final conjugate GAR-PEG$_8$SS-HA-N$_3$ (Conjugate A) was purified by size exclusion chromatography using Superdex 200 10/300 GL column on an AKTA purifier (GE Healthcare Bio-Sciences, Pittsburgh, Pa.) and eluted with PBS (0.1 M, pH=7.2). A typical chromatogram is shown in FIG. 8. The peak at the end of the elution indicates the presence of 2-pyridinethione ($E_{343\ nm}$~8000 cm$^{-1}$M$^{-1}$) as a result of the Cys-peptide conjugation to SPDP labeled antibody. This Conjugate A of FIG. 7 comprises a disulfide cleavable bond, a HA-tag detectable moiety, and an azide chemical ligation group.

There are various ways to construct the modified specific binding molecules (Conjugates A, B), and the present invention is not limited to those described herein. In some embodiments, the cleavable linker (cleavage site) is formed upon conjugation of a peptide to the antibody (see FIG. 7 wherein the peptide is conjugated to the SPDP-modified antibody). Alternatively, antibodies can be directly modified with a molecule already contains all three functionalities (cleavable linker/cleavage site, chemical ligation group, detectable moiety) (e.g., see FIG. 5). One or ordinary skill in the art may use alternative synthesis mechanism wherein the functionalities are added to the molecule at various or simultaneous stages.

Conjugate B and the Non-Cleavable Bridge Component

Figure 1C:
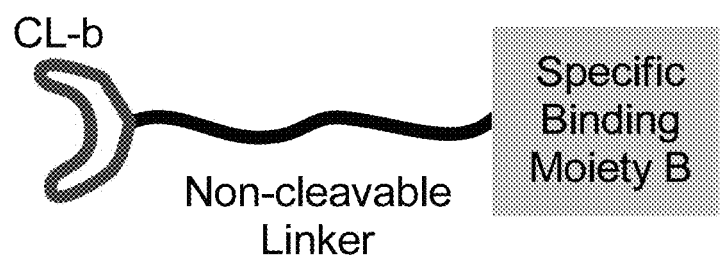
FIG. 1C shows a depiction of a specific binding moiety (e.g., antibody) and a non-cleavable bridge component. The cleavable bridge component comprises a linker and a chemical ligation group (CL).

Molecules such as antibodies are modified with a non-cleavable bridge component. FIG. 1C shows a schematic structure of a non-cleavable bridge component (a tri-functional molecule). The non-cleavable bridge component comprises a chemical ligation group (CL) at or near its terminus.

In some embodiments, the antibody is modified with at least two non-cleavable bridge components. In some embodiments, the antibody is modified with at least three non-cleavable bridge components. In some embodiments, the antibody is modified with at least four non-cleavable bridge components. In some embodiments, the antibody is modified with at least five non-cleavable bridge components. In some embodiments, the antibody is modified with at least ten (or more) non-cleavable bridge components.

As previously discussed, the chemical ligation group of the non-cleavable bridge component (as well as the chemical ligation group of the cleavable bridge component) is bioorthogonal, e.g., inert, and stable under physiological conditions. However, under appropriate conditions (external stimulation), the chemical ligation groups of the two bridge components readily form a covalent bond.

As previously discussed, non-limiting examples of chemical ligation groups (CL) are shown in FIG. 2. For example, the chemical ligation group may comprise azide $$(R-\overset{-}{N}-\overset{+}{N}\equiv N)$$

a thioester (see above, Formula (I)), a tetrazole ring (see above, Formula (II)), an alkyne group $$(RC\equiv CH),$$

a halogen group (—Cl, —Br, —I), an alkene group (RC=CH$_2$), or any other appropriate chemical ligation group. FIG. 2 also shows conditions (e.g., Cu(I), light, hydrazine) that may initiate the formation of the covalent bond (shown on the right side of the illustration) between the two latent chemical ligation groups. The example in FIG. 4 (bottom illustration) shows an antibody modified with a non-cleavable linkage component comprising a terminal alkyne group as the chemical ligation group (CL-b).

A non-limiting example of synthesis of a Conjugate B (comprising an antibody and a non-cleavable bridge component) is described herein: Goat-anti-mouse (GAM) or Goat-anti-rabbit (GAR) in PBS is treated with 15 to 30 equivalence of alkyne-PEG$_4$-NHS ester (Click Chemistry Tools, Scottsdale, Ariz.) (see, Formula (V)) and incubated at room temperature for at least two hours.

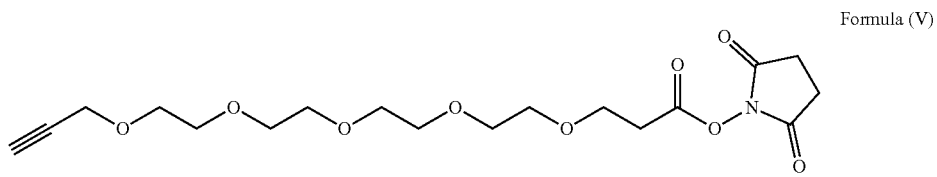 [SMILES: C#CCOCCOCCOCCOCCOCCC(=O)ON1C(=O)CCC1=O]

Formula (V)

The modified antibody is purified using a ZEBA spin column, eluted in PBS (0.1 M, pH=7.2) to provide GAM-PEG4-CCH or GAR-PEG4-CCH.

Figure 4:
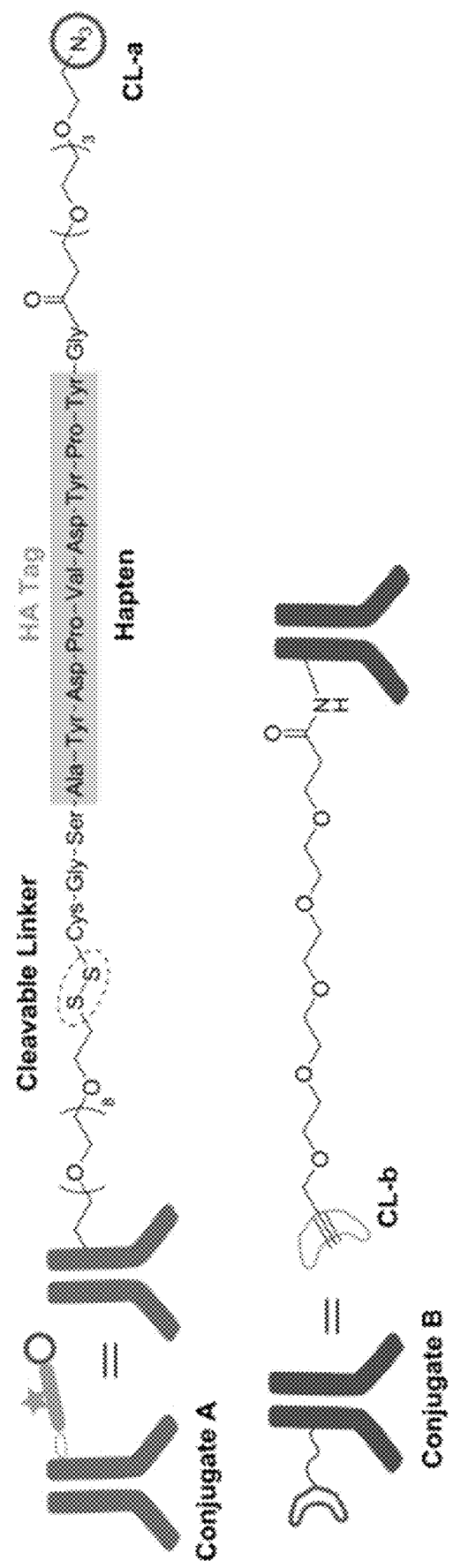
FIG. 4 is a schematic depiction showing a non-limiting example of an antibody conjugate comprising an antibody with a cleavable bridge components (top illustration) and a non-limiting example of an antibody conjugate comprising a non-cleavable bridge component (bottom illustration).

As previously discussed, any appropriate external stimulation may be provided to achieve a covalent bond between the chemical ligation groups of the conjugates. For example, in some embodiments, the conjugates shown in FIG. 4 are treated with copper (I), which catalyzes a Huisgen 1,3-dipolar cycloaddition of alkynes to azides to form 1,4-disubsituted-1,2,3-triazoles. In some embodiments, a ligand is used in the reaction involving Cu(I). One example is Tris(3-hydroxypropyltriazolylmethyl)amine (THPTA) (Sigma-Aldrich or Click Chemistry Tools) (see, Formula (VI)).

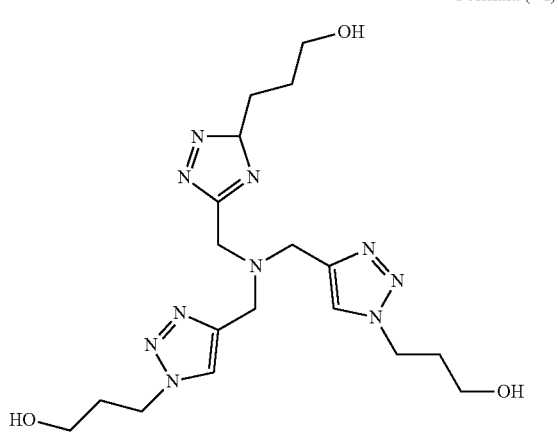

Formula (VI)

The antibodies of the present invention are selected to as not to bind to each other or aggregate with each other so as to prevent background signals.

Without wishing to limit the present invention to any theory or mechanism, the design of the cleavable linker allows for the separation of the two major steps of the assay: the chemical ligation group is stable under physiological conditions and reacts with the partner chemical ligation group of the non-cleavable linker only upon appropriate external stimulation. And, the cleavage site allows for the cleavage of the cleavable linker during a subsequent and separate step.

Detectable Moieties

While not exhaustive, WO2012024185, which is incorporated in its entirety herein by reference, provides disclosure concerning presently available chromogens and haptens. Embodiments of detectable labels include haptens, such as pyrazoles, particularly nitropyrazoles; nitrophenyl compounds; benzofurazans; triterpenes; ureas and thioureas, particularly phenyl ureas, and even more particularly phenyl thioureas; rotenone and rotenone derivatives, also referred to herein as rotenoids; oxazole and thiazoles, particularly oxazole and thiazole sulfonamides; coumarin and coumarin derivatives; cyclolignans, exemplified by Podophyllotoxin and Podophyllotoxin derivatives; and combinations thereof. Embodiments of haptens and methods for their preparation and use are disclosed in U.S. Pat. No. 7,695,929, which is incorporated in its entirety herein by reference.

Exemplary haptens include, but are not limited to, BD (benzodiazepine), BF (benzofurazan), DABSYL (4-(dimethylamino)azobenzene-4'-sulfonamide), DCC (7-(diethylamino)coumarin-3-carboxylic acid), DIG (digoxigenin), DNP (dinitrophenyl), HQ (3-hydroxy-2-quinoxalinecarbamide) NCA (nitrocinnamic acid), NP (nitropyrazole), PPT (Podophyllotoxin), Rhod (rhodamine), ROT (rotenone), and TS (thiazolesulfonamide). Other suitable haptens include biotin and fluorescein derivatives (FITC (fluorescein isothiocyanate), TAMRA (tetramethylrhodamine), Texas Red, etc.).

Suitable chromophores include coumarin and coumarin derivatives. Exemplary coumarin-based chromophores include DCC and 2,3,6,7-tetrahydro-11-oxo-1H,5H,11H-[1]benzopyrano[6,7,8-ij]quinolizine-10-carboxylic acid. Another class of chromogenic moieties suitable for use includes diazo-containing chromogens, such as DABSYL, which has a $\lambda_{max}$ of about 436 nm, and tartrazine, which has a $\lambda_{max}$ of about 427 nm.

In yet other embodiments, the chromophore may be a triarylmethane compound. Exemplary triarylmethane chromophores are provided below:

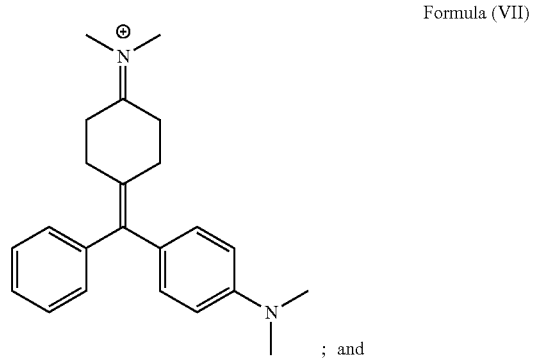

Formula (VII)

; and

Formula (VIII)

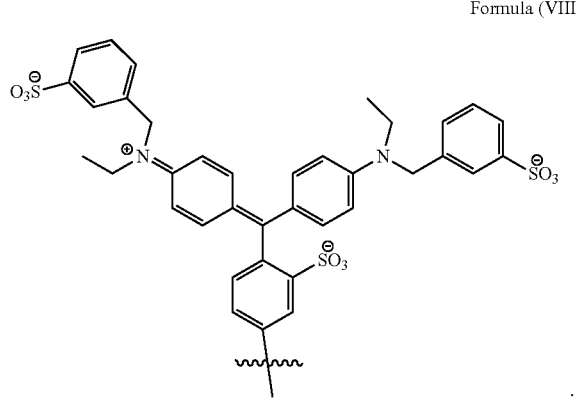

Exemplary annulated chromophores include, but are not limited to:

Formula (IX)

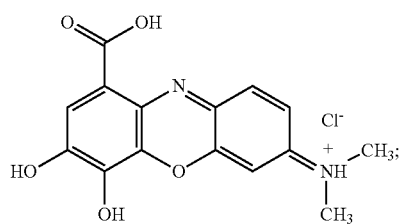

Formula (X)

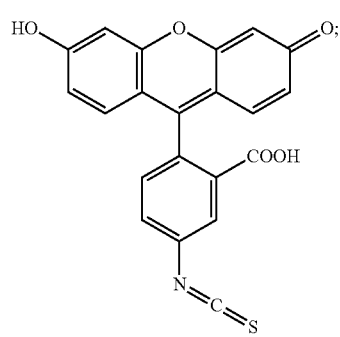

Formula (X)

Formula (XI)

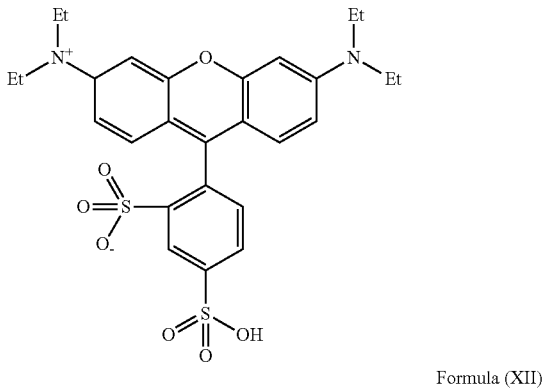

Formula (XII)

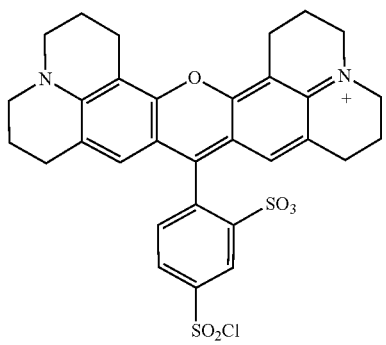

Formula (XIII)

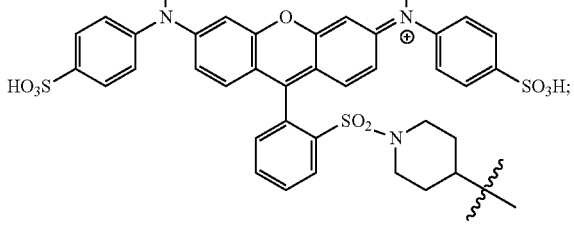

Formula (XIV)

other rhodamine derivatives, such as tetramethylrhodamines (including TMR, TAMRA, and reactive isothiocyanate derivatives), and diarylrhodamine derivatives, such as the QSY 7, QSY 9, and QSY 21 dyes.

Other exemplary detectable labels include resorufin, DAB; AEC; CN; BCIP/NBT; fast red; fast blue; fuchsin; NBT; ALK GOLD; Cascade Blue acetyl azide; Dapoxylsulfonic acid/carboxylic acid succinimidyl ester; DY-405; Alexa Fluor 405 succinimidyl ester; Cascade Yellow succinimidyl ester; pyridyloxazole succinimidyl ester (PyMPO); Pacific Blue succinimidyl ester; DY-415; 7-hydroxycoumarin-3-carboxylic acid succinimidyl ester; DYQ- 425; 6-FAM phosphoramidite; Lucifer Yellow; iodoacetamide; Alexa Fluor 430 succinimidyl ester; Dabcyl succinimidyl ester; NBD chloride/fluoride; QSY 35 succinimidyl ester; DY-485XL; Cy2 succinimidyl ester; DY-490; Oregon Green 488 carboxylic acid succinimidyl ester; Alexa Fluor 488 succinimidyl ester; BODIPY 493/503 C3 succinimidyl ester; DY-480XL; BODIPY FL C3 succinimidyl ester; BODIPY FL C5 succinimidyl ester; BODIPY FL-X succinimidyl ester; DYQ-505; Oregon Green 514 carboxylic acid succinimidyl ester; DY-510XL; DY-481XL; 6-carboxy-4',5'-dichloro-2',7'-dimethoxyfluorescein succinimidyl ester (JOE); DY-520XL; DY-521XL; BODIPY R6G C3 succinimidyl ester; erythrosin isothiocyanate; 5-carboxy-2',4',5',7'-tetrabromosulfonefluorescein succinimidyl ester; Alexa Fluor 532 succinimidyl ester; 6-carboxy-2',4,4',5'7,7'-hexachlorofluorescein succinimidyl ester (HEX); BODIPY 530/550 C3 succinimidyl ester; DY-530; BODIPY TMR-X succinimidyl ester; DY-555; DYQ-1; DY-556; Cy3 succinimidyl ester; DY-547; DY-549; DY-550; Alexa Fluor 555 succinimidyl ester; Alexa Fluor 546 succinimidyl ester; DY-548; BODIPY 558/568 C3 succinimidyl ester; Rhodamine red-X succinimidyl ester; QSY 7 succinimidyl ester; BODIPY 564/570 C3 succinimidyl ester; BODIPY 576/589 C3 succinimidyl ester; carboxy-X-rhodamine (ROX); succinimidyl ester; Alexa Fluor 568 succinimidyl ester; DY-590; BODIPY 581/591 C3 succinimidyl ester; DY-591; BODIPY TR-X succinimidyl ester; Alexa Fluor 594 succinimidyl ester; DY-594; carboxynaphthofluorescein succinimidyl ester; DY-605; DY-610; Alexa Fluor 610 succinimidyl ester; DY-615; BODIPY 630/650-X succinimidyl ester; erioglaucine; Alexa Fluor 633 succinimidyl ester; Alexa Fluor 635 succinimidyl ester; DY-634; DY-630; DY-631; DY-632; DY-633; DYQ-2; DY-636; BODIPY 650/665-X succinimidyl ester; DY-635; Cy5 succinimidyl ester; Alexa Fluor 647 succinimidyl ester; DY-647; DY-648; DY-650; DY-654; DY-652; DY-649; DY-651; DYQ-660; DYQ-661; Alexa Fluor 660 succinimidyl ester; Cy5.5 succinimidyl ester; DY-677; DY-675; DY-676; DY-678; Alexa Fluor 680 succinimidyl ester; DY-679; DY-680; DY-682; DY-681; DYQ-3; DYQ-700; Alexa Fluor 700 succinimidyl ester; DY-703; DY-701; DY-704; DY-700; DY-730; DY-731; DY-732; DY-734; DY-750; Cy7 succinimidyl ester; DY-749; DYQ-4; and Cy7.5 succinimidyl ester.

Example 1

Example 1 describes non-limiting examples of antibodies used in assays of the present invention.

Reagent anti-HA antibody: Mouse monoclonal Anti-HA-Biotin antibody (clone HA-7) from Sigma-Aldrich (B9183-100UG)

Primary Antibodies used in the proximity assay: anti-E-cadherin rabbit monoclonal antibody, clone EP700Y (Ventana 760-4440), anti-E-cadherin mouse monoclonal antibody clone 36 (Ventana 790-4497), anti-beta-catenin mouse monoclonal antibody clone 14 (Ventana 760-4242), anti-p120 catenin mouse monoclonal antibody clone 98 (Ventana 790-4517), anti-HER-2/neu rabbit monoclonal antibody clone 4B5 (Ventana 790-2991), anti-PR rabbit monoclonal antibody clone 1E2 (Ventana 790-2223), anti-CD21 rabbit monoclonal antibody clone EP3093 (Ventana 760-4438), anti-CD21 mouse monoclonal antibody clone 2G9 (Ventana 760-4245), anti-PMS2 rabbit mAb clone EPR3947 (Ventana 760-4531), anti-MLH1 mouse mAb clone M1 (Ventana 790-4535), anti-CD19 mouse monoclonal antibody clone LE-CD19 (GeneTex, Inc. Irvine, Calif.), anti-phospho-Tyrosine mouse mAb clone P-Tyr-100 and anti-ubiquitin mouse mAb clone P4D1 (Cell Signaling Technology, Inc., Danvers, Mass.).

Example 2

Example 2 describes the detection of the presence of the HA peptide as detectable moiety/hapten in the molecule in FIG. 7 (GAR-PEG$_8$-SS-HA-N$_3$) using IHC. Detection of Ki67 in tonsil tissue was demonstrated by using anti-Ki-67 (30-9) rabbit monoclonal antibody (Ventana 790-4286) as the primary antibody and GAR-PEG$_8$-SS-HA-N$_3$ as the secondary antibody, followed by xHA-biotin, SA-HRP and DAB staining (see FIG. 9) Strong and specific staining of the target is achieved and therefore confirming the presence of the HA-tag as a hapten in the GAR conjugate.

Example 3

Figure 11:
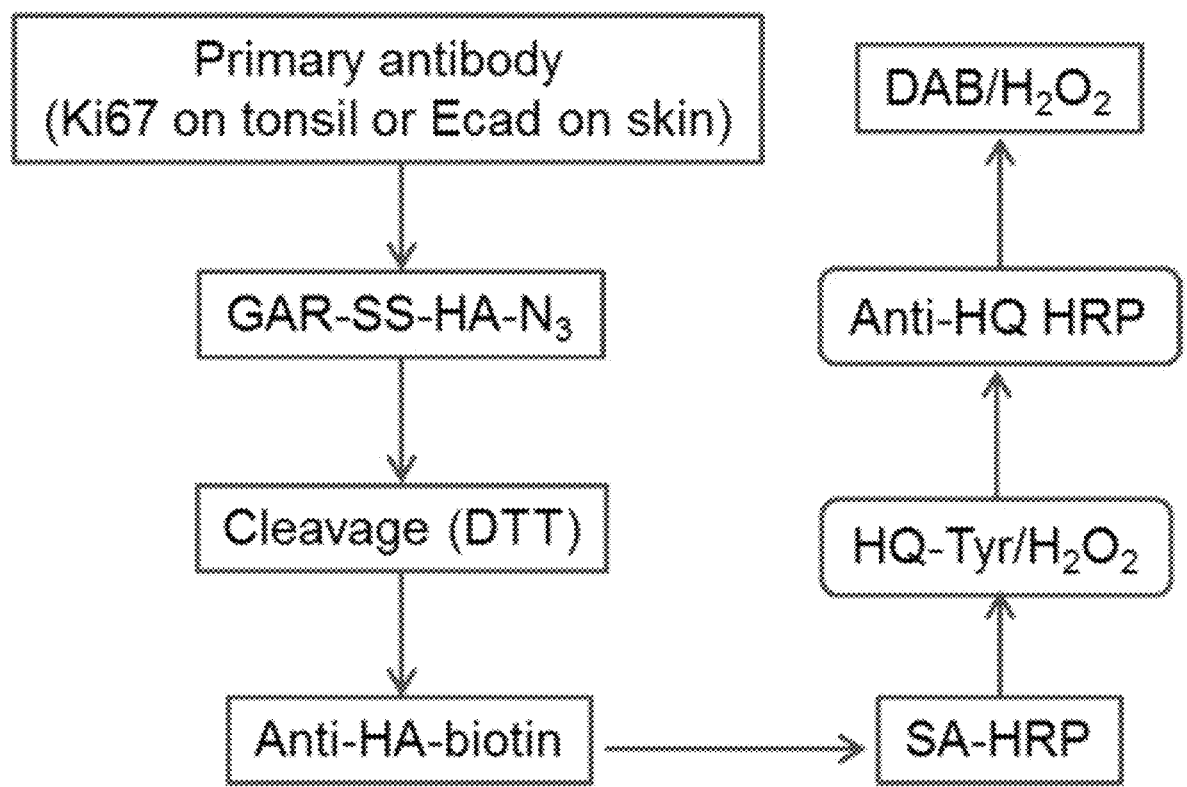
FIG. 11 is a flow chart showing steps used for determining conditions for complete cleavage of HA-tag from Conjugate A (see Example 3).
Figure 12A:
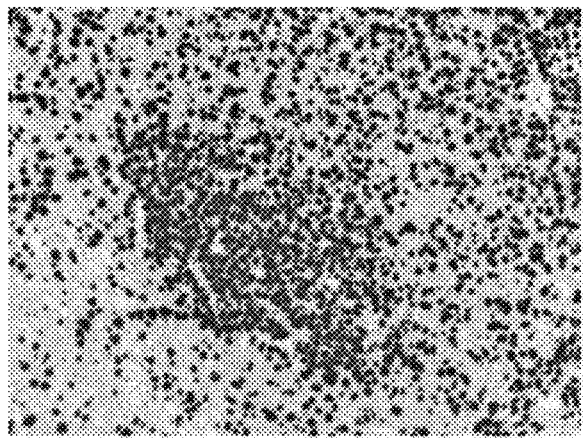
FIG. 12A is a photomicrograph showing stained tonsil tissue slides following assays for Ki67 using various concentrations of dithiothreitol (DDT), no DTT, as described in Example 3, which was performed to establish concentrations of DTT sufficient for in situ cleavage.
Figure 12B:
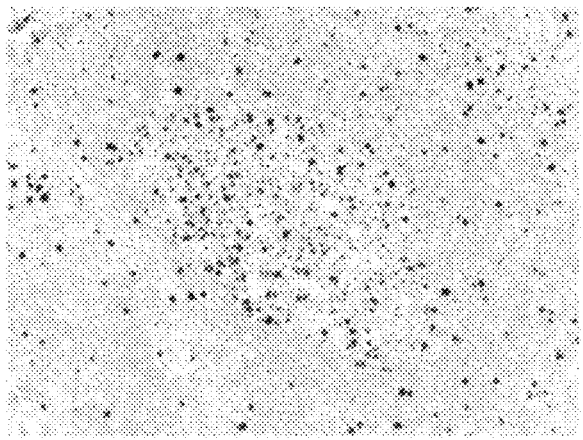
FIG. 12B is a photomicrograph showing stained tonsil tissue slides following assays for Ki67 using various concentrations of dithiothreitol (DDT), 50 mM DTT as described in Example 3, which was performed to establish concentrations of DTT sufficient for in situ cleavage.
Figure 12C:
FIG. 12C is a photomicrographs showing stained tonsil tissue slides following assays for Ki67 using various concentrations of dithiothreitol (DDT), 75 mM DTT, as described in Example 3, which was performed to establish concentrations of DTT sufficient for in situ cleavage.
Figure 12D:
FIG. 12D is a photomicrographs showing stained tonsil tissue slides following assays for Ki67 using various concentrations of dithiothreitol (DDT), 100 mM DTT (24 min DTT incubation, hapten-tyramide amplification (HQ-Tyr AMP) used), as described in Example 3, which was performed to establish concentrations of DTT sufficient for in situ cleavage.

Example 3 describes experiments for determining conditions for complete HA tag cleavage from tissue:

Since the read-out of the proximity assay is, in this specific example, based on the detection of HA tag as a hapten, the ability to completely cleave the HA-tag from antibody bound to non-proximity proteins is important to the overall success of the assay. Residual un-cleaved HA tag may generate background signal. This could be a significant issue for low expressing proximity events or when an amplification scheme is adopted. According to this example, disulfide is used as the cleavable linker and thus is cleaved using a reducing agent (e.g., DTT or TCEP). To determine the conditions sufficient to achieve complete cleavage, detection of known abundant targets such as Ki67 in tonsil and E-cadherin in skin combined with tyramide-hapten (e.g., HQ) amplification were examined. Where complete cleavage was achieved (no staining after cleavage), the conditions were identified as sufficient. Because the conjugate structure was not modified, these conditions were understood to be applicable for most assays using this particular conjugate. FIG. 11 shows the scheme used to determine conditions for complete cleavage.

Figure 13A:
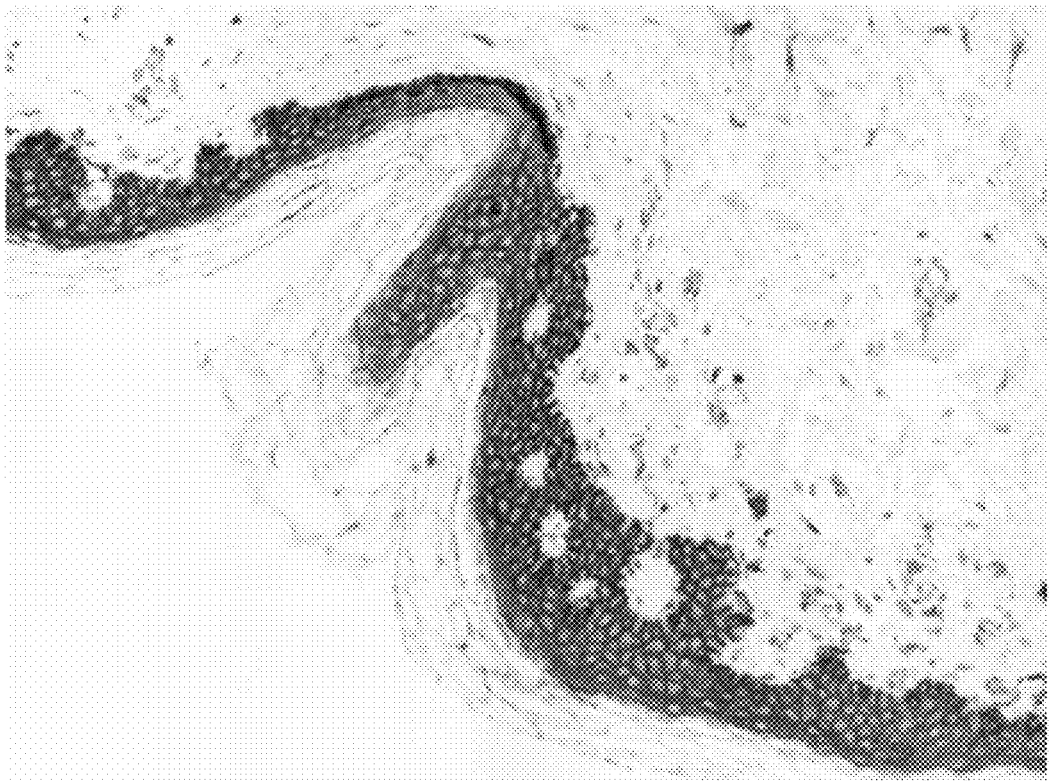
FIG. 13A is a photomicrograph showing stained skin tissue sections for which assays for E-cadherein (E-cad) have been performed using a cleavable bridge component showing no DTT, as described in Example 3.
Figure 13B:
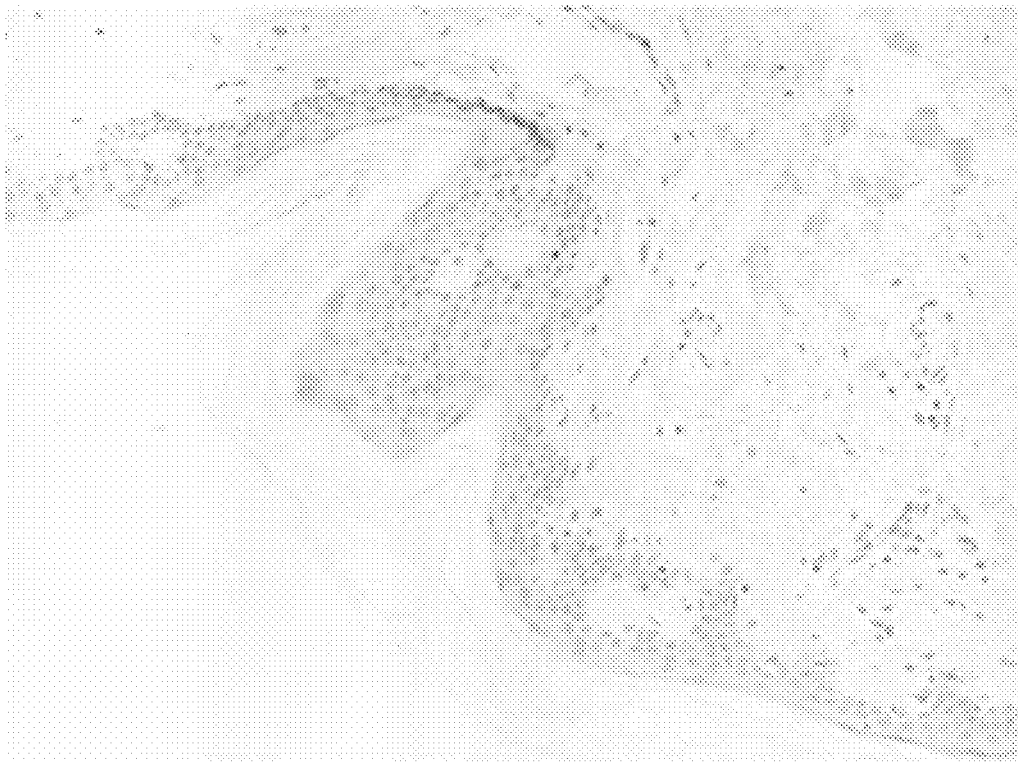
FIG. 13B is a photomicrographs showing stained skin tissue sections for which assays for E-cadherein (E-cad) have been performed using a cleavable bridge component showing 50 mM DTT (24 min DTT incubation, hapten-tyramide amplification (HQ-Tyr AMP) used) (FIG. 13B), as described in Example 3.
Figure 15A:
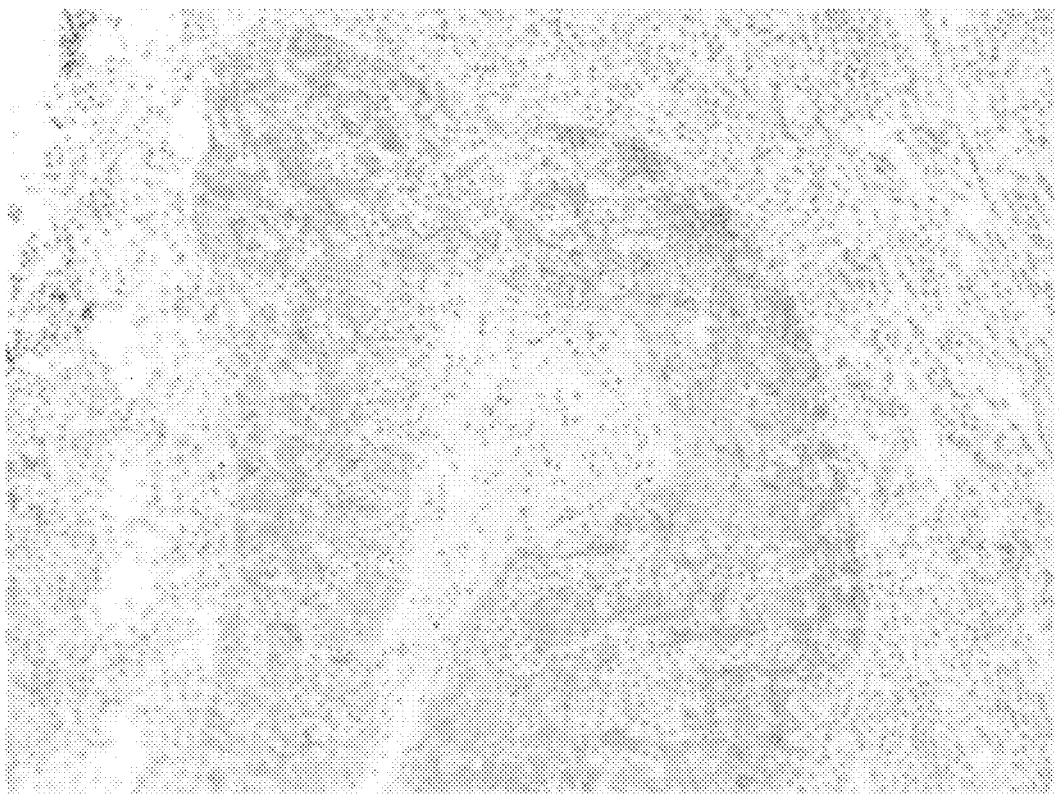
FIG. 15A is a photomicrograph showing detection of E-cadherin(E-cad)/β-catenin(β-cat) in normal tonsil tissue sections using commercial DAB chromogenic detection with Cu(I).
Figure 15B:
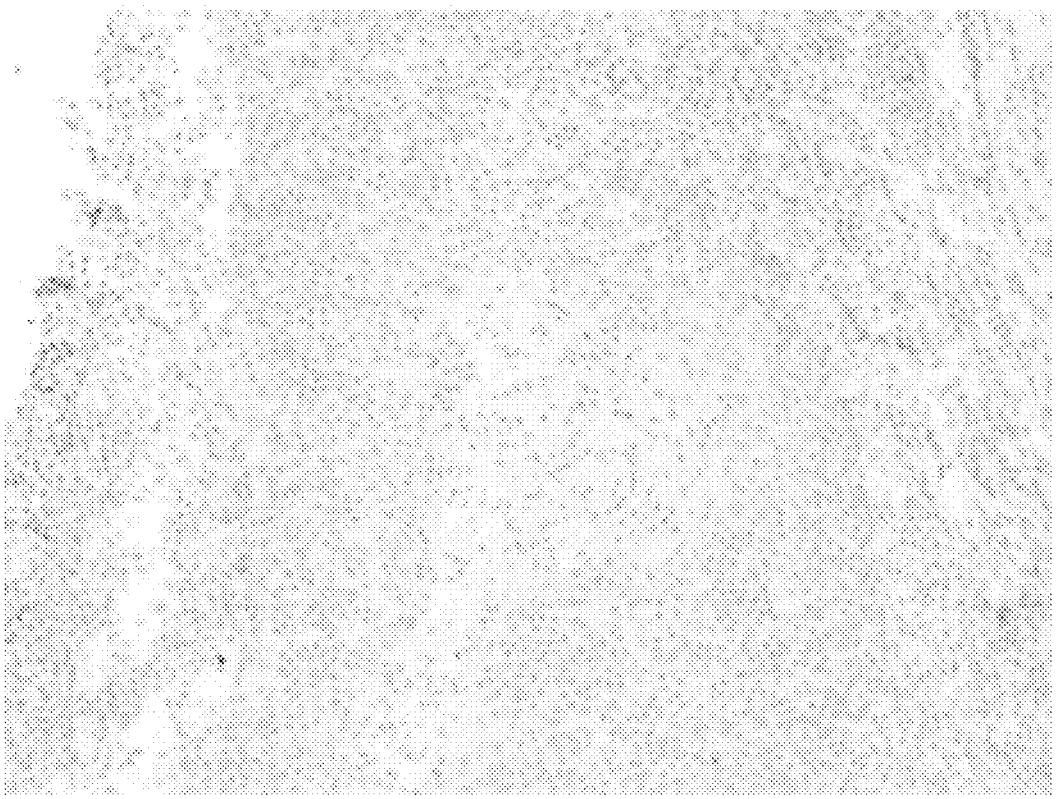
FIG. 15B is a photomicrograph showing detection of E-cadherin(E-cad)/β-catenin(β-cat) in normal tonsil tissue sections using commercial DAB chromogenic detection without Cu(I).

As shown in FIG. 12A-FIG. 12D and in FIG. 13A and FIG. 13B, the cleavage is complete upon treatment with 75 mM DTT for Ki-67 and 50 mM DTT for E-cadherin (the DTT concentration is the 100 uL solution added to each slide, not the effective concentration on tissue, which is usually ⅓ or ¼ of the added concentration). Therefore, 20 to 25 mM DTT effective concentration with 24-minute incubation time is determined to be sufficient for the current assay format.

Example 4

The Validation of the Presence of Acetylene Group in GAM-PEG4-CCH

Referring now to FIG. 14, the presence of reactive acetylene group in the conjugate of GAM-PEG$_4$-CCH was demonstrated by performing an in situ click reaction with biotin-PEG$_7$-N$_3$ (Quanta Biodesign). Specifically, FFPE tonsil sections were first deparaffinization with EZ Prep solution (Ventana) and washed with reaction buffer. Mouse-anti-CD20 primary antibody (clone L26, Ventana 760-2531) was added to the section and incubated at 37° C. for 16 minutes. After washing with reaction buffer, 100 μL of 10 μg/ml GAM-PEG$_4$-CCH was added and incubated at 37° C. for 16 minutes followed by through wash. To the section was then added 100 µL of 1 mM biotin-PEG$_7$-N$_3$, 0.6 mM CuSO$_4$, 20 mM sodium ascorbate with two different ligand (THPTA) concentrations. After incubation at room temperature for 32 minutes, the slides were thoroughly washed. Detection of the biotin was achieved by using SA-HRP and DAB chromogen. As shown in the following figures, specific detection of CD20 was achieved only when Cu was added. No staining at all when Cu was omitted. The result strongly indicated the presence of reactive acetylene functionality in GAM conjugate. FIG. 14A-FIG. 14C are photomicrographs showing detection of CD20 in tonsil sections showing the effect of Cu(I)/L ratio and the attendant staining. FIG. 14A shows a Cu(I)/L ratio of 1:5, FIG. 14B shows a Cu(I)/L ratio of 1:3, and FIG. 14C shows a control with no Cu(I) added. A reactive acetylene group in the conjugate of GAM-PEG$_4$-CCH was used (see Example 3). Specific detection of CD20 was achieved when Cu(I) was added. No staining was observable when Cu was omitted. This indicates the presence of reactive acetylene functionality in GAM conjugate.

Example 5

Example 5 describes experiments using the methods of the present invention.
Experimental Procedures for the Proximity Assay
All antibodies, not explicitly described as sourced elsewhere, and IHC reagents were from Ventana Medical Systems, Inc. (Tucson, Ariz.; "Ventana") unless otherwise specified. IHC staining was performed on a VENTANA BenchMark XT automated slide-processing system (Ventana). For all IHC staining, FFPE sections were first deparaffinization with EZ Prep solution (Ventana) and washed with reaction buffer. Antigen retrieval was carried out in Cell Conditioning 1 (Ventana) (100° C.; 92 minutes) and again washed with 1× reaction buffer (Ventana). Primary antibodies against the targets of interested were applied to the slide and incubated at 37° C. for 32 minutes (see Results for the antibody pairs tested). After thorough wash with reaction buffer, secondary antibody conjugates of GAR-PEG$_8$-SS-HA-N$_3$ and GAM-PEG$_4$-CCH (100 µL of 10 µg/mL each) were added to slides and incubated at 37° C. for 32 minutes. The slides were washed in reaction buffer and water before a drop of 100 µL of HEPES buffer (0.15 M, pH 7.4) was added to the slides. To initiate the azide-acetylene click reaction, 100 µL of Cu(I) catalyst solution was added onto the slide. One working example of the Cu(I) solution contained 0.6 mM CuSO$_4$, 3 mM THPTA, 10 mM HEPES (pH=7.4), 40% DMSO (v/v) and 4 mM of sodium ascorbate (freshly made and added to CuSO$_4$ immediately before adding to slide). The click reaction was allowed to proceed for 32 minutes and the slides were washed thoroughly in reaction buffer. Next, 100 µL of 50-75 mM DTT (dithiothreitol) or TCEP (tris(2-carboxyethyl)phosphine) solution (Sigma-Aldrich) was added to the slides and incubated for 24 minutes. The concentration of the DTT or TCEP solution is dependent on the abundance of the target. Highly expressed targets required higher DTT or TCEP concentration to ensure complete cleavage of the disulfide bond in GAR-PEG$_8$-SS-HA-N$_3$. After washing, the presence of HA tag as a result of proximity induced hapten transfer was probed by addition of anti-HA antibody. In the examples demonstrated here, a mouse monoclonal anti-HA antibody (clone HA-7) labeled with biotin (Sigma-Aldrich, B9183) was used. One hundred microliters of anti-HA-biotin at 2 µg/mL was added to each slide followed by washing and addition of 100 µL of streptavidin-horseradish peroxidase (SA-HRP) conjugate (Ventana). For chromogenic based detection using diaminobenzidine (DAB), ready-to-use solutions of DAB, H$_2$O$_2$ and Copper from an ULTRAVIEW DAB Detection kit (Ventana) were used, followed by counter-stain with Hematoxylin II and Bluing (Ventana). Alternatively, the detection was achieved with cyanine 5-tyramide conjugate (Cy5-Tyr) after the addition of SA-HRP. A TSA™ Plus Cyanine 5 System kit from Perkin Elmer (Waltham, Mass.) was used. One hundred microliters of 1:50 Cyanine 5 Tyramide in 1× Plus Amplification Diluent was added to each slide and incubated for 16 minutes. The slide was mounted with VECTASHIELD HardSet Mounting Medium with DAPI (H-1500, VECTOR LABORATORIES, INC. Burlingame, Calif.). Fluorescence images were acquired using an Olympuc BX3-CBH microscope.

Figure 10:
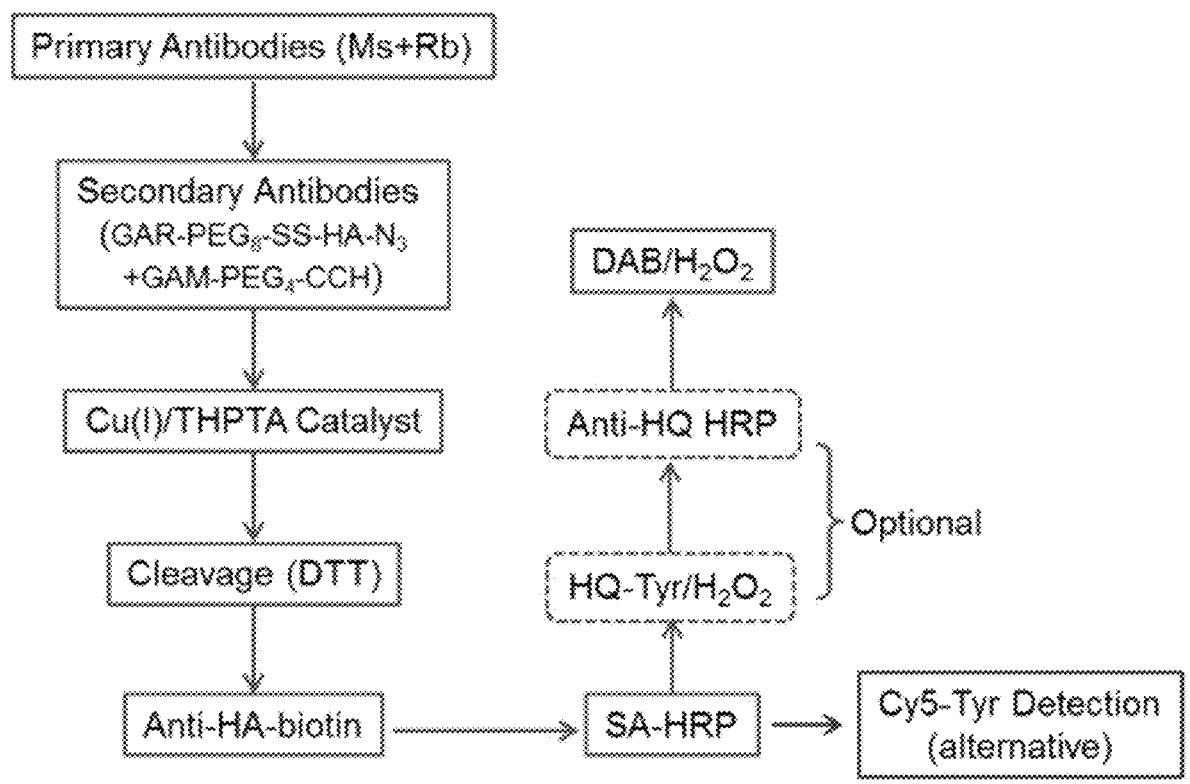
FIG. 10 is a flow chart showing steps used for a proximity assay and a subsequent immunohistochemistry assay for detection of the detectable moiety/hapten and an alternative detection approach using a fluorophore-tyramide (Cy5-Tyr) detection method.
Figure 16A:
FIG. 16A is a photomicrograph showing detection of E-cadherin(E-cad)/β-catenin(β-cat) in normal tonsil tissue sections with commercially available hapten-tyramide amplification (VENTANA OPTIVIEW Amplification Kit) showing proximity assay omitting Mouse anti-β-cat.
Figure 16B:
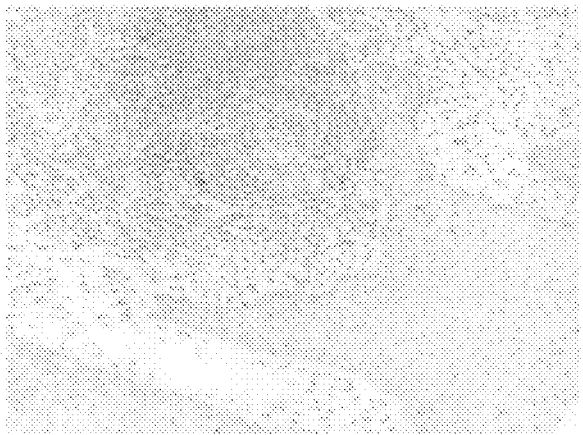
FIG. 16B is a photomicrograph showing detection of E-cadherin(E-cad)/β-catenin(β-cat) in normal tonsil tissue sections with commercially available hapten-tyramide amplification (VENTANA OPTIVIEW Amplification Kit) showing proximity assay omitting Rabbit anti-E-cad.
Figure 16C:
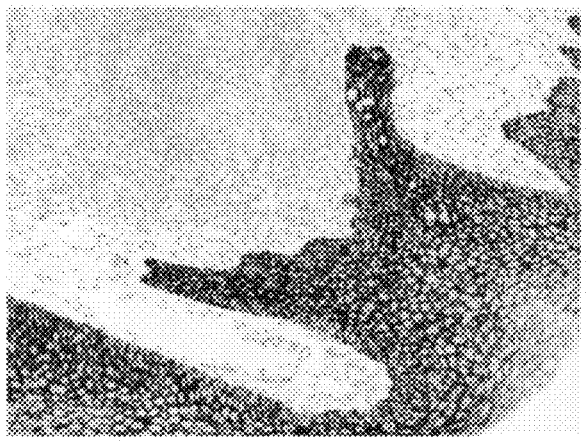
FIG. 16C is a photomicrograph showing detection of E-cadherin(E-cad)/β-catenin(β-cat) in normal tonsil tissue sections with commercially available hapten-tyramide amplification (VENTANA OPTIVIEW Amplification Kit) showing proximity assay omitting Rabbit anti-E-cad.
Figure 16D:
FIG. 16D is a photomicrograph showing detection of E-cadherin(E-cad)/β-catenin(β-cat) in normal tonsil tissue sections with commercially available hapten-tyramide amplification (VENTANA OPTIVIEW Amplification Kit) showing proximity assay omitting Rabbit anti-E-cad and Mouse anti-β-cat proximity assay excluding Cu(I).

To enhance the detection, a tyramide signal amplification scheme is adopted using an OPTIVIEW Amplification Kit (Ventana 860-099), which uses non-endogenous hapten 3-hydroxy-2-quinoxaline (HQ) coupled to tyramide. After 8-min TSA reaction and removal of excess reagent, anti-HQ antibody conjugated with HRP was added and incubated for 16 minutes. Finally, the detection was achieved using an ULTRAVIEW DAB Detection Kit (Ventana) with 12-minute reaction. The DAB staining is examined by standard bright field microscopy. FIG. 10 shows the flow chart for the major steps for the IHC procedure as described above.
Results
Detection of E-Cadherin/β-Catenin/p120-Catenin Complex
The complex of E-Cadherin(E-cad)/β-Catenin(β-cat)/p120-Catenin(p120) (*Nature Reviews Molecular Cell Biology,* 2005, 6, 622-634) provide an easily accessible model for demonstration of the proximity assay. Based on the availability of the primary antibodies, three pairs of target were tested: E-cad/β-cat, E-cad/p120 and E-cad Ms/Rb primary antibodies. Two types of negative controls were also used: omission of one of the primary antibodies or omission of Cu(I) catalyst. In addition, the assay was performed both on tonsil and skin tissue sections to should the generality of the assay. Results are shown in FIG. 15-FIG. 19. Referring now to FIG. 16A-FIG. 16D, shown are photomicrographs in which the detection of E-cadherin(E-cad)/β-catenin(β-cat) in normal tonsil tissue sections with commercially available hapten-tyramide amplification (VENTANA OPTIVIEW Amplification Kit) is shown. FIG. 16A shows the assay omitting Mouse anti-β-cat, FIG. 16B shows the assay omitting Rabbit anti-E-cad, FIG. 16C shows the Rabbit anti-E-cad and Mouse anti-β-cat proximity assay with Cu(I), and FIG. 16D shows a Rabbit anti-E-cad and Mouse anti-β-cat proximity assay excluding Cu(I).

Figure 17A:
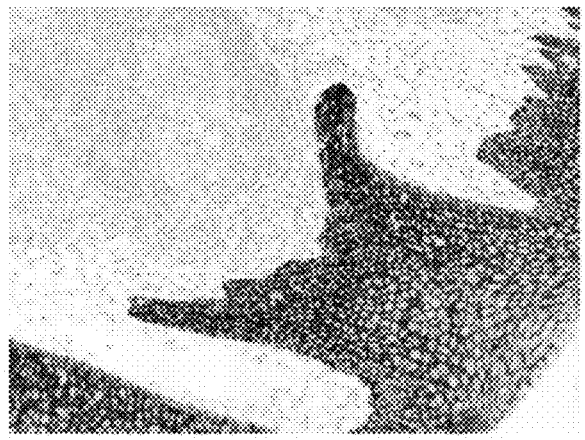
FIG. 17A is a photomicrograph showing an assay for detecting the proximity of E-cadherin(E-cad) and p120-catenin (p120) in normal tonsil sections slides using Cu(I) and VENTANA OPTIVIEW DAB and VENTANA Amplification Kit.
Figure 17B:
FIG. 17B is a photomicrograph showing an assay for detecting the proximity of E-cadherin(E-cad) and p120-catenin (p120) in normal tonsil sections slides] showing the negative control without inclusion of Cu(I).
Figure 17C:
FIG. 17C is a photomicrograph of sections in which E-cadherin was detected using a mouse-anti-Ecad and a rabbit-anti-Ecad primary antibodies to bind to different epitopes of the protein in normal tonsil tissue sections with the proximity assay as described herein.
Figure 17D:
FIG. 17D is a photomicrograph of sections in which E-cadherin was detected using a mouse-anti-Ecad and a rabbit-anti-Ecad primary antibodies to bind to different epitopes of the protein in normal tonsil tissue sections with the proximity assay excluding Cu(I) (FIG. 17D).

Referring now to FIG. 17A-FIG. 17D, shown are photomicrographs in which FIG. 17A shows an assay for detecting the proximity of E-cadherin(E-cad) and p120-catenin (p120) in normal tonsil sections slides using Cu(I) and VENTANA OPTIVIEW DAB and VENTANA Amplification Kit, and FIG. 17B shows the negative control without inclusion of Cu(I). FIG. 17C-FIG. 17D are photomicrographs of sections in which E-cadherin was detected using a mouse-anti-Ecad and a rabbit-anti-Ecad primary antibodies to bind to different epitopes of the protein in normal tonsil tissue sections with the proximity assay as described herein (FIG. 17C) and the proximity assay excluding Cu(I) (FIG. 17D). Referring to FIG. 18A-FIG. 18D, shown are photomicrographs in which the detection of E-cadherin(E-cad)/β-catenin(β-cat) in normal skin tissue sections stained with VENTANA OPTIVIEW DAB with amplification is shown. FIG. 18A shows the proximity assay between E-cad and β-cat and FIG. 18B is a control in which the Cu(I) was excluded. FIG. 18C also shows the proximity assay between E-cad and β-cat in a different skin section and FIG. 18D is the corresponding negative control in which the Cu(I) catalyst was excluded.

FIG. 19A-FIG. 19C are photomicrographs showing fluorophore-tyramide based detection of Ecad/β-cat in normal tonsil sections using Cy5-Tyr (Blue=DAPI, Red=Cy5 for Ecad/β-cat).

In all the assays, only when all the necessary components (both primary antibodies and Cu(I) catalyst) are present, positive staining is achieved. If one of the primary antibodies or the Cu(I) catalyst is omitted, no positive staining is obtained. These results clearly demonstrate the feasibility and specificity of the assay for FFPE tissues. Furthermore, the detection can be achieved by either chromogenic or fluorogenic signals, suggesting the flexibility of method.

Detection of CD19/CD21 Complex

To further demonstrate the generality of the method, detection of CD19/CD21 complex in tonsil is performed. CD19 is a B-cell-specific transmembrane glycoprotein that is expressed from the pro-B-cell to the plasma-cell stage. On mature B cells, CD19 associates with three different molecules to form a tetrameric complex comprising CD21 (complement receptor type 2), CD81 (transporter for antigen processing 1) and LEU13 (interferon-induced transmembrane protein 1) (*Nature Reviews Immunology* 2, 354-363, 2002). Results are shown in FIG. 20A-FIG. 20D, which are photomicrographs showing in FIG. 20A the proximity assay of CD19/CD21 in normal tonsil tissue sections stained with VENTANA OPTIVIEW DAB with amplification. FIG. 20B is a control of FIG. 20A in which the Cu(I) was excluded. FIG. 20C shows detection of CD21 by using mouse-anti-CD21 and rabbit-anti-CD21 primary antibodies in normal tonsil tissue, and FIG. 20D is the control of FIG. 20C in which the Cu(I) was excluded. Again, specific staining is only achieved when all the necessary antibodies and Cu(I) catalyst are applied.

Example 6

Example 6 describes experiments using the methods of the present invention. The present invention may be used to detect various post-transitional modification states such as phosphorylation, glycosylation, ubiquitination, nitrosylation, methylation, acetylation, lipidation, and/or the like. See, for example, FIG. 6. Example 4 describes experiments using the methods of the present invention to detect protein phosphorylation and ubiquitination.

Figures 21A, 21B, 21C:
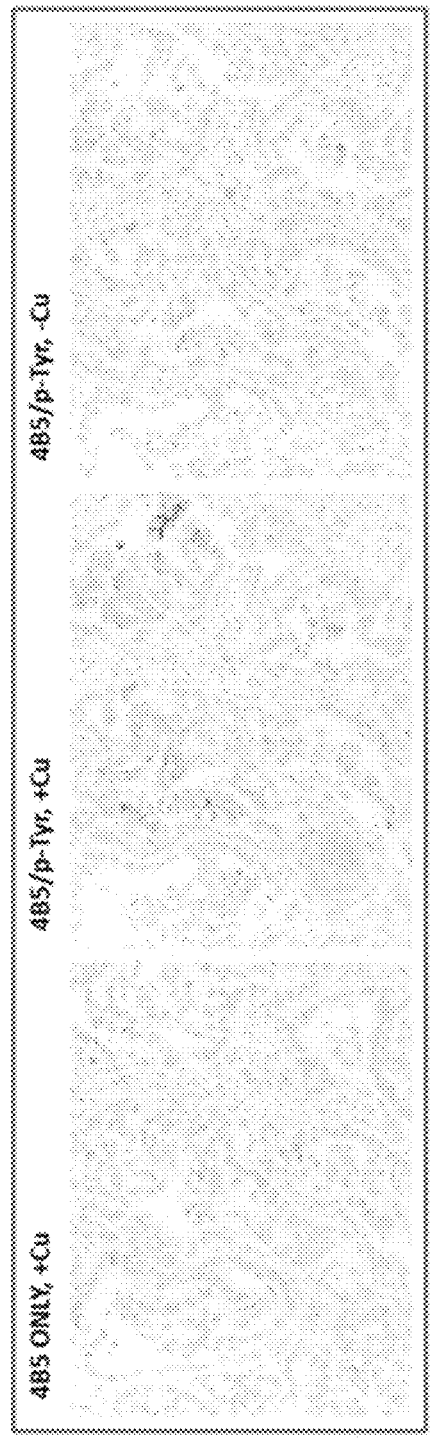
FIG. 21A is a photomicrograph showing the proximity assay being used to detect HER2 phosphorylation using anti-HER2 (Clone 4B5) and an anti-p-Tyr antibody to detect phosphorylation. The tissue is from a 3-in-1 xenograft slides using DAB chromogenic detection showing addition of anti-HER2 antibody only.
FIG. 21B is a photomicrograph showing the proximity assay being used to detect HER2 phosphorylation using anti-HER2 (Clone 4B5) and an anti-p-Tyr antibody to detect phosphorylation. The proximity assay illustrated uses the anti-HER2 (Clone 4B5) and the anti-p-Tyr antibody with Cu(I)
FIG. 21C is a photomicrograph showing the proximity assay being used to detect HER2 phosphorylation using anti-HER2 (Clone 4B5) and an anti-p-Tyr antibody to detect phosphorylation. The proximity assay illustrated shows the control of FIG. 21B in which Cu(I) was excluded.

Results of the detection of HER2 phosphorylation is Calu3 xenograft are shown in FIG. 21A-FIG. 21C. Signal is only detected when both anti-HER2 and the anti-tyrosine phosphorylation antibody(p-Tyr) are applied and no signal when either anti-p-Tyr or Cu(I) catalyst is omitted.

Figure 22:
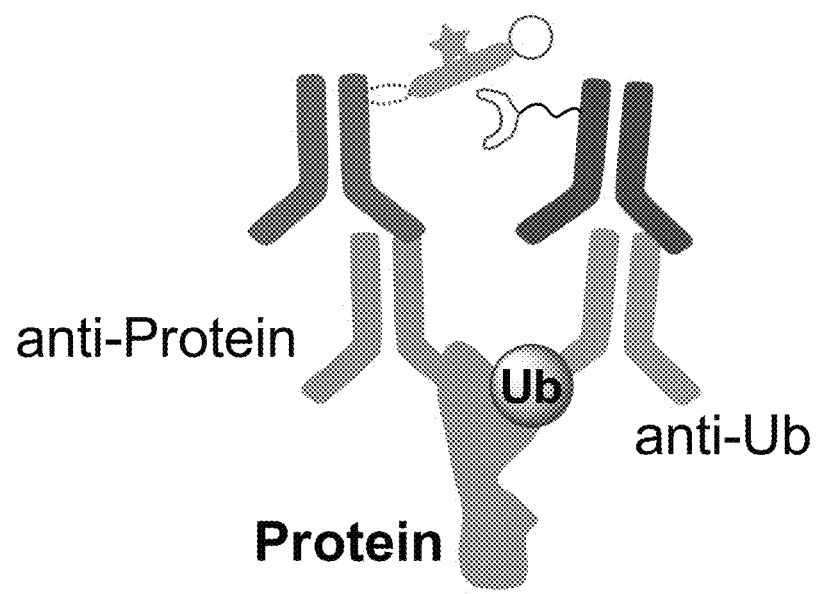
FIG. 22 is a schematic illustration of the detection of ubiquitination of a protein using an assay as described herein.
Figure 23A:
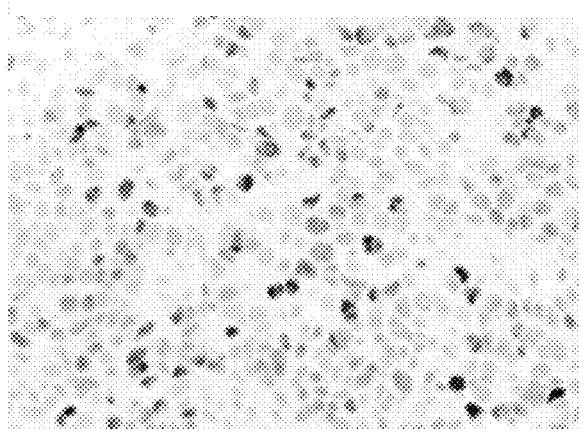
FIG. 23A is a photomicrograph showing detection of ubiquitination of progesterone receptor (PR) in MCF-7 xenograft showing the proximity assay between PR and Ubiquitin. MCF-7 cells are PR positive.
Figure 23B:
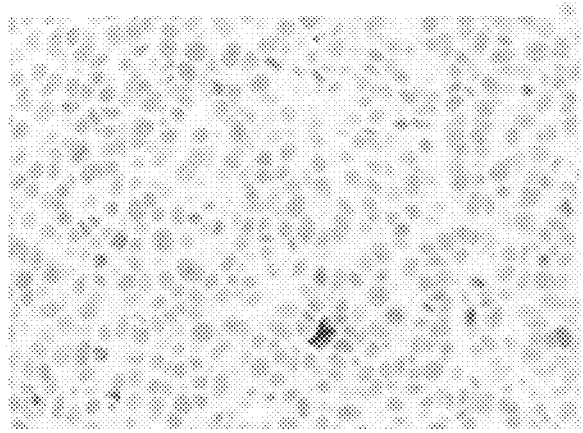
FIG. 23B is a photomicrograph showing detection of ubiquitination of progesterone receptor (PR) in MCF-7 xenograft showing the proximity assay a control of the proximity assay without the Cu(I) catalyst.
Figure 23C:
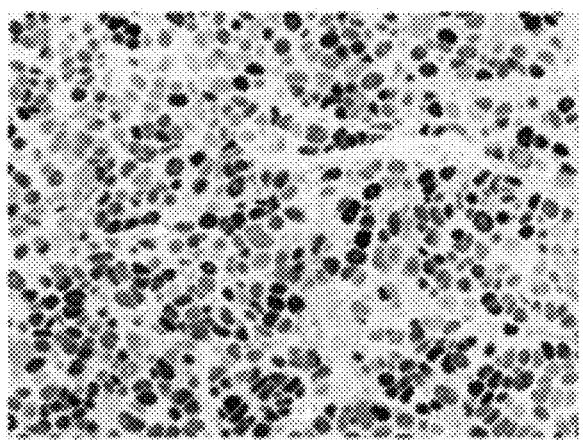
FIG. 23C is a photomicrograph showing detection of ubiquitination of progesterone receptor (PR) in MCF-7 xenograft showing the standard IHC detection of PR detected using commercially available VENTANA ULTRAVIEW DAB detection.
Figure 23D:
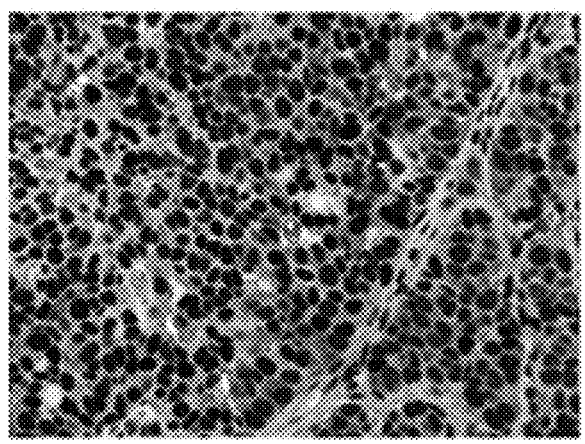
FIG. 23D is a photomicrograph showing detection of ubiquitination of progesterone receptor (PR) in MCF-7 xenograft showing the standard IHC detection of ubiquitin detected using commercially available VENTANA ULTRAVIEW DAB detection.
Figure 24A:
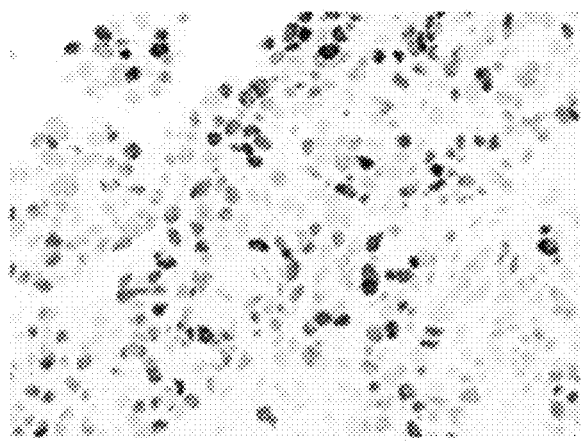
FIG. 24A is a photomicrograph showing detection of ubiquitination of progesterone receptor (PR) in ZR-7551 xenograft showing the proximity assay between PR and Ubiquitin. ZR-751 cells are PR positive.
Figure 24B:
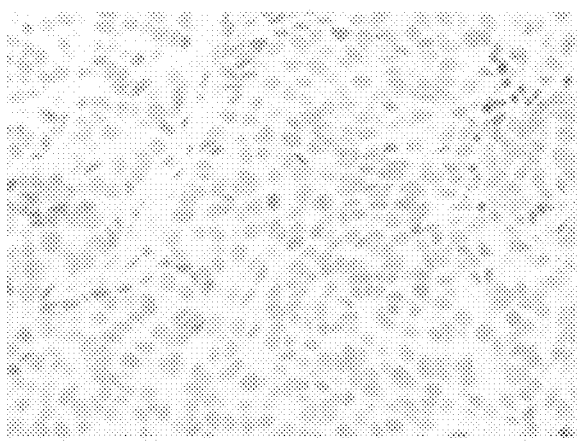
FIG. 24B is a photomicrograph showing detection of ubiquitination of progesterone receptor (PR) in ZR-7551 xenograft showing the control of the proximity assay without the Cu(I) catalyst.
Figure 24C:
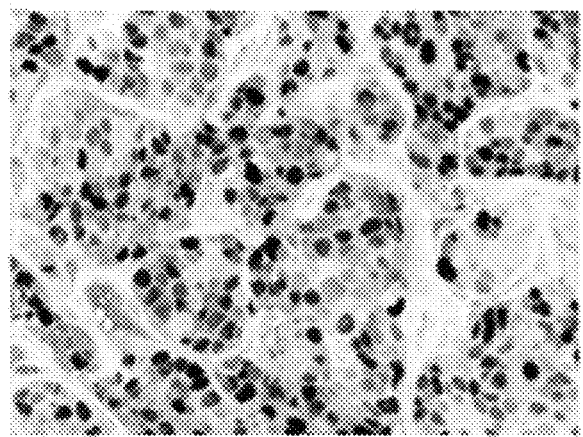
FIG. 24C is a photomicrograph showing detection of ubiquitination of progesterone receptor (PR) in ZR-7551 xenograft showing the standard IHC detection using commercially available VENTANA ULTRAVIEW DAB detection.
Figure 24D:
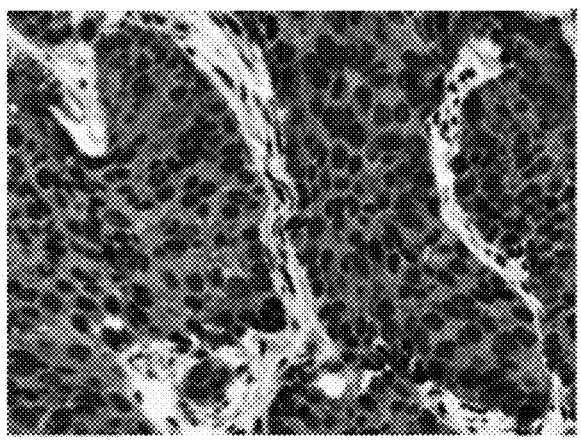
FIG. 24D is a photomicrograph showing detection of PR and ubiquitin using commercially available VENTANA ULTRAVIEW DAB detection.
Figure 25A:
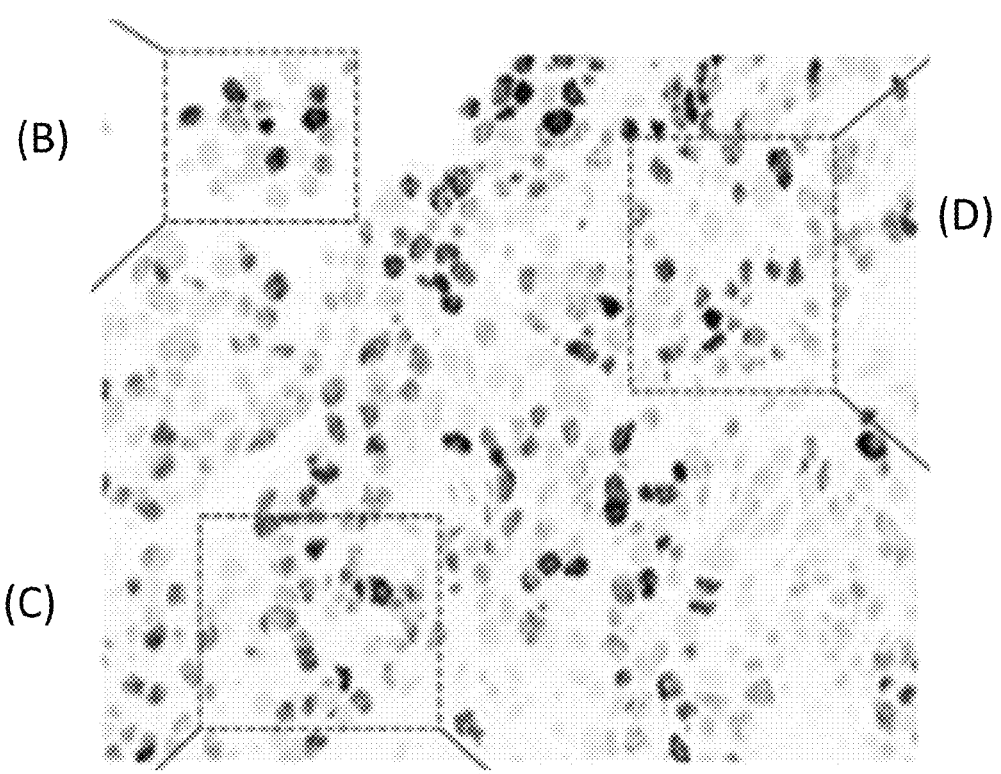
FIG. 25A is a photomicrograph similar to that shown in FIG. 24A except that it shows regions demarcated as (B)-(D).
Figure 25B:
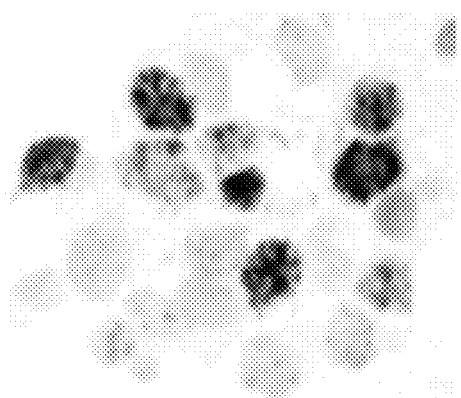
FIG. 25B is a photomicrograph shown at a higher magnification than that show in FIG. 25A. The higher magnification more readily shows the heterogeneity of ubiquitinated PR.
Figure 25C:
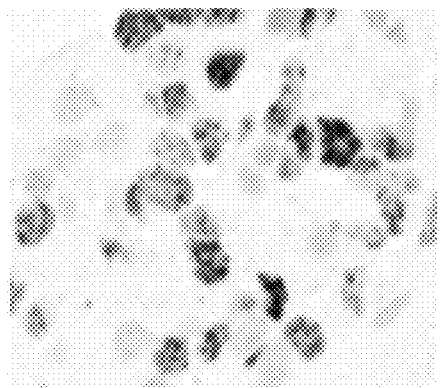
FIG. 25C is an additional photomicrograph shown at a higher magnification than that show in FIG. 25A. The higher magnification more readily shows the heterogeneity of ubiquitinated PR.
Figure 25D:
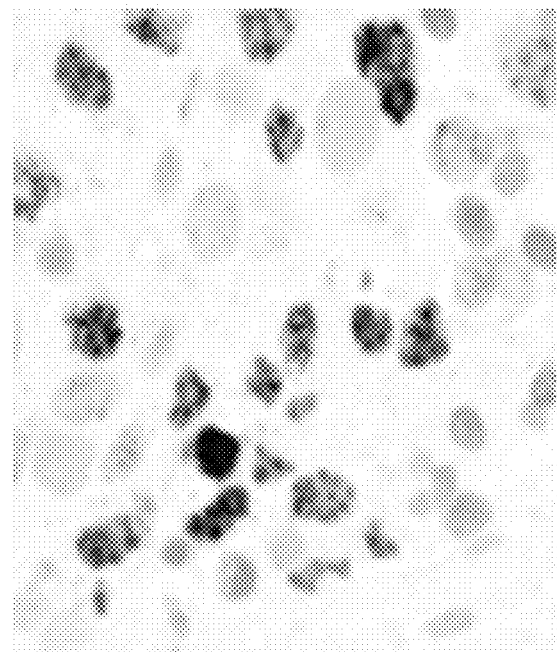
FIG. 25D is an additional photomicrograph shown at a higher magnification than that show in FIG. 25A. The higher magnification more readily shows the heterogeneity of ubiquitinated PR.
Figure 26A:
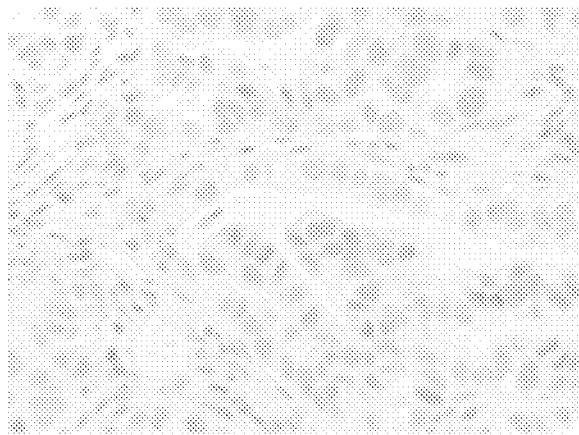
FIG. 26A is a photomicrograph showing the no detection of ubiquitination of progesterone receptor (PR) in Calu-3 xenograft. This image shows the lack of signal for a proximity assay between PR and Ubiquitin. Calu-3 cells are PR negative.
Figure 26B:
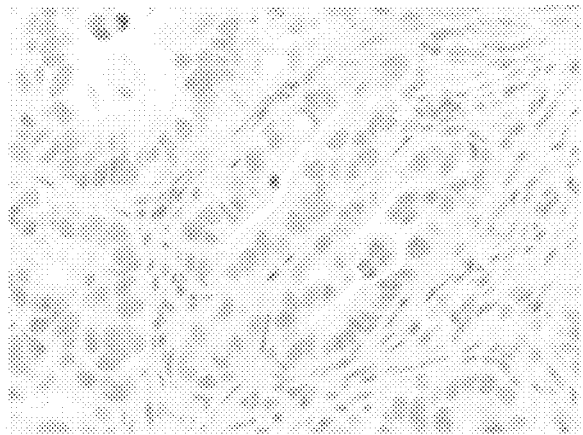
FIG. 26B is a photomicrograph showing the no detection of ubiquitination of progesterone receptor (PR) in Calu-3 xenograft. This image shows a control of the proximity assay without the Cu(I) catalyst. Calu-3 cells are PR negative.
Figure 26C:
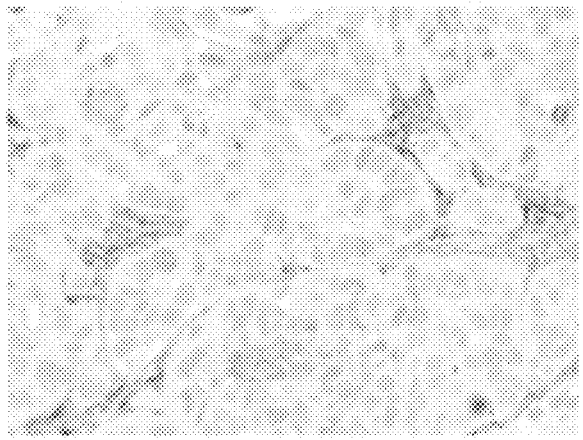
FIG. 26C is a photomicrograph showing the no detection of ubiquitination of progesterone receptor (PR) in Calu-3 xenograft. This image shows the standard IHC detection of PR detected using commercially available VENTANA ULTRAVIEW DAB detection.
Figure 26D:
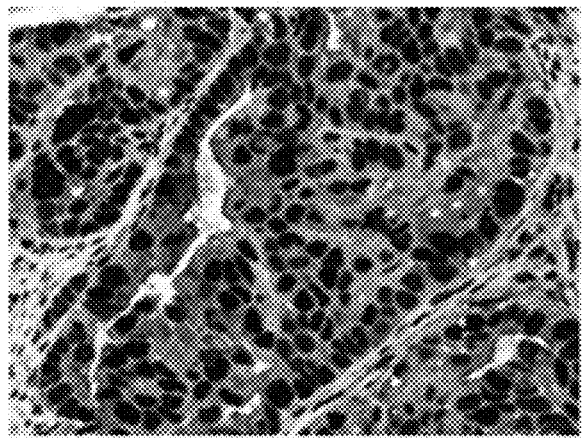
FIG. 26D is a photomicrograph showing the no detection of ubiquitination of progesterone receptor (PR) in Calu-3 xenograft. This image shows the standard IHC detection of ubiquitin detected using commercially available VENTANA ULTRAVIEW DAB detection.
Figures 27A, 27B, 27C:
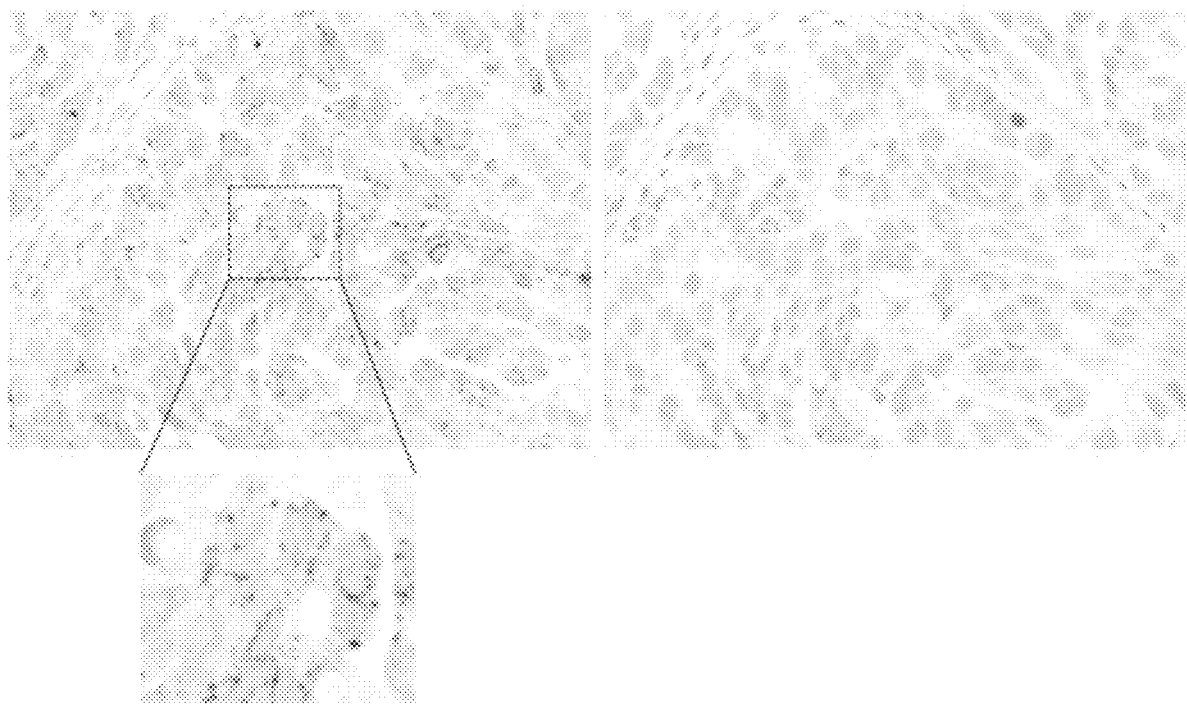
FIG. 27A is a photomicrograph showing detection of ubiquitination of HER2 in Calu-3 cells. Calu-3 cells are HER2 positive showing the proximity assay between HER2 and Ubiquitin.
FIG. 27B is a photomicrograph showing detection of ubiquitination of HER2 in Calu-3 cells. Calu-3 cells are HER2 positive showing a control of the proximity assay without the Cu(I) catalyst.
FIG. 27C is a photomicrograph showing detection of ubiquitination of HER2 in Calu-3 cells showing a region of FIG. 27A under higher magnification.

Without wishing to limit the present invention to any theory or mechanism, it is believed that it is not possible to raise specific antibodies to detect specific proteins with ubiquitin modification. Unlike detection of phosphorylated proteins for which a peptide with the phosphorylated amino acid residue can be readily used as immunogen to generate antibodies, ubiquitin is a 8.5 kDa protein and thus makes is extremely difficult to generate antibodies for a specific ubiquitinated protein. However, antibodies against ubiquitin itself are widely available (e.g., generated by using full length ubiquitin as the immunogen) could be paired with antibodies against specific proteins of interest to provide a method for the detection of ubiquitinated proteins using the proximity assay method in current invention FIG. 22-FIG. 27 relate to assays for detecting ubiquitinated proteins (e.g., PR, HER2). As depicted in FIG. 22, an antibody specific for the protein itself is used in combination with an antibody specific for ubiquitin. If the two targets are in close proximity (e.g., the protein is ubiquitinated), the covalent bond between the bridge components can form (following the external stimulation, e.g., catalyst, etc.). The bridge component can then be cleaved from the first antibody, and the covalently bonded bridge components can subsequently be detected using a detection system (e.g., chromogenic detection system). For the assays in FIG. 23-FIG. 26, mouse anti-ubiquitin (clone P4D1) mAb was used as a pan-anti-ubiquitin antibody (Cell Signaling Technology), and rabbit-anti-PR (clone 1E2, Ventana catalog #790-2223) was used as the anti-PR antibody.

As shown in FIG. 23-FIG. 26, positive signal is detected only with all the necessary antibodies and Cu(I) applied. Interestingly, the signal appears to be heterogeneous, which suggests a unique advantage of the current in situ proximity assay over "grind and bind" methods such as western blot in which the heterogeneity information would be lost. In addition, positive staining is not observed in every cell, which suggests the extremely high distance stringency of the current method as nuclear co-localization of PR and ubiquitin (as shown in the standard IHC) is not sufficient to generate proximity signal. Furthermore, the staining is all localized in the cell nuclei, which is in accordance with the native expression pattern of the targets. For the assays in FIG. 27, rabbit-anti-HER2 (clone 4B5, Ventana catalog #790-2991) was used as the anti-HER2 antibody. And positive signal is only observed in Calu3 xenograft, in which HER2 expression is positive.

Example 7

Figure 28A:
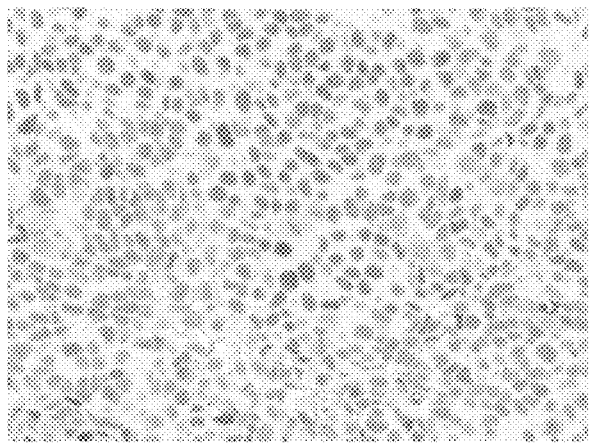
FIG. 28A is a photomicrograph showing detection of MLH1-PMS2 heterodimers using the proximity assay of the present invention. This figure illustrates standard IHC of PMS2 in Hela cell xenograft using rabbit-anti-PMS2 mAb.
Figure 28B:
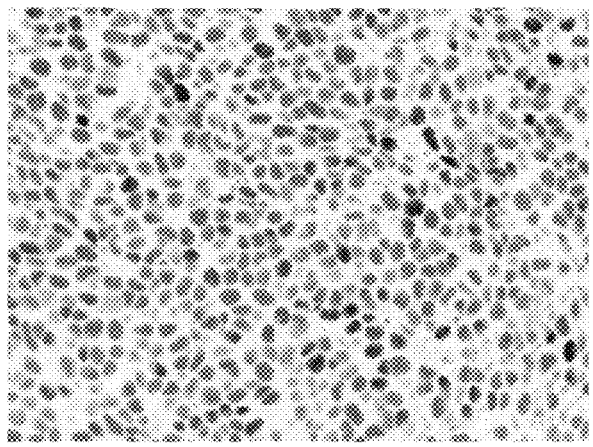
FIG. 28B is a photomicrograph showing detection of MLH1-PMS2 heterodimers using the proximity assay of the present invention. This figure illustrates IHC of MLH1 in Hela cell xenograft using mouse-anti-MLH1 mAb.
Figure 28C:
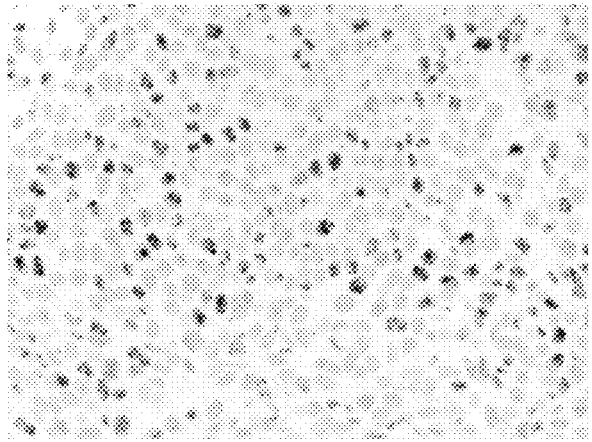
FIG. 28C is a photomicrograph showing detection of MLH1-PMS2 heterodimers using the proximity assay of the present invention. This figure illustrates a proximity assay of MLH1-PMS2 heterodimers
Figure 28D:
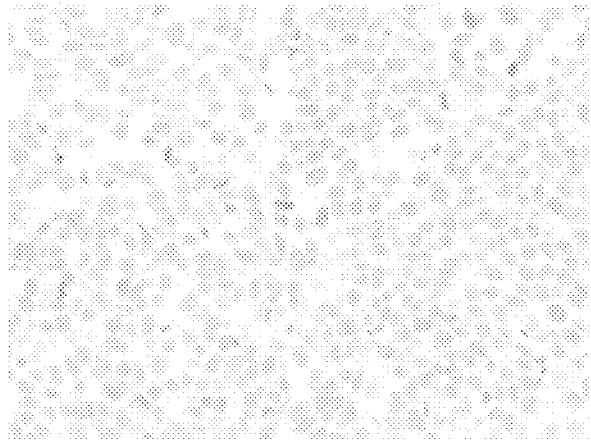
FIG. 28D is a photomicrograph showing detection of MLH1-PMS2 heterodimers using the proximity assay of the present invention. This figure illustrates a control of the proximity assay without the Cu(I) catalyst.

Example 7 describes the detection of MLH1-PMS2 heterodimers using the proximity assay of the present invention. FIG. 28A shows the results of IHC of PMS2 in Hela cell xenograft using rabbit-anti-PMS2 mAb (clone EPR3947, Ventana 760-4531). The expected nuclear staining is visible. FIG. 28B shows the results of IHC of MLH1 in Hela cell xenograft using mouse-anti-MLH1 mAb (clone M1, Ventana 790-4535). The expected nuclear staining is confirmed. FIG. 28C shows the results of the proximity assay of MLH1-PMS2 heterodimers using the current method with Cu(I) catalyst added. Note the nuclear localization and heterogeniety of the signal. FIG. 28D shows the results of the proximity assay of MLH1-PMS2 heterodimers using the current method but with no Cu(I) catalyst added. The results further demonstrate the specificity and generality of the current invention.

As used herein, the term "about" refers to plus or minus 10% of the referenced number. Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

ADDITIONAL EXEMPLARY EMBODIMENTS

The following additional embodiments are also specifically disclosed. This is not an exhaustive list.

1. A method of determining that a first target and a second target in a sample are proximal, the method comprising:
   binding a first modified binding molecule to the first target to form a first complex, wherein, the first modified binding molecule comprises a cleavable bridge component, the cleavable bridge component comprises a cleavage site, a detectable moiety, and a first chemical ligation group, the cleavage site is more proximal to the first modified binding molecule than is the detectable moiety and the first chemical ligation group, the first chemical ligation group is at a terminus of the cleavable bridge component, the first chemical ligation group is stable under physiological conditions;
   binding a second modified binding molecule to the second target to form a second complex, the second modified binding molecule comprises a non-cleavable bridge component, the non-cleavable bridge component comprises a second chemical ligation group, the second chemical ligation group is at a terminus of the non-cleavable bridge component, the second chemical ligation group is stable under physiological conditions;
   covalently linking the first chemical ligation group to the second chemical ligation group to form a covalently bonded unit where the first target and the second target are proximal;
   cleaving the cleavage site of the cleavable bridge component such that the covalently bonded unit is bound to the second modified binding molecule and not the first modified binding molecule;
   removing cleavable bridge components that are not part of a covalently bonded unit; and
   making the detectable moiety visible, wherein the first target and the second target are proximal where the detectable moiety is visible.
2. The method of embodiment 1, wherein the first target and the second target are proximal in that they are less than about 40 nm apart.
3. The method of embodiment 1, wherein the first target and the second target are proximal in that they are less than about 30 nm apart.
4. The method of any of embodiments 1 to 3, wherein the method is performed using an automated staining instrument.
5. The method of any of embodiments 1 to 4, wherein the first modified binding molecule comprises a first antibody and the second modified binding molecule comprises a second antibody.
6. The method of any of embodiments 1 to 4, wherein the first modified binding molecule comprises a first primary antibody and a first secondary antibody, and the second modified binding molecule comprises a second primary antibody and a second secondary antibody, wherein the first secondary antibody specifically binds the first primary antibody and not the second primary antibody, and the second secondary antibody specific binds the second primary antibody and not the first primary antibody, wherein the cleavable bridge component is bound to the first secondary antibody and the non-cleavable bridge component is bound to the second secondary antibody.
7. The method of any of embodiments 1 to 6, wherein the cleavage site comprises a disulfide bond, a vicinal diol, or a nitrophenyl derivative.
8. The method of any of embodiments 1 to 7, wherein the cleavable bridge component comprises more than one detectable moiety.
9. The method of any of embodiments 1 to 8, wherein the detectable moiety comprises hapten, a peptide tag, or an oligonucleotide.
10. The method of embodiment 9, wherein the detectable moiety is a hapten selected from an oxazole hapten, pyrazole hapten, thiazole hapten, nitroaryl hapten, benzofuran hapten, triterpene hapten, urea hapten, thiourea hapten, rotenoid hapten, coumarin hapten, cyclolignan hapten, di-nitrophenyl hapten, biotin hapten, digoxigenin hapten, fluorescein hapten, and rhodamine hapten.
11. The method of embodiment 9, wherein the peptide tag is HA-tag, FLAG tag, Myc Tag, V5 Tag, E-Tag, or VSV Tag.
12. The method of any of embodiments 1 to 11, wherein the cleavable bridge component further comprises a scaffold, wherein the detectable moiety is bound to the scaffold.
13. The method of embodiment 12, wherein the scaffold comprises a peptide, an oligonucleotide, or a polymer.
14. The method of embodiment 12, wherein the scaffold comprises lysine.
15. The method of any of embodiments 1 to 14, wherein the first chemical ligation group comprises an azide

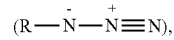

a thioester

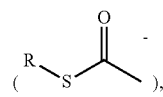

or a tetrazole ring

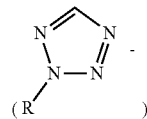

an alkyne group (RC≡CH), a halogen group, or an alkene group (RC=CH$_2$).

16. The method of any of embodiments 1 to 11, wherein the cleavable bridge component comprises x polyethylene glycol groups (PEG$_x$), wherein x≥1.
17. The method of embodiment 16, wherein x≥8.
18. The method of any of embodiments 1 to 17, wherein the second chemical ligation group comprises an alkyne group (RC≡CH), a halogen group, or an alkene group (RC=CH$_2$).
19. The method of embodiment 18, wherein the halogen group comprises —Cl, —Br, or
20. The method of any of embodiments 1 to 19, wherein the non-cleavable bridge component comprises x polyethylene glycol groups (PEG$_x$), wherein x≥1.
21. The method of embodiment 20, wherein x≥4.
22. The method of any of embodiments 1 to 21, wherein covalently linking the first chemical ligation group to the second chemical ligation group comprises contacting the sample with a catalyst, ultraviolet light, and/or a deprotection condition.
23. The method of any of embodiments 1 to 21, wherein covalently linking the first chemical ligation group to the second chemical ligation group comprises contacting the sample with copper (I) or hydrazine (N$_2$H$_4$).
24. The method of any of embodiments 1 to 21, wherein covalently linking the first chemical ligation group to the second chemical ligation group comprises initiating a Huisgen 1,3-dipolar cycloaddition reaction.
25. The method of any of embodiments 1 to 24, wherein cleaving the cleavage site of the cleavable bridge component comprises contacting the sample with a reducing agent, sodium periodate (NaIO$_4$), or ultraviolet light.
26. The method of any of embodiments 1 to 24, wherein cleaving the cleavage site of the cleavable bridge component comprises contacting the sample with dithiothreitol (DTT), beta-mercaptoethanol (BME), or tris (2-carboxyethyl)phosphine (TCEP).
27. The method of embodiment 1, wherein the first modified binding molecule comprises antibody-PEG$_8$-SS-HA-N$_3$.
28. The method of embodiment 1 or the method of embodiment 27, wherein the second modified binding molecule comprises antibody-PEG$_4$-CCH.
29. The method of any of embodiments 1 to 28, wherein removing cleavable bridge components comprises washing the sample with a buffer.
30. The method of any of embodiments 1 to 29, making the detectable moiety visible comprises contacting the sample with a chromogenic detection system.
31. The method of embodiment 30, wherein the chromogenic detection system comprises tyramide signal amplification.
32. The method of any of embodiments 1 to 29, wherein making the detectable moiety visible comprises contacting the sample with a fluorogenic detection system.
33. The method of embodiment 32, wherein the fluorogenic detection system comprises a tyramide-fluorophore conjugate.
34. The method of embodiment 33, wherein the tyramide-fluorophore conjugate comprises cyanine 5-tyramide conjugate (Cy5-Tyr).
35. The method of any of embodiments 1 to 34, wherein the first modified binding molecule comprises two or more cleavable bridge components.
36. The method of any of embodiments 1 to 35, wherein the second modified binding molecule comprises two or more non-cleavable bridge components.
37. The method of any of embodiments 1 to 36, wherein the chemical ligation groups are adapted to form the covalently bonded unit in less than two hours.
38. A method of detecting a first target located proximally to a second target in a sample, the method comprising:
    labelling the first target with a first conjugate comprising a cleavable bridge component, the cleavable bridge component comprises a cleavage site, a detectable moiety, and a first chemical ligation group,
    labelling the second target with a second conjugate comprising a non-cleavable bridge component, the non-cleavable bridge component comprises a second chemical ligation group,
    activating the first chemical ligation group or the second chemical ligation group so a covalent bond can form where the first target and the second target are proximal;
    cleaving the detectable moiety from the first target site;
    washing the sample to remove unbound detectable moiety; and
    detecting the detectable moiety visible.
39. The method of embodiment 38, wherein labelling the first target comprises binding a first primary antibody to the first target.
40. The method of embodiment 38 or 39, wherein labelling the second target comprises binding a second primary antibody to the second target.
41. The method of embodiment 38, wherein labelling the first target comprises binding a first primary antibody and a first secondary antibody to the target, wherein the cleavable bridge component is bound to the first secondary antibody.
42. The method of embodiment 38 or 41, wherein labelling the second target comprises binding a second primary antibody and a second secondary antibody to the target, wherein the non-cleavable bridge component is bound to the second secondary antibody.
43. The method of embodiment 38, wherein the first conjugate has a structure of an antibody linked through the cleavable bridge component to a detectable moiety linked to the first chemical ligation group.
44. The method of any of embodiments 38 to 43, wherein the cleavage site comprises a disulfide bond, a vicinal diol, a vicinal hydroxylamine, or a nitrophenyl derivative.
45. The method of any of embodiments 38 to 44, wherein the first conjugate cleavable bridge component comprises two or more detectable moieties.
46. The method of any of embodiments 38 to 45, wherein the detectable moiety is a peptide tag, or an oligonucleotide, a hapten, or a fluorophore.
47. The method of any of embodiments 38 to 46, wherein the first conjugate comprises a scaffold upon which one or more of the detectable moieties is bound.
48. The method of embodiment 47, wherein the scaffold comprises a peptide, an oligonucleotide, or a polymer.
49. The method of embodiment 47, wherein the scaffold comprises lysine.
50. The method of any of embodiments 38 to 49, wherein the first chemical ligation group comprises an azide

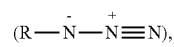

a thioester

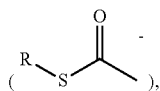

or a tetrazole ring

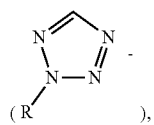

an alkyne group (RC≡CH), a halogen group, or an alkene group (RC=CH$_2$).

51. The method of any of embodiments 38 to 50, wherein the cleavable bridge component comprises x polyethylene glycol groups (PEG$_x$), wherein x≥1.
52. The method of embodiment 50, wherein x≥8.
53. The method of any of embodiments 38 to 52, wherein the second chemical ligation group comprises an alkyne group (RC≡CH), a halogen group, or an alkene group (RC=CH$_2$).
54. The method of any of embodiments 38 to 53, wherein the non-cleavable bridge component comprises x polyethylene glycol groups (PEG$_x$), wherein x≥1.
55. The method of embodiment 53, wherein x≥4.
56. The method of any of embodiments 38 to 55, wherein activating the first chemical ligation group or the second chemical ligation group so a covalent bond can form comprises contacting the sample with a catalyst, a deprotection condition, or irradiating the sample with light.
57. The method of any of embodiments 38 to 55, wherein activating the first chemical ligation group or the second chemical ligation group comprises contacting the sample with copper (I) or hydrazine (N$_2$H$_4$).
58. The method of any of embodiments 38 to 55, wherein activating the first chemical ligation group or the second chemical ligation group comprises initiating a Huisgen 1,3-dipolar cycloaddition reaction.
59. The method of embodiment 44, wherein cleaving the detectable moiety from the first target site comprises contacting the sample with a reducing agent, sodium periodate (NaIO$_4$), or ultraviolet light.
60. The method of embodiment 59, wherein the reducing agent comprises dithiothreitol (DTT), beta-mercaptoethanol (BME), or tris(2-carboxyethyl)phosphine (TCEP).
61. The method of embodiment 38, wherein labelling the first target comprises contacting the sample with the first conjugate having the structure: antibody-PEG$_8$-SS-HA-N$_3$.
62. The method of embodiment 38 or embodiment 61, wherein labelling the second target comprises contacting the sample with the second conjugate having the structure: antibody-PEG$_4$-CCH.
63. A kit for detecting proximity of a first target and a second target in a sample, said kit comprising:
    (a) a first modified binding molecule for binding to the first target, the first modified binding molecule comprises a cleavable bridge component, the cleavable bridge component comprises a cleavage site, a detectable moiety, and a first chemical ligation group; and
    (b) a second modified binding molecule for binding to the second target, the second modified binding molecule comprises a non-cleavable bridge component, the non-cleavable bridge component comprises a second chemical ligation group.
64. The kit of embodiment 63 wherein the first and second chemical ligation groups are stable under physiological conditions.
65. The kit of embodiment 63 or 64 further comprising a catalyst effective for covalently linking the first chemical ligation group to the second chemical ligation group to form a covalently bonded unit.
66. The kit of any of embodiments 63 to 65 further comprising a catalyst or a deprotection reagent for cleaving the cleavage site of the cleavable bridge component.
67. The kit of any of embodiments 63 to 66 further comprising a system for making the detectable moiety visible.
68. The kit of embodiment 67, wherein the system comprises a chromogenic system or a fluorescence system.
69. The kit of any of embodiments 63 to 68, wherein the first modified binding molecule comprises a first antibody and the second modified binding molecule comprises a second antibody.
70. The kit of any of embodiments 63 to 68, wherein the first modified binding molecule comprises a first primary antibody and a first secondary antibody, and the second modified binding molecule comprises a second primary antibody and a second secondary antibody, wherein the first secondary antibody is specific for the first primary antibody and not the second primary antibody, and the second secondary antibody is specific for the second primary antibody and not the first primary antibody, wherein the cleavable bridge component is bound to the first secondary antibody and the non-cleavable bridge component is bound to the second secondary antibody.
71. The kit of any of embodiments 63 to 70, wherein the cleavage site comprises a disulfide bond, a vicinal diol, a vicinal hydroxylamine, or a nitrophenyl derivative.
72. The kit of any of embodiments 63 to 71, wherein the cleavable bridge component comprises more than one detectable moiety.
73. The kit of any of embodiments 63 to 72, wherein the detectable moiety comprises a hapten, a peptide tag, or an oligonucleotide.
74. The kit of any of embodiments 63 to 73, wherein the cleavable bridge component further comprises a scaffold, wherein the detectable moiety is bound to the scaffold.
75. The kit of embodiment 74, wherein the scaffold comprises lysine.
76. The kit of any of embodiments 63 to 75, wherein the first chemical ligation group comprises an azide

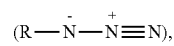

a thioester

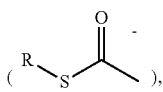

or tetrazole ring

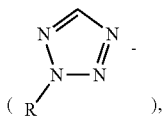

an alkyne group (RC≡CH), a halogen group, or an alkene group (RC=CH$_2$).

77. The kit of any of embodiments 63 to 76, wherein the cleavable bridge component comprises x polyethylene glycol groups (PEG$_x$), wherein x≥1.
78. The kit of any of embodiments 63 to 77, wherein the second chemical ligation group comprises an alkyne group (RC≡CH), a halogen group, or an alkene group (RC=CH$_2$).
79. The kit of any of embodiments 63 to 78, wherein the non-cleavable bridge component comprises x polyethylene glycol groups (PEG$_x$), wherein x≥1.
80. The kit of embodiment 65, wherein the catalyst comprises copper (I) or the deprotection reagent comprises hydrazine (N$_2$H$_4$).
81. The kit of embodiment 65, wherein the catalyst comprises a reducing agent or sodium periodate (NaIO$_4$).
82. The kit of embodiment 81, wherein the reducing agent comprises dithiothreitol (DTT), beta-mercaptoethanol (BME), or tris(2-carboxyethyl)phosphine (TCEP).
83. The kit of embodiment 63, wherein the first modified binding molecule comprises antibody-PEG$_8$-SS-HA-N$_3$.
84. The kit of embodiment 63 or embodiment 83, wherein the second modified binding molecule comprises antibody-PEG$_4$-CCH.
85. The kit of embodiment 68, wherein the chromogenic system comprises an anti-detectable moiety antibody conjugated with biotin.
86. The kit of embodiment 85, wherein the chromogenic system further comprises a streptavidin-horseradish peroxidase (SA-HRP) molecule.
87. The kit of embodiments 86, wherein the chromogenic system further comprises DAB, hydrogen peroxide, and copper.
88. A composition comprising an antibody conjugated with at least one a cleavable bridge component, the cleavable bridge component comprises a cleavage site, a detectable moiety, and a first chemical ligation group, the cleavage site is more proximal to the antibody than is the detectable moiety and the first chemical ligation group, the first chemical ligation group is at or near a terminus of the cleavable bridge component, the first chemical ligation group is stable under physiological conditions.
89. The composition of embodiment 88, wherein the antibody is conjugated with at least two cleavable bridge components.
90. The composition of embodiment 88, wherein the antibody is conjugated with at least three cleavable bridge components.
91. The composition of embodiment 88, wherein the antibody is conjugated with at least four cleavable bridge components.
92. The composition of any of embodiments 88 to 91, wherein the cleavage site comprises a disulfide bond, a diol, or a nitrophenyl derivative.
93. The composition of any of embodiments 88 to 92, wherein the cleavable bridge component comprises more than one detectable moiety.
94. The composition of any of embodiments 88 to 93, wherein the detectable moiety comprises a hapten, a peptide tag, or an oligonucleotide.
95. The composition of embodiment 94, wherein the peptide tag comprises HA-tag, FLAG tag, Myc Tag, V5 Tag, E-Tag, or VSV Tag.
96. The composition of any of embodiments 88 to 95, wherein the cleavable bridge component further comprises a scaffold, wherein the detectable moiety is bound to the scaffold.
97. The composition of embodiment 96, wherein the scaffold comprises lysine.
98. The composition of any of embodiments 88 to 97, wherein the first chemical ligation group comprises an azide

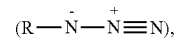

a thioester

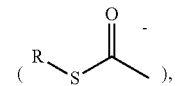

or a tetrazole ring

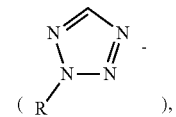

an alkyne group (RC≡CH), a halogen group, or an alkene group (RC=CH$_2$).

99. The composition of any of embodiments 88 to 98, wherein the cleavable bridge component comprises x polyethylene glycol groups (PEG$_x$), wherein x≥1.
100. The composition of embodiment 99, wherein x≥8.
101. A composition comprising an antibody conjugated with at least one non-cleavable bridge component, the non-cleavable bridge component comprises a second chemical ligation group, the second chemical ligation group is at or near a terminus of the non-cleavable bridge component, the second chemical ligation group is stable under physiological conditions.
102. The composition of embodiment 101, wherein the antibody is conjugated with at least two non-cleavable bridge components.
103. The composition of embodiment 101, wherein the antibody is conjugated with at least three non-cleavable bridge components.
104. The composition of embodiment 101, wherein the antibody is conjugated with at least four non-cleavable bridge components.

105. The composition of any of embodiments 101 to 104, wherein the second chemical ligation group comprises an azide

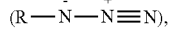

a thioester

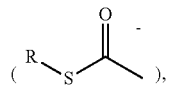

a tetrazole ring

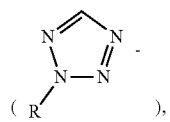

alkyne group (RC≡CH), a halogen group, or an alkene group (RC=CH$_2$).

106. The composition of any of embodiments 101 to 105, wherein the non-cleavable bridge component comprises x polyethylene glycol groups (PEG$_x$), wherein x≥1.
107. The composition of embodiment 106, wherein x≥4.
108. The composition of embodiment 101, wherein the composition comprises antibody-PEG$_8$-SS-HA-N$_3$.
109. The composition of embodiment 101 or embodiment 108, wherein the composition comprises antibody-PEG$_4$-CCH.
110. A composition comprising a cleavable bridge component, the cleavable bridge component comprises a cleavage site, a detectable moiety, and a first chemical ligation group, the cleavage site is at or near a first terminus, and the first chemical ligation group is at or near a second terminus, the first chemical ligation group is stable under physiological conditions.
111. The composition of embodiment 110, wherein the cleavage site comprises a disulfide bond, a vicinal diol, a vicinal hydroxylamine, or a nitrophenyl derivative.
112. The composition of embodiment 110 or 111, wherein the cleavable bridge component comprises more than one detectable moiety.
113. The composition of any of embodiments 110 to 112, wherein the detectable moiety comprises a hapten, a peptide tag, or an oligonucleotide.
114. The composition of embodiment 112, wherein the peptide tag comprises HA-tag, FLAG tag, Myc Tag, V5 Tag, E-Tag, or VSV Tag.
115. The composition of any of embodiments 110 to 114, wherein the cleavable bridge component further comprises a scaffold, wherein the detectable moiety is bound to the scaffold.
116. The composition of embodiment 115, wherein the scaffold comprises lysine.
117. The composition of any of embodiments 110 to 116, wherein the first chemical ligation group comprises an azide

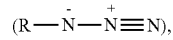

a thioester

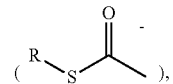

or a tetrazole ring

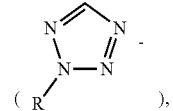

an alkyne group (RC≡CH), a halogen group, or an alkene group (RC=CH$_2$).

118. The composition of embodiment 110, wherein the cleavable bridge component comprises x polyethylene glycol groups (PEG$_x$), wherein x≥1.
119. The composition of embodiment 118, wherein x≥8.
120. A composition comprising a non-cleavable bridge component, the non-cleavable bridge component comprises a second chemical ligation group at or near a terminus, the second chemical ligation group is stable under physiological conditions.
121. The composition of embodiment 120, wherein the second chemical ligation group comprises an alkyne group (RC≡CH), a halogen group, or an alkene group (RC=CH$_2$).
122. The composition of embodiment 120 or 121, wherein the non-cleavable bridge component comprises X polyethylene glycol groups (PEG$_x$), wherein x≥1.
123. The composition of embodiment 122, wherein x≥4.
124. The composition of embodiment 120, wherein the composition comprises PEG$_8$-SS-HA-N$_3$.
125. A method of in situ detection in a sample of a target protein having a post-translational modification, said method comprising:
   binding a first modified binding molecule to the target protein to form a first complex, the first modified binding molecule comprises a cleavable bridge component, the cleavable bridge component comprises a cleavage site, a detectable moiety, and a first chemical ligation group, the cleavage site is more proximal to the first modified binding molecule than is the detectable moiety and the first chemical ligation group, the first chemical ligation group is at a terminus of the cleavable bridge component, the first chemical ligation group is stable under physiological conditions;
   binding a second modified binding molecule to the post-translational modification to form a second complex, the second modified binding molecule comprises a non-cleavable bridge component, the non-cleavable bridge component comprises a second chemical ligation group, the second chemical ligation group is at a terminus of the non-cleavable bridge component, the second chemical ligation group is stable under physiological conditions;

covalently linking the first chemical ligation group to the second chemical ligation group to form a covalently bonded unit;

cleaving the cleavage site of the cleavable bridge component such that the covalently bonded unit is bound to the second modified binding molecule and not the first modified binding molecule;

removing cleavable bridge components that are not part of a covalently bonded unit; and making the detectable moiety visible, wherein the visibility of the detectable moiety indicates the presence of the target protein with the post-translational modification.

The invention claimed is:

1. A composition comprising a first modified binding moiety, wherein the first modified binding moiety comprises:
   (a) at least one a cleavable bridge component; and
   (b) a first antibody is covalently conjugated to the at least one cleavable bridge component;
   wherein the cleavable bridge component has the covalently conjugated structure:
   —[cleavage site]—[detectable moiety]—[chemical ligation group], wherein the cleavage site is more proximal to the first antibody than is the detectable moiety and the chemical ligation group, wherein the chemical ligation group is at or near a terminus of the cleavable bridge component, and wherein the chemical ligation group comprises a first reactive functional group; wherein the cleavage site is selected from the group consisting of a disulfide bond, a vicinal diol, 1,4-Bis(2-hydroxymethyl)benzene ("1,4-BHMB"), 1,4-Bis(2-hydroxethyl)benzene ("1,4-BHEB"), 1,3-Bis(2-hydroxymethyl)benzene ("1,3-BHMB"), 2,5-bis(hydroxymethyl)furan ("2,5-BHMF"), and a vicinal hydroxylamine; wherein the detectable moiety is selected from the group consisting of a peptide tag and an oligonucleotide; and wherein the first reactive functional group is selected from the group consisting of:

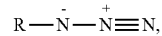

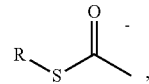

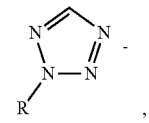

RC≡CH,
RC=CH$_2$,
a halogen, and
a pyridine including one R group,
wherein R is H.

2. The composition of claim 1, wherein the antibody is a primary antibody.

3. The composition of claim 1, wherein the cleavage site comprises a disulfide bond.

4. The composition of claim 1, wherein the detectable moiety is a peptide tag selected from the group consisting of HA-tag, FLAG tag, Myc Tag, V5 Tag, E-Tag, and VSV Tag.

5. The composition of claim 1, wherein the cleavable bridge further comprises at least one polyethylene glycol group.

6. The composition of claim 1, further comprising a linker, where the linker is coupled to the first antibody and the at least one cleavable bridge component.

* * * * *